(12) United States Patent
Stinson et al.

(10) Patent No.: US 7,777,017 B2
(45) Date of Patent: *Aug. 17, 2010

(54) NUCLEIC ACIDS ENCODING OPSONIC MONOCLONAL AND CHIMERIC ANTIBODIES SPECIFIC FOR LIPOTEICHOIC ACID OF GRAM POSITIVE BACTERIA

(75) Inventors: Jeffrey R. Stinson, Brookville, MD (US); Richard F. Schuman, Gaithersburg, MD (US); James Jacob Mond, Silver Spring, MD (US); Andrew Lees, Silver Spring, MD (US); Gerald Walter Fischer, Bethesda, MD (US)

(73) Assignee: Biosynexus Incorporated, Gaithersburg, MD (US)

(*) Notice: Subject to any disclaimer, the term of this patent is extended or adjusted under 35 U.S.C. 154(b) by 0 days.

This patent is subject to a terminal disclaimer.

(21) Appl. No.: 11/724,040

(22) Filed: Mar. 13, 2007

(65) Prior Publication Data
US 2008/0019976 A1    Jan. 24, 2008

Related U.S. Application Data

(60) Division of application No. 10/323,927, filed on Dec. 20, 2002, now Pat. No. 7,250,494, which is a continuation-in-part of application No. 09/097,055, filed on Jun. 15, 1998, now Pat. No. 6,610,293.

(60) Provisional application No. 60/343,503, filed on Dec. 21, 2001.

(51) Int. Cl.
*C07H 21/04*  (2006.01)
*C12N 5/06*   (2006.01)
*C12N 15/00*  (2006.01)
*A61K 39/395* (2006.01)
*C12P 21/04*  (2006.01)
*C12P 21/08*  (2006.01)
*C07K 16/00*  (2006.01)

(52) U.S. Cl. ............. 536/23.53; 424/133.1; 424/139.1; 424/141.1; 424/150.1; 435/69.6; 435/70.21; 435/320.1; 435/326; 530/387.1; 530/387.3; 530/388.1; 530/388.25

(58) Field of Classification Search .................. None
See application file for complete search history.

(56) References Cited

U.S. PATENT DOCUMENTS

| | | | |
|---|---|---|---|
| 4,027,010 A | 5/1977 | Kiselev et al. | |
| 4,197,290 A | 4/1980 | Yoshida | |
| 4,425,330 A | 1/1984 | Norcross et al. | |
| 4,460,575 A | 7/1984 | d'Hinterland et al. | |
| 4,482,483 A | 11/1984 | Curry et al. | |
| 4,719,290 A | 1/1988 | Curry et al. | |
| 4,732,757 A | 3/1988 | Stolle et al. | |
| 4,789,735 A | 12/1988 | Frank et al. | |
| 4,830,852 A | 5/1989 | Marburg et al. | |
| 4,902,616 A | 2/1990 | Fournier et al. | |
| 5,034,515 A | 7/1991 | Proctor | |
| 5,055,455 A | 10/1991 | Pier | |
| 5,153,312 A | 10/1992 | Porro | |
| 5,175,096 A | 12/1992 | Hook et al. | |
| 5,354,654 A | 10/1994 | Ligler et al. | |
| 5,440,014 A | 8/1995 | Hook et al. | |
| 5,505,945 A | 4/1996 | Gristina et al. | |
| 5,530,102 A | 6/1996 | Gristina et al. | |
| 5,538,733 A | 7/1996 | Emery et al. | |
| 5,545,721 A | 8/1996 | Carroll et al. | |
| 5,571,511 A | 11/1996 | Fischer | |
| 5,624,904 A | 4/1997 | Krieger et al. | |
| 5,652,217 A | 7/1997 | Hook et al. | |
| 5,686,600 A * | 11/1997 | Carozzi et al. | |
| 5,770,208 A | 6/1998 | Fattom et al. | |
| 5,840,846 A | 11/1998 | Hook et al. | |
| 5,851,535 A | 12/1998 | Jolivet-Reynaud et al. | |
| 5,955,074 A | 9/1999 | Fischer | |
| 5,955,078 A | 9/1999 | Burnham et al. | |
| 6,005,091 A * | 12/1999 | Blackburn et al. | |
| 6,610,293 B1 | 8/2003 | Fischer et al. | |
| 6,939,543 B2 | 9/2005 | Fischer et al. | |
| 7,250,494 B2 | 7/2007 | Stinson et al. | |
| 2004/0013673 A1 | 1/2004 | Fischer et al. | |
| 2004/0052779 A1 | 3/2004 | Stinson et al. | |

(Continued)

FOREIGN PATENT DOCUMENTS

CN    1421459    6/2003

(Continued)

OTHER PUBLICATIONS

Fundamental Immunology, William E. Paul, M.D. ed., 3rd ed., p. 242, 292-295, 1993.*

(Continued)

*Primary Examiner*—David J. Blanchard
(74) *Attorney, Agent, or Firm*—Lahive & Cockfield, LLP; Amy E. Mandragouras, Esq.

(57) ABSTRACT

The present invention encompasses monoclonal antibodies that bind to lipoteichoic acid (LTA) of Gram positive bacteria. The antibodies also bind to whole bacteria and enhance phagocytosis and killing of the bacteria in vitro. The invention also provides antibodies having human sequences (chimeric, humanized and human antibodies). The invention also sets forth the variable regions of three antibodies within the invention and presents the striking homology between them.

31 Claims, 17 Drawing Sheets

U.S. PATENT DOCUMENTS

2006/0002939 A1   1/2006   Fischer et al.

FOREIGN PATENT DOCUMENTS

| EP | 0724016 | 7/1996 |
|---|---|---|
| WO | WO-89/00999 | 2/1989 |
| WO | WO-90/03398 | 4/1990 |
| WO | WO-93/09811 | 5/1993 |
| WO | WO-93/17044 | 9/1993 |
| WO | WO-93/19373 | 9/1993 |
| WO | WO-94/11026 A2 | 5/1994 |
| WO | WO-96/09321 | 3/1996 |
| WO | WO-96/39518 | 12/1996 |
| WO | WO-97/26010 | 7/1997 |
| WO | WO-98/57994 A2 | 12/1998 |

OTHER PUBLICATIONS

Rudikoff et al. Proc. Natl. Acad. Sci. USA, 79(6):1979-1983, Mar. 1982.*
Colman P. M. Research in Immunology, 145:33-36, 1994.*
Bendig M. M. Methods: A Companion to Methods in Enzymology, 8:83-93, 1995.*
Aasjord and Haaheim, Antibodies to Lipoteichoic Acid from *Staphylococcus aureus*, Acta. Path. Microbiol Immunol. Scand. 93:245-50 (1985).
Ahmad et al., Sequential Release of Antigens from Chloroform-treated *Staphylococcus epidermidis*: Application Towards a Possible Vaccine, J. App. Bacteriol. 69:676-85 (1990).
Ahmed et al., Preparation and Efficacy of Staphylococcal Vaccine by Sequential Release of Antigen from Solvent Treated Bacteria, Soc. Appl. Bacter. 67: xv (1989).
Ames, Assay of Inorganic Phosphate, Total Phosphate and Phosphatase, *Methods in Enzymology* 8:115-18 (1966).
Another Sepsis Drug Down—Immunex's TNF Receptor, Biotechnology Newswatch, A. McGraw-Hill Publication, pp. 2-3 (Oct. 4, 1993).
Baird-Parker, The Basis for the Present Classification of Staphylococci and Micrococci, Recent Advances in Staphylococcal Research, *Ann. N.Y. Acad. Sci.* 236:7-14 (1974).
Baker et al., Multicenter Trial of Intravenous Immunoglobulin (IVIG) to Prevent Late-Onset Infection in Preterm Infants: Preliminary Results, Ped. Res. 25:275A (1989).
Baker et al., Intravenous Immune Globulin for the Prevention of Nosocomial Infection in Low Birth Weight Neonates, New Eng. J. Med. 327:213-19 (1992).
Bonnerjea et al., Protein Purification: The Right Step at the Right Time, Biotechnology 4:954-58 (1986).
Borrebaeck, *Antibody Engineering*, 2nd Ed., Oxford University Press, NY (1995).
Boslego et al., Gonorrhea Vaccines, in Vaccines and Immunotherapy, Chap. 17, Cryz ed., Pergamon Press, pp. 211-23 (1991).
Campbell, Monoclonal Antibodies and Immunosensor Technology, Laboratory Techniques in Biochemistry and Molecular Biology 23, Chapter 1, pp. 1-49 (1991).
Carozzi et al., Response of CAPD Patients with a High Incidence of Peritonitis to Intraperitoneal Immunoglobulin Therapy, Trans. Am. Soc. Artif. Intern. Organs. 34:635-39 (1988).
Carruthers and Kabat, Mediation of Staphylococcal Adherence to Mucosal Cells by Lipoteichoic Acid, Infect Immun. 40:444-46 (1983).
Chugh et al., Adherence of *Staphylococcus epidermidis* to Fibrin-Platelet Clots in Vitro Mediated by Lipoteichoic Acid, Infect Immun. 58:315-19 (1990).
Cieslak et al., Post-Immunization Antibodies to *S. epidermidis* are Broadly Reactive and Opsonic, Ped. Research 31 :275A (1992).
Clapp et al., Use of Intravenously Administered Immunoglobulin to Prevent Nosocomial Sepsis in Low Birth Weight Infants: Reports of a Pilot Study, J. Pediatr. 115:973-78 (1989).
Clark et al., Opsonic Requirements of *Staphylococcus epidermidis*, J. Med. Microbiol. 22:1-7 (1986).
Clark et al., Opsonic Activity of Intravenous Immunoglobulin Preparations Against *Staphylococcus epidermidis*, J. Clin. Pathol. 39:856-60 (1986).
Cockayne et al., Molecular Cloning of a 32-Kilodalton Lipoprotein Component of a Novel Iron-Regulated *Staphylococcus epidermidis* ABC Transporter, Infect. Immun. 66:3767-74 (1998).
Current Methods in Hybridoma Formation, Bartal et al. (ed.) Methods of Hybridoma Formation, Humana Press, Clifton, New Jersey (1987).
Dale et al., Passive Protection of Mice Against Group A Streptococcal Pharyngeal Infection by Lipoteichoic Acid, J. Infect. Dis. 169:319-23 (1994).
De Kimpe et al., The Cell Wall Components Peptidoglycan and Lipoteichoic Acid From *S. aureus* Act in Synergy to Cause Shock and Multiple Organ Failure, Proc. Natl. Acad. Sci. (USA) 92:10359-63 (1995).
Devereux et al., A Comprehensive Set of Sequence Analysis Programs for the VAX, Nuc. Acids Res. 12:387-95 (1984).
Dick et al., Gycoconjugates of Bacterial Carbohydrate Antigens, Contrib. Microbiol & Immunol. 10:48-114 (1989).
Doyle et al., Soluble Macromolecular Complexes Involving Bacterial Teichoic Acids, J. Bacteriol. 124:341-47 (1975).
Drabick, J. et al., "A Monoclonal Antibody Directed Against Lipoteichoic Acid by *Streptococcus pyogenes* is Broadly Cross-reactive with Many Gram Positive Organisms," Abstracts of the General Meeting of the American Society for Microbiology, the Society, Washington, DC, US, vol. 93:109 (1993).
Ellis, New Technologies for Making Vaccines, In Vaccines, Chap. 29, W.B. Saunders co., at 568-75 (Plotkin and Mortimer eds., 1988).
Ellman, Tissue Sulfhydryl Groups, Arch. Biochem. & Biophys. 82:70-77 (1959).
Endl et al., Chemical Composition and Structure of Cell Wall Teichoic Acid of Staphylococci, Arch Microbiol, 135:215-23 (1983).
Espersen et al., Cross-Reactions Between *Staphylococcus epidermidis* and 23 Other Bacterial Species, Acta Path. Microbial. Scand., Sect. B. 89:253-60 (1981).
Espersen et al., Solid-Phase Radioimmunoassay for IgG Antibodies to *Staphylococcus epidermidis*, Arch. Intern. Med. 147:689-93 (1987).
Espersen et al., *Staphylococcus aureus*, in "Antigen Detection to Diagnose Bacterial Infections" vol. II, CRC Press Inc., at 127-34 (Kohler, ed., 1986).
Espersen et al., Enzyme-Linked Immunosorbent Assay for Detection of *Staphylococcus epidermidis* Antibody in Experimental *S. epidermidis* Endocarditis, J. Clin. Microbiol. 23:339-42 (1986).
Etzioni et al., Effect of an Intravenous Gammaglobulin Preparation on the Opsonophagocytic Activity of Preterm Serum Against Coagulase-Negative Staphylococci, Acta. Paediatr. Scand. 79:156-61 (1990).
Exley et al., Monoclonal Antibody to TNF in Severe Septic Shock, Lancet 335:1275-1277 (1990).
Fanaroff et al., A Controlled Trial of Intravenous Immunoglobulin to Reduce Nosocomial Infections in Very Low Birth Weight Infants, New Eng. J. Med. 330:1107-13 (1992).
Fattom et al., Synthesis and Immunologic Propeties in Mice of Vaccines Composed of *Staphylococcus aureus* Type 5 and Type 8 Capsular Polysaccharides Conjugated to *Pseudomonas aeruginosa* Exotoxin A, Infect. & Immun. 58:2367-74 (1990).
Fattom et al., Capsular Polysaccharide Serotyping Scheme for *Staphylococcus epidermidis*, J. Clin. Micro. 30:3270-73 (1992).
Fischer et al., Diminished Bacterial Defences with Intralipid, Lancet 2:819-20 (1980).
Fischer et al., Improved Preparation of Lipoteichoic Acids, Eur. J. Biochem. 133:523-30 (1983).
Fischer et al., Directed Immunoglobulin Enhances Survival in an Intralipid Induced Neonatal Model of Lethal *Staphylococcus epidermidis* Sepsis, Ped. Res. Abstr. Abstract No. 1670 (Apr. 1991).
Fischer et al., Therapeutic Uses of Intravenous Gammaglobulin for Pediatric Infections, Ped. Clin. N. Amer. 35:517-33 (1988).
Fischer et al., Opsonic antibodies to *Staphylococcus epidermidis*: in vitro and in vivo studies using human intravenous immunoglobulin, J. Infect. Dis. 169:324-29 (1994).

Fleer et al., Septicemia Due to Coagulase-Negative Staphylococci in a Neonatal Intensive Care Unit: Clinical and Bacteriological Features and Contaminated Parenteral Fluids as a Source of Sepsis, Pediatr. Infect. Dis. 2:426-31 (1983).

Fleer et al., Opsonic Defense to *Staphylococcus epidermidis* in the Premature Neonate, J. Infect. Dis. 152:930-37 (1985).

Fleury et al., Structural Evidence for Recognition of a Single Epitope by Two Distinct Antibodies, Proteins 40:572-78 (2000).

Fournier, *Staphylococcus aureus*, Vaccines and Immunotherapy, Ch. 13, pp. 166-72 (1991).

Freeman et al., Association of Intravenous Lipid Emulsion and Coagulase-negative *Staphylococcal bacteremia* in Neonatal Intensive Care Units, New Eng. J. Med. 323:301-08 (1990).

Garrett, The Revenge of the Germs or Just Keep Inventing New Drugs, The Coming Plague, Ch. 13, Farrar, Straus and Giroux, (ed.) NY, pp. 411-56 (1994).

Gómez, Isabel et al, "Mapping the Epitope in Cadherin-like Receptors Involved in *Bacillus thuringiensis* Cry1A Toxin Interaction Using Phage Display," The Journal of Biological Chemistry, vol. 276(31):28906-28912 (2001).

Gonzalez and Hill, The Current Status of Intravenous Gamma-globulin Use in Neonates, J. Ped. Infect. Dis. 8:315-22 (1989).

Granato et al., Cell Surface-Associated Lipoteichoic Acid Acts as an Adhesion Factor for Attachment of *Lactobacillus johnsonii* La1 to Human Enterocyte-Like Caco-2 Cell, Appl Environ Microbiol. 65:1071-77 (1999).

Green et al., Antigen-Specific Human Monoclonal Antibodies from Mice Engineered with Human Ig Heavy and Light Chain YACs, Nat. Genet. 7:13-21 (1994).

Gunn, Comparative Virulence of Human Isolates of Coagulase-Negative Staphylococci Tested in an Infant Mouse Weight Retardation Model. J. Clin. Microbiol. 27:507-11 (1989).

Hancock, Bacterial Cell Surface Carbohydrates: Structure and Assembly, Biochem. Soc. Trans. 25:183-87 (1997).

Hague et al., IgM-Enriched Intravenous Immunoglobulin Therapy in Neonatal Sepsis, AJDC 142:1293-96 (1988).

Harlow and Lane, Antibodies: a Laboratory Manual, pp. iii-ix (Cold Spring Harbor Laboratory 1988).

Ichiman et al., Cross Protection of Mice with the Smith Diffuse Strain of *Staphylococcus aureus* versus a type la Strain of Group B Streptococci, Can. J. Microbiol. 28:726-32 (1982).

Ichiman et al., Induction of Resistance with Heat-Killed Unencapsulated Strains of *Staphylococcus epidermidis* Against Challenge with Encapsulated Strains of *Staphylococcus epidermidis*, Microbiol. Immunol. 33:277-86 (1989).

Ichiman et al., Protective Antibodies in Human Sera Against Encapsulated Strains of *Staphylococcus epidermidis*, J. App. Bacter. 63:165-69 (1987).

Ichiman et al., Relation of Human Serum Antibody Against *Staphylococcus epidermidis* Cell Surface Polysaccharide Detected by Enzyme-Linked Immunosorbent Assay to Passive Protection in the Mouse, J. App. Bacter. 71:176-81 (1991).

Ichiman et al., Monoclonal IgM Antibody Protection in Mice Against Infection with an Encapsulated Strain of *Staphylococcus epidermidis*, Can. J. Microbiol. 37:404-07 (1991).

Jackson et al., Monoclonal Antibodies to Immunodeterminants of Lipoteichoic Acids, Infection and Immunity, 43:800-03 (1984).

Jendeberg et al., Engineering of Fc1 and Fc3 From Human Immunoglobulin G to Analyse Subclass Specificity for Staphylococcal Protein A, J. Immunol. Methods 201:25-34 (1997).

Johnsen et al., Studies on Polysaccharide C of *Staphylococcus epidermidis*, Acta Path. Microb. 83:226-34 (1975).

Kantor et al., Development of the Antibody Repertoire as Revealed by Single-Cell PCR of FACS-Sorted B-Cell Subsets, Ann N Y Acad. Sci. 764:224-27 (1995).

Kiser et al., Development and Characterization of a *Staphylococcus aureus* Nasal Colonization Model in Mice, Infection and Immunity 67:5001-06 (1999).

Klein, From Harmless Commensal to Invasive Pathogen, New Eng. J. Med. 323:339-40 (1990).

Kojima et al., Antibody to the Capsular Polysaccharide/Adhesin Protects Rabbits Against Catheter-Related Bacteremia Due to Coagulase-Negative Staphylococci, J. Infect. Dis. 162:435-41 (1990).

Kotani et al., Immunoadjuvant Activities of the Enzymatic Digests of Bacterial Cell Walls Lacking Immunoadjuvancy by Themselves, Biken Journal 20:87-90 (1977).

Lamperi et al., Intraperitoneal Immunoglobulin (Ig) Treatment of Prophylaxis of Bacterial Peritonitis in CAPD, Biomat., Art. Cells, Art. Org. 15:151-59 (1987).

Lee, The Prospects for Developing a Vaccine Against *Staphylococcus aureus*, Trends in Micro. 4:162-66 (1996).

LoBuglio et al., Mouse/Human Chimeric Monoclonal Antibody in Man: Kinetics and Immune Response, P.N.A.S. 86:4220-24 (1986).

Lohman, Kenton L. et al, "Characteristics of Murine Monoclonal Anti-CD4, Epitope Recognition, Idiotype Expression, and Variable Region Gene Sequence," The Journal of Immunology, vol. 149(10):3247-3253 (1992).

Losnegard et al., Immunochemical Studies on Polysaccharides from *Staphylococcus epidermidis*, Acta Path. Microbiol. Scand. 58:493-500 (1963).

Low et al., Mimicking Somatic Hypermutation: Affinity Maturation of Antibodies Displayed on Bacteriophage Using a Bacterial Mutator Strain, J Mol Biol 260:359-68 (1996).

Mancuso et al., Anti-Lipoteichoic Acid Antibodies Enhance Release of Cytokines by Monocytes Sensitized with Lipoteichoic Acid, Infection and Immunity 62:1470-73 (1994).

McDermid et al., A Porcine Model fo *Staphylococcus epidermidis* Catheter-Associated Infection, J. Infect. Dis. 168:897-903 (1993).

Merkus et al., Cyclodextrins in Nasal Drug Delivery, Advan. Drug Deliv. Rev. 36:41-57 (1999).

Modun et al., A Preparation of *Staph. epidermidis* Vaccine by Enzymatic Digestion of Bacterial Cells, J. Appl. Bacterial. 67:xv-xvi (1989).

Modun et al., Extraction by Immune Complexing of Protective Antigens of *Staphylococcus epidermidis*; Application Towards Vaccine Preparation, J. Appl. Bacteriol. 67:xvi (1989).

Modun et al., Cell Envelope Proteins of *Staphylococcus epidermidis* Grown in Vivo in a Peritoneal Chamber Implant, Infect. & Immun. 60:2551-53 (1992).

Modun et al., Staphylococci Express a Receptor for Human Transferrin: Identification of a 42-Kilodalton Cell Wall Transferrin-Binding Protein, Infect & Immun. 62:3850-58 (1994).

Modun et al., The *Staphylococcus aureus* and *Staphylococcus epidermidis* Transferrin-Binding Proteins Are Expressed in vivo During Infection, Microbiology 144:1005-12 (1998).

Nakamura et al., Uptake and Release of Budesonide from Mucoadhesive, pH-Sensitive Copolymers and their Application to Nasal Delivery, J. Control. Release 61:329-35 (1999).

Natsume et al., Screening of Cationic Compounds as an Absorption Enhancer for Nasal Drug Delivery, Int. J. Pharma. 185:1-12 (1999).

Naumova et al., The Occurrence of Teichoic Acids in Streptomycetes, Arch. Microbol. 126:71-75 (1980).

Navarre and Schneewind, Surface Proteins of Gram-Positive Bacteria and Mechanisms of their Targeting to the Cell Wall Envelope, Microbiol. Biol. Rev. 63:174-229 (1999).

Nealon and Mattingly, Role of Cellular Lipoteichoic Acids in Mediating Adherence of Serotype III Strains of Group B Streptococci to Human Embryonic, Fetal and Adult Epithelial Cells, Infect Immun. 43:523-30 (1984).

Nickerson et al., Human and Mouse Monoclonal Antibodies to Blood Group A Substance, Which are Nearly Identical Immunochemically, Use Radically Different Primary Sequences, J. Biol. Chem. 270:12457-65 (1995).

NIH Consensus Conference, Intravenous Immunoglobulin: Prevention and Treatment of Disease, JAMA 264:3189-93 (1990).

Niizuma, Passive Protective Activities of Specific Human Immunoglobulin Against Strain ST67P of *Staphylococcus hyicus* Extracted from Pooled Human Sera, Chem. Abstracts 115:181022v at 713 (1990).

Niizuma, Passive Protective Activities of Specific Human Immunoglobulin Against Strain ST67P of *Staphylococcus hyicus* Extracted from Pooled Human Sera, St. Marianna Med. J. 18:940-46 (1990).

Oeding et al., Classification of Coagulase-Negative Staphylococci in the Diagnostic Laboratory, ACTA Path. Microbiol. Scand. 85:136-40 (1977).

Oshima et al., Comparison of Cell Wall Teichoic Acid Franctions Isolated from Three Different Encapsulated Strains of *Staphylococcus epidermidis*, Ann. Microbiol. 135:353-65 (1984).

Osland et al., Immunochemical Analysis of the Teichoic Acid from *Staphylococcus hyicus*, ACTA Path. Microbiol. Scand. 87:165-69 (1979).

Osland et al., Immunochemical Analysis of the Teichoic Acid from *Staphylococcus hyicus*, ACTA Path. Microbiol. Scand. 88:121-23 (1980).

Patrick et al., Defining *Staphylococcus epidermidis* Cell Wall Proteins, J. Clin. Microbiol. 28:2757-60 (1990).

Patrick, Coagulase-Negative Staphylococci: Pathogens with Increasing Clinical Significance, J. Pediatr. 116:497-507 (1990).

Peterson et al., Effect of Protein A on Staphylococcal Opsonization, Infection and Immunity 15:760-64 (1977).

Peterson et al., Influence of Encapsulation on Staphyloccal Opsonization and Phagocytosis by Human Polymorphonuclear Leukocytes, Infection and Immunity 19:943-49 (1978).

Plaunt et al., Identification of the Innate Human Immune Response to Surface-Exposed Proteins of Coagulase-Negative Staphylococci, J. Clin. Microbiol. 29:857-61 (1991).

Peole-Warren et al., the Role of Vaccination in the Prevention of Staphylococcal Peritonitis in Continuous Ambulatory Peritoneal Dialysis, Per. Dial. Int. 13:176-77 (1993).

Quie et al., Defective Phagocytosis of Staphylococci, Ann. N. Y. Acad. Sci. 236:233-43 (1974).

Ramkissoon-Ganorkar et al., Modulating Insulin-Release Profile from pH/Thermosensitive Polymeric Beads through Polymer Molecular Weight, J. Contr. Release 59:287-98 (1999).

Raymor et al., Lipoteichoic Acid Inhibition of Phagocytosis of *Staphylococcus aureus* by Human Polymorphonuclear Leukocytes, Clin. Immunol. Immunopath. 19:181-89 (1981).

Remington's Pharmaceutical Sciences, pp. xv-xvi (A. Gennaro, ed. Mark Publishing Co. 1990).

Robbins et al., Polysaccharide-Protein Conjugates: A New Generation of Vaccines, J. Infect. Dis. 161:821-32 (1990).

Roitt, Essential Immunology, Blackwell Scientific Publication, Oxford England, Chap. 4, at 55-68 (1988).

Romero-Vivas et al., Mortality Associated with Nosocomial Bacteremia due to Methicillin-Resistant *Staphylococcus aureus*, Clin. Infect. Dis. 21:1417-23 (1995).

Salton, The Bacterial Cell Envelope—A Historical Perspective, in J.-M. Ghuyson and R. Hakenbeck (Ed.), Bacterial Cell Wall, Elsevier Science BV, Amsterdam, pp. 1-22 (1994).

Sambrook et al., Molecular Cloning, pp. xi-xxxviii (Cold Spring Harbor Laboratory 1989).

Santos et al., Functional Leukocyte Administration in Protection Against Experimental Neonatal Infection, Pediatr. Res. 14:1408-1410 (1980).

Schwab et al., Increased Adherence of *Staphylococcus aureus* From Cystic Fibrosis Lungs to Airway Epithelial Cells, Am. Rev. Respir. Dis. 148:365-69 (1993).

Shaio et al., Effect of Immunoglobulin Intravenous on Opsonization of Bacteria by Classic and Alternative Complement Pathways in Premature Serum, Ped. Res. 25:634-40 (1989).

Short Protocols in Molecular Biology, pp. iii-xvi (F. Ausubel et al., eds. Greene Publishing Assoc. 1989).

Shulman et al., A Better Cell Line for Making Hybridomas Secreting Specific Antibodies, Nature 276:269-70 (1978).

Siber, Immune Globulin to Prevent Nosocomial Infections, New Eng. J. Med. 327:269-71 (1992).

Smith et al., Characterization of Cell Envelope Proteins of *Staphylococcus epidermidis* Cultured on Human Perioneal Dialysate, Infect. & Immun. 59:617-24 (1991).

Soto et al., Bacitracin Versus Mupirocin for *Staphylococcus aureus* Nasal Colonization, Infect. Cont. Hosp. Epiderm. 20:351-53 (1999).

Sutherland, Separation and Purification of Bacterial Antigens, Handbook of Experimental Immunology, 3rd ed., at. 2.1-2.17 (D.M. Weir, Ed., 1978).

Suzuki and Makino, Mucosal Drug Delivery Using Cellulose Derivative as a Functional Polymer, J. Control. Release 62:101-07 (1999).

Takada et al., Molecular and Structural Requirements of a Lipoteichoic Acid From *Enterococcus hirae* ATCC 9790 for Cytokine-Inducing, Antitumor, and Antigenic Activities, Infection and Immunity 63:57-65 (1995).

Takada et al., Protection Against Endocarditis due to *Staphylococcus epidermidis* by Immunization with Capsular Polysaccharide/Adhesion, Circulation 86:2539-2546 (1991).

Teti et al., Adherence of Group B Streptococci to Adult and Neonatal Epithelial Cells Mediated by Lipoteichoic Acid, Infect Immun. 55:3057-64 (1987).

Thörig et al., Effect of Immunization on the Induction and Course of Experimental *Streptococcus sanguis* and *Staphylococcus epidermidis* Endocarditis, Infection 8:267-74 (1980).

Timmerman et al., Characterization of a Proteinaceous Adhesin of *Staphylococcus epidermidis* which Mediates Attachment to Polystyrene, Infect & Immun. 59:4187-92 (1991).

Timmerman et al., Characterisation and Functional Aspects of Monoclonal Antibodies Specific for Surface Proteins of Coagulase-Negative Staphylococci, J. Med. Micro. 35:65-71 (1991).

Tojo et al., Isolation and Characterization of a Capsular Polysaccharide Adhesin from *Staphylococcus epidermidis*, J. Infect. Dis. 157:713-22 (1988).

Tomasz, The Staphylococcal Cell Wall, in V.A. Fischetti et al. (Ed.) Gram-Positive Pathogens, Ch. 36, pp. 351-355 (2000).

Van Bronswijk et al., Heterogeneity in Opsonic Requirements of *Staphylococcus epidermidis*: Relative Importance of Surface Hydrophobicity, Capsules and Slime, Immunol. 67:81-86 (1989).

Verbrugh et al., Opsonic Recognition of Staphylococci Mediated by Cell Wall Peptidoglycan: Antibody-Independent Activation of Human Complement and Opsonic Activity of Peptidoglycan Antibodies, J. Immunol. 124:1167-73 (1980).

Verhoef et al., Opsonic Requirements for Staphylococcal Phagocytosis, Immunology 33:191-97 (1977).

Verhoef et al., *Staphylococcus epidermidis* Endocarditis and *Staphylococcus epidermidis* Infection in an Intensive Care Unit, Scand. J. Infect. Dis. Supp 41:56-63 (1983).

Wadström, Molecular Aspects of Bacterial Adhesion, Colonization, and Development of Infections Associated with Biomaterials, J. Invest. Surgery 2:353-60 (1989).

Wagner et al., The Diversity of Antigen-Specific Monoclonal Antibodies from Transgenic Mice Bearing Human Immunoglobulin Gene Miniloci, Eur J Immunol 24:2672-81 (1994).

Wagner et al., Antibodies Generated from Human Immunoglobulin Miniloci in Transgenic Mice, Nuc. Acids Res. 22:1389-93 (1994).

Wang and Stollar, Human Immunoglobulin Variable Region Gene Analysis by Single Cell RT-PCR, J. Immunol. Methods 244:217-25 (2000).

Waldvogel, *Staphylococcus aureus* (Including Toxic Shock Syndrome), in Mandell, G.L. et al. (ed.) Principles and Practices of Infectious Diseases, Third Edition, Churchill Livingstone, New York, Ch. 173, pp. 1489-1510 (1990).

Wedrén, On Chronic Prostatitis with Special Studies of *Staphylococcus epidermidis*, Scand. J. Urology & Nephrol. Suppl. 123:3-36 (1989).

Weisman et al., Intravenous Immune Globulin Prophylaxis on Late-Onset Sepsis in Premature Neonates, J. Ped. 125:922-30 (1994).

Wergeland et al., Antibodies to Staphylococcal Peptidoglycan and its Peptide Epitopes, Teichoic Acid, and Lipoteichoic Acid in Sera from Blood Donors and Patients with Staphylococcal Infections, J. Clin. Microbiol. 27:1286-91 (1989).

Wergeland et al., Antibodies to Various Bacterial Cell Wall Peptidoglycans in Human and Rabbit Sera, J. Clin. Microbiol. 25:540-45 (1987).

West et al., Detection of Anti-Teichoic Acid Immunoglobulin G Antibodies in Experimental *Staphylococcus epidermidis* Endocarditis, Infection and Immunity 42:1020-1026 (1983).

Wheat, Analysis of Hexosamines in Bacterial Polysaccharides by Chormatographic Procedures, Methods in Enzymology 8:60-78 (1966).

Wilcox et al., Variation in the Expression of Cell Envelope Proteins of Coagulase-Negative Staphylococci Cultured Under Iron-Restricted Conditions in Human Peritoneal Dialysate, J. Gen. Microbiol. 137:2561-2570 (1991).

Wilkinson, Immunochemistry of Purified Polysaccharide Type Antigens of Group B Streptococcal Types la, lb, and lc, Infect. Immun. 11:845-852 (1975).

Williams et al., Protein Antigens of *Staphylococcus epidermidis* Grown Under Iron-Restricted Conditions in Human Peritoneal Dialysate, FEMS Microbiol. Ltrs. 50:29-33 (1988).

Winter, Greg et al., "Humanized antibodies," *Immunology Today*, vol. 14(6):243-246 (1993).

Winter et al., Making Antibodies by Phage Display Technology, Annu. Rev. Immunol. 12:433-55 (1994).

Wortham et al., Enhanced Protective Antibody Response to PspA after Intranasal or Subcutaneous Injections of PspA Genetically Fused to Granulocyte-Macrophage Colony-Stimulating Factor or Interleukin-2, Infection and Immunity 66:1513-1520 (1998).

Yamada et al., Possible Common Biological and Immunological Properties for Detecting Encapsulated Strains of *Staphylococcus epidermidis*, J. Clin. Microbiol. 26:2167-72 (1988).

Yang et al., Mechanisms of Bacterial Opsonization by Immune Globulin Intravenous: Correlation of Complement Consumption of Opsonic Activity and Protective Efficacy, J. Infect. Dis. 159:701-07 (1989).

Yoshida et al., Mouse Virulent Starin of *Staphylococcus epidermidis*, Jap. J. Microbiol. 20:209-17 (1976).

Yoshida et al., Staphylococcal Capsular Vaccine for Preventing Mastitis in Two Herds in Georgia, J. Dairy Sci. 67:620-27 (1984).

Yoshida et al., Cross Protection Between a Strain of *Staphylococcus epidermidis* and Eight Other Species of Coagulase-Negative Staphylococci, Can. J. Microbiol. 34:913-15 (1988).

Yoshida et al., Immunological Response to a Strain of *Staphylococcus epidermidis* in the Rabbit: Production of Protective Antibody, J. Med. Microbiol. 11:371-77 (1977).

Yoshida et al., Cross Protection Between an Encapsulated Strain of *Staphylococcus hyicus* and Encapsulated Strains of *Staphylococcus aureus*, J. App. Bact. 65:491-99 (1988).

Yoshitomi, Serological Differentiation of Strains of *Staphylococcus epidermidis* by the Soft Agar Technique, St. Marianna Med. J. 17:166-74 (1989).

Irving, Robert A. et al., "Robosome display and affinity maturation: from antibodies to single V-domains and steps towards cancer therapeutics," *Journal of Immunological Methods*, vol. 248:31-45 (2001).

Kipriyanov, Sergey M. et al., "Generation of Recombinant Antibodies," *Molecular Biotechnology*, vol. 12:173-201 (1999).

Maynard, J. et al., "Antibody engineering," *Annu. Rev. Biomed. Eng.*, vol. 2:339-376 (2000).

European Office Action for Application No. 02794357.0, dated Jan. 28, 2009.

U.S. Appl. No. 12/317,718, Fischer et al.

Hamada, Shigeyuki et al., "Characterization of a Monoclonal Antibody Specific for Lipoteichoic Acid from Various Gram-Positive Bacteria," *Microbial. Immunol.*, vol. 28(9):1009-1021 (1984).

* cited by examiner

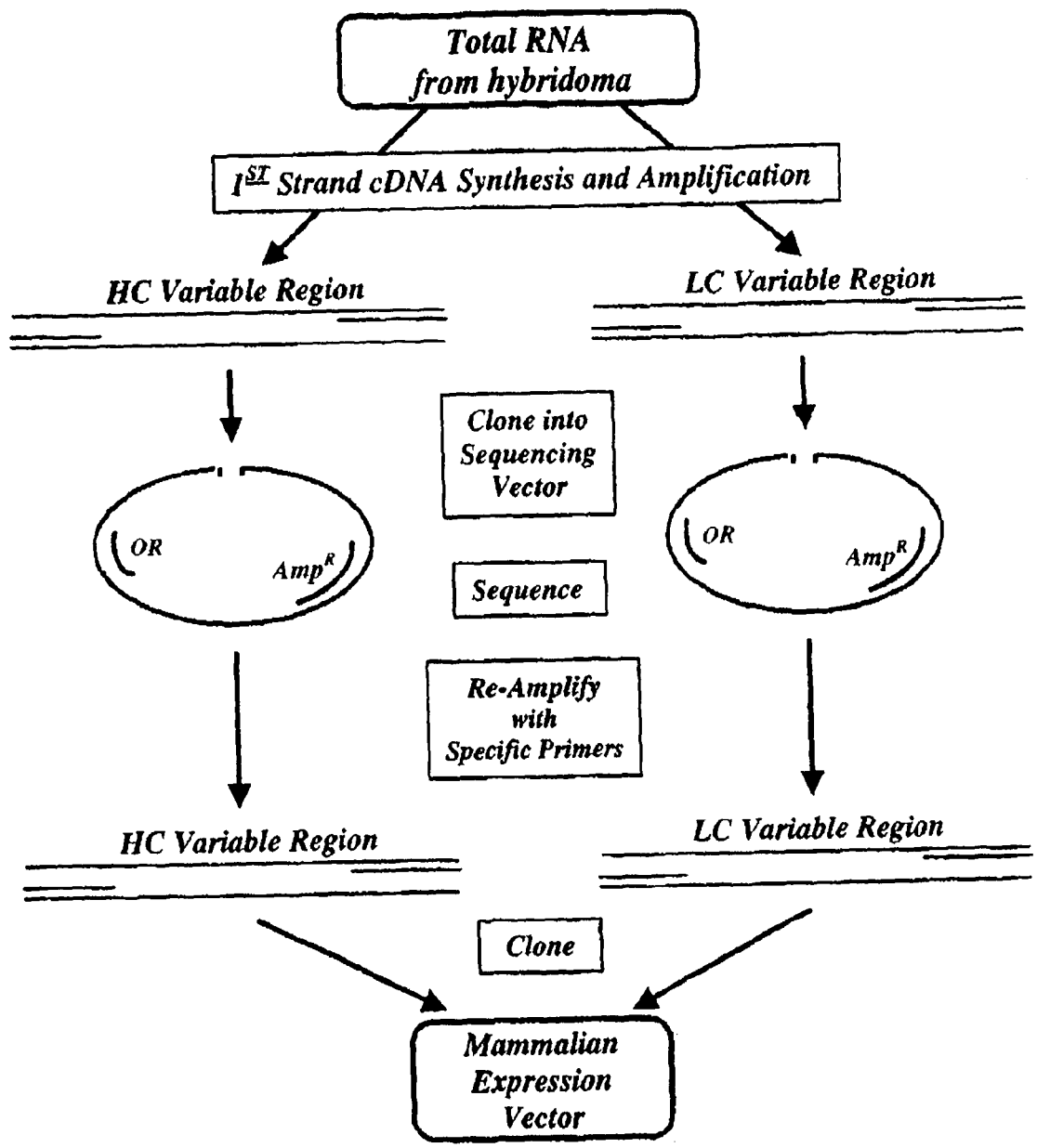

FIGURE 4

| Name | Length | Description | Sequence |
|---|---|---|---|
| JSBX-1 | 40 | Mouse HCV front primer for Megavector | TGTTTTCGTACGTCTTGTCCGARGTRMAGCTKSAKGAGWC<br>SEQ ID NO: 1 |
| JSBX-4 | 40 | Mouse HCV front primer for Megavector | TGTTTTCGTACGTCTTGTCCGAVGTGMWGCTKGTGGAGWC<br>SEQ ID NO: 2 |
| JSBX-9A | 32 | Mouse LCV front primer for Megavector | TACCGTACCGGTGACATTGTGMTGWCMCARTC<br>SEQ ID NO: 3 |
| JSBX-11A | 32 | Mouse LCV front primer for Megavector | TACCGTACCGGTGAYATYMAGATGACMCAGWC<br>SEQ ID NO: 4 |
| JSBX-18 | 23 | Mouse kappa reverse primer | GCACCTCCAGATGTTAACTGCTC<br>SEQ ID NO: 5 |
| JSBX-25A | 22 | Mouse IgG reverse primer 1(23-144) | CTGGACAGGGMTCCAKAGTTCC<br>SEQ ID NO: 6 |
| JSBX-46 | 27 | A120 HCV front primer for Megavector | AAAACCCCGTACGTCTTGTCCGAAGTG<br>SEQ ID NO: 7 |
| JSBX-47 | 32 | A120 HCV back primer for Megavector | ATCTGGGAATTCTGAGGAGACGGTGACTGAGG<br>SEQ ID NO: 8 |
| JSBX-48 | 27 | A120 LCV front primer for Megavector | ATATTTACCGGTGACATTGTGCTGTCC<br>SEQ ID NO: 9 |
| JSBX-49 | 27 | A120 LCV back primer for Megavector | ATAGGATTCGAAAAGTGTACTTACGTTTGATTTCCAGCTTGGTGC<br>SEQ ID NO: 18 |

Note: each of the following letters is used to denote an equal mixture of nucleotides in that position: B = C, G, or T; D = A, G, or T; K = G or T; M = A or C; R = A or G; S = C or G; V = A, C, or G; W = A or T; Y = C or T.

FIGURE 5

Light Chain

D I V L S Q S P A I L S A S P G E K V T
GACATTGTGCTGTCCCAGTCTCCAGCAATCCTGTCTGCATCTCCAGGGGAGAA
    GGTCACA
CTGTAACACGACAGGGTCAGAGGTCGTTAGGACAGACGTAGAGGTCCCCTCTT
    CCAGTGT

M T C R A S S S V S Y M H W Y Q Q K P G
ATGACTTGCAGGGCCAGCTCAAGTGTAAGTTACATGCACTGGTACCAGCAGAA
    GCCAGGA
TACTGAACGTCCCGGTCGAGTTCACATTCAATGTACGTGACCATGGTCGTCTTC
    GGTCCT

S S P K P W I Y A T S N L A S G V P A R
TCCTCCCCCAAACCCTGGATTTATGCCACATCCAACCTGGCTTCTGGAGTCCCT
    GCTCGC
AGGAGGGGGTTTGGGACCTAAATACGGTGTAGGTTGGACCGAAGACCTCAGG
    GACGAGCG

F S G S G S G T S Y S L T I S R V E A E
TTCAGTGGCAGTGGGTCTGGGACCTCTTACTCTCTCACAATCAGCAGAGTGGA
    GGCTGAA
AAGTCACCGTCACCCAGACCCTGGAGAATGAGAGAGTGTTAGTCGTCTCACCT
    CCGACTT

D A A T Y Y C Q Q W S S N P P T F G G G
GATGCTGCCACTTATTACTGCCAGCAGTGGAGTAGTAACCCACCGACGTTCGG
    TGGAGGC
CTACGACGGTGAATAATGACGGTCGTCACCTCATCATTGGGTGGCTGCAAGCC
    ACCTCCG

T K L E I K                  SEQ ID NO: 10
ACCAAGCTGGAAATCAAA           SEQ ID NO: 11
TGGTTCGACCTTTAGTTT

FIGURE 6

Heavy Chain

```
    E  V  M  L  V  E  S  G  E  G  L  V  Q  P  K  G  S  L  K  L
GAAGTGATGCTTGTGGAGTCTGGTGAAGGATTGGTGCAGCCTAAAGGGTCATT
    GAAACTC
CTTCACTACGAACACCTCAGACCACTTCCTAACCACGTCGGATTTCCCAGTAAC
    TTTGAG

S  C  A  A  S  G  F  T  F  N  T  Y  A  M  N  W  V  R  Q  A
TCATGTGCAGCCTCTGGATTCACCTTCAATACCTACGCCATGAACTGGGTCCGC
    CAGGCT
AGTACACGTCGGAGACCTAAGTGGAAGTTATGGATGCGGTACTTGACCCAGGC
    GGTCCGA

P  G  K  G  L  E  W  V  A  R  I  R  S  K  S  N  N  Y  A  T
CCAGGAAAGGGTTTGGAATGGGTTGCTCGCATAAGAAGTAAAAGTAATAATTAT
    GCAACA
GGTCCTTTCCCAAACCTTACCCAACGAGCGTATTCTTCATTTTCATTATTAATAC
    GTTGT

Y  Y  A  D  S  V  K  D  R  F  T  I  S  R  D  D  S  Q  S  M
TATTATGCCGATTCAGTGAAAGACAGGTTCACCATCTCCAGAGATGATTCACAA
    AGCATG
ATAATACGGCTAAGTCACTTTCTGTCCAAGTGGTAGAGGTCTCTACTAAGTGTTT
    CGTAC

L  Y  L  Q  M  N  N  L  K  T  E  D  T  A  M  Y  Y  C  V  R
CTCTATCTGCAAATGAACAACTTGAAGACTGAGGACACAGCCATGTATTACTGT
    GTGAGA
GAGATAGACGTTTACTTGTTGAACTTCTGACTCCTGTGTCGGTACATAATGACA
    CACTCT

R  G  G  K  E  T  D  Y  A  M  D  Y  W  G  Q  G  T  S  V  T
CGGGGTGGTAAAGAGACTGACTATGCTATGGACTACTGGGGTCAAGGAACCTC
    AGTCACC
GCCCCACCATTTCTCTGACTGATACGATACCTGATGACCCCAGTTCCTTGGAGT
    CAGTGG

V  S  S                SEQ ID NO: 12
GTCTCCTCA                  SEQ ID NO: 13
CAGAGGAGT
```

FIGURE 9A

```
A110 LCV  GATTATCGTTCTCTCCCAGTCTCCAGCAATCCTGTCTGCATCTCC
A120 LCV  GACATTGTGCTGTCCCAGTCTCCAGCAATCCTGTCTGCATCTCC
391.4 LCV CAAATTGTGCTGACTCAGTCTCCAGCAATCCTGTCTGCATTTCC

AGGGGAAAAGGTCACAATGACTTGCAGGGCCAGCTCAAGTGTAAATTACA
AGGGGAGAAGGTCACAATGACTTGCAGGGCCAGCTCAAGTGTAAGTTACA
AGGGGAGAAGGTCACAATGACTTGCAGGGCCAGCTCAAGTGTAAGTTACA

TGCACTGGTACCAGCAGAAGCCAGGATCCTCCCCCAAACCCTGGATTTCT
TGCACTGGTACCAGCAGAAGCCAGGATCCTCCCCCAAACCCTGGATTTAT
TGCACTGGTACCAGCAGAAGCCAGGATCCTCCCCCAAACCCTGGATTTAT

GCCACATCCAACCTGGCTTCTGGAGTCCCTGCTCGCTTCAGTGGCAGTGG
GCCACATCCAACCTGGCTTCTGGAGTCCCTGCTCGCTTCAGTGGCAGTGG
GCCACATCCAACCTGGCTTCTGGAGTCCCTACTCGCTTCAGTGGCAGTGG

GTCTGGGACCTCTTACTCTCTCACAATCAGCAGAGTGGAGGCTGAAGATG
GTCTGGGACCTCTTACTCTCTCACAATCAGCAGAGTGGAGGCTGAAGATG
GTCTGGGACCTCTTACTCTCTCACAATCAGCAGAGTGGAGGCTGAAGATG

CTGCCACTTATTACTGCCAGCAGTGGAGTAGTAACCCACCCACGTTCGGA
CTGCCACTTATTACTGCCAGCAGTGGAGTAGTAACCCACCGACGTTCGGT
TTGCCACTTATTACTGCCTACAGTGGACTAGTAACCCACCCACGTTCGGT
```

GGGGGGACCATGCTGGAAATAAAA    SEQ ID NO: 14
GGAGGCACCAAGCTGGAAATCAAA    SEQ ID NO: 11
GCTGGGACCAAGCTGGAGCTGAAA    SEQ ID NO: 19

FIGURE 9B

| | |
|---|---|
| A110 HCV | GAAGTGATGCTGGTGGAGTCTGGTGGAGGATTGGTG |
| A120 HCV | GAAGTGATGCTTGTGGAGTCTGGTGAAGGATTGGTG |
| 391.4 HCV | GAAGTGAAGCTTCATGAGTCTGGTGGAGGATTTGTG |

CAGCCTAAAGGGTCATTGAAACTCTCATGTGCAGCCTCTGGATTCACCTT
CAGCCTAAAGGGTCATTGAAACTCTCATGTGCAGCCTCTGGATTCACCTT
CAGCCTAAAGGGTCATTGAAACTCTCATGTGCAGCCTCTGGATTCACCTT

CAATAACTACGCCATGAATTGGGTCCGCCAGGCTCCAGGAAAGGGTTTGG
CAATACCTACGCCATGAACTGGGTCCGCCAGGCTCCAGGAAAGGGTTTGG
CAATGCCTACGCCATGAACTGGGTCCGCCAGGCTCCAGGAAAGGGTTTGG

AATGGGTTGCTCGCATAAGAAGTAAAAGTAATAATTATGCAACATTTTAT
AATGGGTTGCTCGCATAAGAAGTAAAAGTAATAATTATGCAACATATTAT
AATGGGTTGCTCGCATAAGAAGTAAAAGTAATAATTATGAAACATATTAT

GCCGATTCAGTGAAAGACAGGTTCACCATCTCCAGAGATGATTCACAAAG
GCCGATTCAGTGAAAGACAGGTTCACCATCTCCAGAGATGATTCACAAAG
GCCGATTCAGTGAAAGACAGGTTCACCATCTCCAGAGATGATTCACAATA

CATGCTCTATCTGCAAATGAACAACTTGAAAAC**TGAGGACACAGCCATGT
CATGCTCTATCTGCAAATGAACAACTTGAAGAC**TGAGGACACAGCCATGT
CATGGTCTATCTGCAAATGAACAACCTGAAAAG**TGAGGACACAGCCATGT

ATTACTGTGTGAGACGGGGGGCTTCAGGG---ATTGACTATGCTATGGA
ATTACTGTGTGAGACGGGGTGGTAAAGAG---ACTGACTATGCTATGGA
ATTATTGTGTGAGGAGAGGGTCGATGCGGTCCGCTTATTATGCAATGGA

| | |
|---|---|
| CTACTGGGGTCAAGGAACCTCACTCACCGTCTCCTCA | SEQ ID NO: 15 |
| CTACTGGGGTCAAGGAACCTCAGTCACCGTCTCCTCA | SEQ ID NO: 13 |
| CTACTGGGGTCAAGGAACCTCAGTCACCGTCTCCTCA | SEQ ID NO: 20 |

FIGURE 10A

A110  DIVLSQSPAILSASPGEKVTMTC RASSSVNYMH WYQQKPGSSPKPWIS

A120  DIVLSQSPAILSASPGEKVTMTC RASSSVSYMH WYQQKPGSSPKPWIY 391.4 QIVLTQSPAILSAFPGEKVTMTC RASSSVSYMH WYQQKPGSSPKPWIY

ATSNLAS GVPARFSGSGSGTSYSLTISRVEADAATYYC QQWSSNPPT

ATSNLAS GVPARFSGSGSGTSYSLTISRVEADAATYYC QQWSSNPPT

ATSNLAS GVPTRFSGSGSGTSYSLTISRVEADVATYYC QQWSSNPPT

FGGGTMLEIK      SEQ ID NO: 16

FGGGTKLEIK      SEQ ID NO: 10

FGAGTKLELK      SEQ ID NO: 21

FIGURE 10B

A110  EVMLVESGGGLVQPKGSLKLSCAAS GFTFNNYAMN
WVRQAPGKGLEWVA

A120  EVMLVESGGGLVQPKGSLKLSCAAS GFTFNTYAMN
WVRQAPGKGLEWVA 391.4 EVKLHESGGGFVQPKGSLKLSCAAS GFTFNAYAMN
WVRQAPGKGLEWVA

RIRSKSNNYATFYADSVKD RFTISRDDSQSMLYLQMNNLKTEDTAMYYCVR

RIRSKSNNYATYYADSVKD RFTISRDDSQSMLYLQMNNLKTEDTAMYYCVR

RIRSKSNNYETYYADSVKD  FTISRDDSQYMVYLQMNNLKSEDTAMYYCVR

RGA-SGIDYAMDY WGQGTSLTVSS       SEQ ID NO: 17

RGG-KETDYAMDY WGQGTSVTVSS       SEQ ID NO: 12

RGSMRSYYYAMDY WGQGTSVTVSS       SEQ ID NO: 22

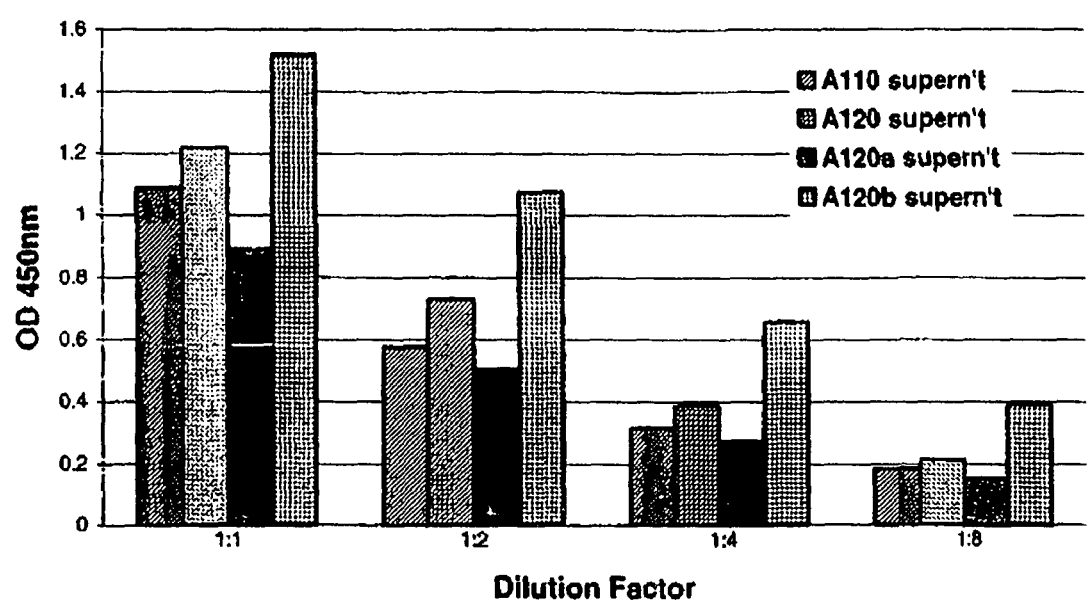

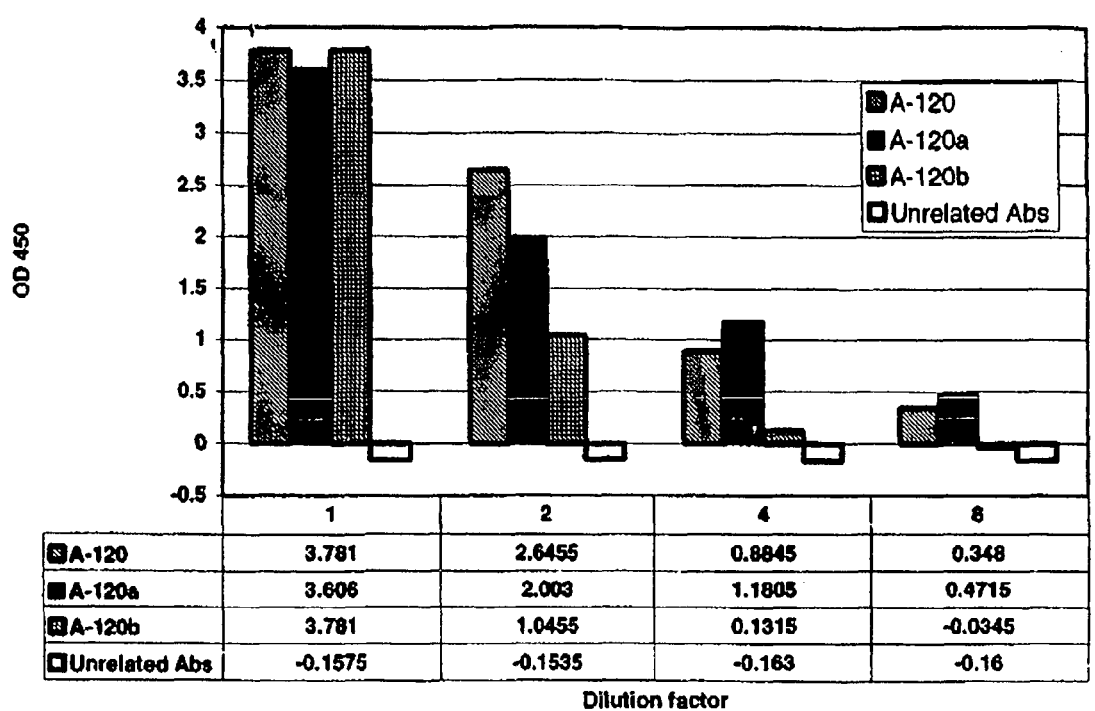

NUCLEIC ACIDS ENCODING OPSONIC MONOCLONAL AND CHIMERIC ANTIBODIES SPECIFIC FOR LIPOTEICHOIC ACID OF GRAM POSITIVE BACTERIA

CROSS-REFERENCE TO RELATED APPLICATIONS

This application is a divisional of U.S. patent application Ser. No. 10/323,927, filed Dec. 20, 2002 which issued as U.S. Pat. No. 7,250,494 on Jul. 31, 2007, which is a continuation-in-part of U.S. patent application Ser. No. 09/097,055, filed Jun. 15, 1998, now U.S. Pat. No. 6,610,293, and is further based on and claims the benefit of U.S. Provisional Application Ser. No. 60/343,503, filed Dec. 21, 2001.

This application also relates to U.S. Pat. Nos. 5,571,511, 5,955,074, and U.S. patent application Ser. No. 09/097,055, filed Jun. 15, 1998, now issued as U.S. Pat. No. 6,610,293. Each of the above-referenced applications is incorporated herein by reference for all purposes.

DESCRIPTION OF THE INVENTION

1. Field of the Invention

This invention in the fields of immunology and infectious diseases relates to antibodies that are specific for Gram positive bacteria, particularly to bacteria that bear lipoteichoic acids on their surfaces. The invention includes monoclonal and chimeric antibodies, as well as fragments, regions and derivatives thereof. This invention further relates to sequences of the variable region that enhance the antibody's opsonic activity. The antibodies of the invention may be used for diagnostic, prophylactic and therapeutic applications.

2. Background Of the Invention

The search for agents to combat bacterial infections has been long and arduous. The development of antibiotics has brought us from the time when sepsis associated with amputation was associated with a 50 percent mortality rate. Today's challenge, however, is the increasing development of bacteria that are resistant to antibiotics, such as members of the genera *Staphylococcus*.

Staphylococci are particularly worrisome because they commonly colonize humans and animals and are an important cause of human morbidity and mortality. Because of their prevalence on the skin and mucosal linings, staphylococci are ideally situated to produce both localized and systemic infections. Of the staphylococci, both *S. aureus*, a coagulase positive bacteria, and *S. epidermidis*, a coagulase negative species, are the most problematic. In fact, *S. aureus* is the most virulent *Staphylococcus*, producing severe and often fatal disease in both normal and immunocompromised hosts. *S. epidermidis* has become one of the major causes of nosocomial (hospital acquired) infection in patients with impaired immune responses or those whose treatments involve the placement of foreign objects into the body, such as patients who receive continuous ambulatory peritoneal dialysis and patients receiving parenteral nutrition through central venous catheters (25). Indeed, *S. epidermidis* is now recognized as a common cause of neonatal nosocomial sepsis, and infections frequently occur in premature infants that have received parenteral nutrition. Moreover, in recent years, the involvement of *S. epidermidis* in neonatal infection has increased dramatically. Indeed, for every 10 babies diagnosed with bacterial sepsis seven or more days after birth (indicative of post-partum bacterial exposure), six of those are infected with *S. epidermidis*. Untreated, *Staphylococcus* infections in newborns can result in multiple organ failure and death in two to three days. Antibiotics are only partially effective and, unfortunately, the rise in multiply drug resistant strains of *Staphylococcus* renders antibiotic treatments less and less effective.

The problems of antibiotic resistance are so significant that they have reached the lay press. See, e.g., *The Washington Post* "Microbe in Hospital Infections Show Resistance to Antibiotics," May 29, 1997; *The Washington Times*, "Deadly bacteria outwits antibiotics," May 29, 1997. And this concern is borne out by the scientific literature. See L. Garrett, *The Coming Plague*, "The Revenge of the Germs or Just Keep Inventing New Drugs" Ch. 13, pgs. 411-456, Farrar, Straus and Giroux, N.Y., Eds. (1994). In one study, the majority of staphylococci isolated from blood cultures of septic infants were resistant to multiple antibiotics (10). Another study describes methicillin-resistant *S. aureus* (31). There is no doubt that the emergence of antibiotic resistance among clinical isolates is making treatment difficult (18).

The other possible route of treatment is the administration of antibodies. Antibodies protect against bacterial attack by recognizing and binding to antigens on the bacteria to thereby facilitate the removal or "clearance" of the bacteria by a process called phagocytosis, wherein phagocytic cells (predominantly neutrophils and macrophages) identify, engulf, and subsequently destroy the invading bacteria. However, bacteria have developed mechanisms to avoid phagocytosis, such as the production of a "capsule" to which phagocytes cannot adhere or the production of toxins that actually poison the encroaching phagocytes. Antibodies overcome these defenses by, for example, binding to the toxins to thereby neutralize them. More significantly, antibodies may themselves bind to the capsule to coat it, in a process called opsonization, to make the bacteria extremely attractive to phagocytes and to enhance their rate of clearance from the bloodstream.

Confounding the use of administered antibodies, however, are conflicting reports in the literature. For example, the immunization studies of Fattom et al. demonstrated that opsonization of *S. epidermidis* was related to the specific capsule type, as with *S. aureus* and other encapsulated Gram positive bacteria such as *Streptococcus pneumonia* (6). In another study, Timmerman et al. identified a surface protein of *S. epidermidis* that induced opsonic monoclonal antibodies (39). Timmerman et al. also identified other monoclonal antibodies that bound to non-homologous *S. epidermidis* strains, but only the monoclonal antibody produced to the homologous strain was opsonic, thus opsonization was enhanced only to the homologous strain but not to heterologous strains. Accordingly, based on the studies of Fattom et al., and Timmerman et al., and others in the field (and in contrast to our own studies as set forth in U.S. Pat. Nos. 5,571,511 and 5,955,074), one would not expect that an antibody that is broadly reactive to multiple strains of *S. epidermidis* and to *S. aureus* would have opsonic activity against each strain. This is particularly true for antibodies that bind to both coagulase positive and coagulase negative staphylococci.

Further exacerbating the problem, the role of the common surface antigens on staphylococci has been unclear. For example, while lipoteichoic acid and teichoic acid make up the majority of the cell wall of *S. aureus*, there was no prior appreciation that antibodies to lipoteichoic acid and teichoic acid could be protective. Indeed, anti-teichoic acid antibodies have been often used as controls. For example, Fattom et al. examined the opsonic activity of antibodies induced against a type-specific capsular polysaccharide of *S. epidermidis*, using as controls antibodies induced against teichoic acids and against *S. hominus*. While type-specific antibodies were highly opsonic, anti-teichoic acid antibodies were not functionally different from the anti-*S. hominus* antibodies (6).

Similarly, in Kojima et al., the authors assessed the protective effects of antibody to capsular polysaccharide/adhesion against catheter-related bacteremia due to coagulase negative staphylococci and specifically used a strain of *S. epidermidis* that expresses teichoic acid as a control ((16); see page 436, Materials and Methods, left column, first paragraph; right column, third paragraph). In a later study, Takeda et al. (38), the authors reached a more explicit conclusion against the utility of anti-techoic antibodies:

> Immunization protocols designed to elicit antibody to techoic acid but not to PS/A afforded no protection against bacteremia or endocarditis (38).

Thus, the role of antibodies in the protection against infections by Gram positive bacteria, particularly Staphylococci such as *S. aureus* and *S. epidermidis*, has not been clear, and there is a need in the art for monoclonal antibodies to both protect against such bacterial infection and to help elucidate the role of such antibodies against such infection. There is also a need in the art for sequence analysis of such antibodies so that antibodies of enhanced binding and opsonic activity can be identified and/or produced.

SUMMARY OF THE INVENTION

The present invention encompasses broadly reactive, opsonic, and protective monoclonal and chimeric antibodies that bind to lipoteichoic acid (LTA) of Gram positive bacteria. The antibodies also bind to whole bacteria and enhance phagocytosis and killing of the bacteria in vitro and enhance protection from lethal infection in vivo. The present invention further encompasses opsonic antibodies to LTA that share a high degree of sequence homology. The present invention also encompasses antibodies having variable regions derived from two or more different anti-LTA antibodies.

BRIEF DESCRIPTION OF THE DRAWINGS

FIG. 3 shows the cDNA cloning strategy for the heavy and light chain variable regions of A120.

FIG. 4 shows the oligonucleotide primers used to amplify the variable region fragments. (SEQ ID NOs: 1-9 and 18)

FIG. 5 shows the amino acid sequence (SEQ ID NO: 10) and the polynucleotide sequence (SEQ ID NO: 11) of the A120 light chain variable region.

FIG. 6 shows the amino acid sequence (SEQ ID NO: 12) and the polynucleotide sequence (SEQ ID NO: 13) of the A120 heavy chain variable region.

FIG. 9 shows an alignment of (A) the A110 light chain variable region cDNA (SEQ ID NO: 14), the A120 light chain variable region cDNA (SEQ ID NO: 11) and the 391.4 light chain variable region cDNA (SEQ ID NO: 19) and (B) the A110 heavy chain variable region cDNA (SEQ ID NO: 15), the A120 heavy chain variable region cDNA (SEQ ID NO: 13) and the 391.4 heavy chain variable region cDNA (SEQ ID NO: 20). The nucleotides that differ between any two sequences are boxed.

FIG. 10A shows an alignment of the A110 light chain variable region polypeptide sequence (SEQ ID NO: 16), the A120 light chain variable region polypeptide sequence (SEQ ID NO: 10) and the 391.4 light chain variable region polypeptide sequence (SEQ ID NO: 21). FIG. 10B shows an alignment of the A110 heavy chain variable region polypeptide sequence (SEQ ID NO: 17), the A120 heavy chain variable region polypeptide sequence (SEQ ID NO: 12) and the 391.4 heavy chain variable region polypeptide sequence (SEQ ID NO: 22). The complementarity determining regions (CDRs) are underlined and the amino acids that differ between any two sequences are boxed.

FIG. 15 provides the results of the chimeric antibody production ELISA. All antibodies shown are human/mouse chimeras. A110 contains both the heavy and light chain variable regions from A110. A120 contains both the heavy and light chain variable regions from A120. A120a contains the heavy chain variable region from A110 and the light chain variable region from A120. A120b contains the heavy chain variable region from A120 and the light chain variable region from A110.

FIG. 16 provides the results of the experiment to determine chimeric antibody binding to the *S. aureus* LTA. The antibodies used are the same as in FIG. 15.

DETAILED DESCRIPTION OF THE INVENTION

Definitions

Figure 1:
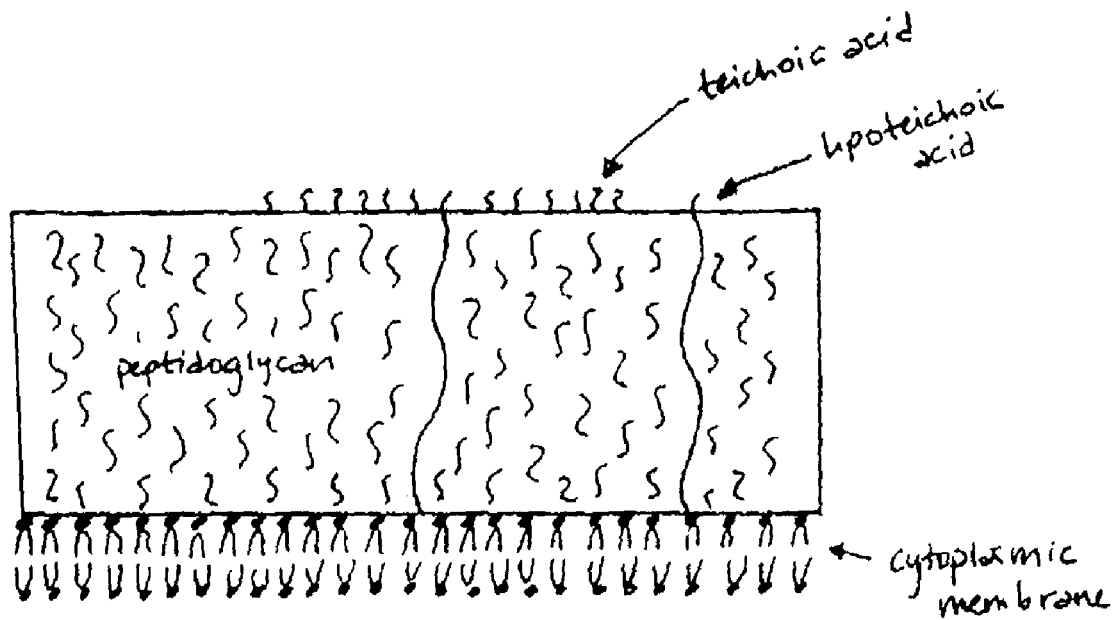
FIG. 1 provides a schematic representation of lipoteichoic acid (LTA) in the Gram positive bacterial cell wall.
Figure 2:
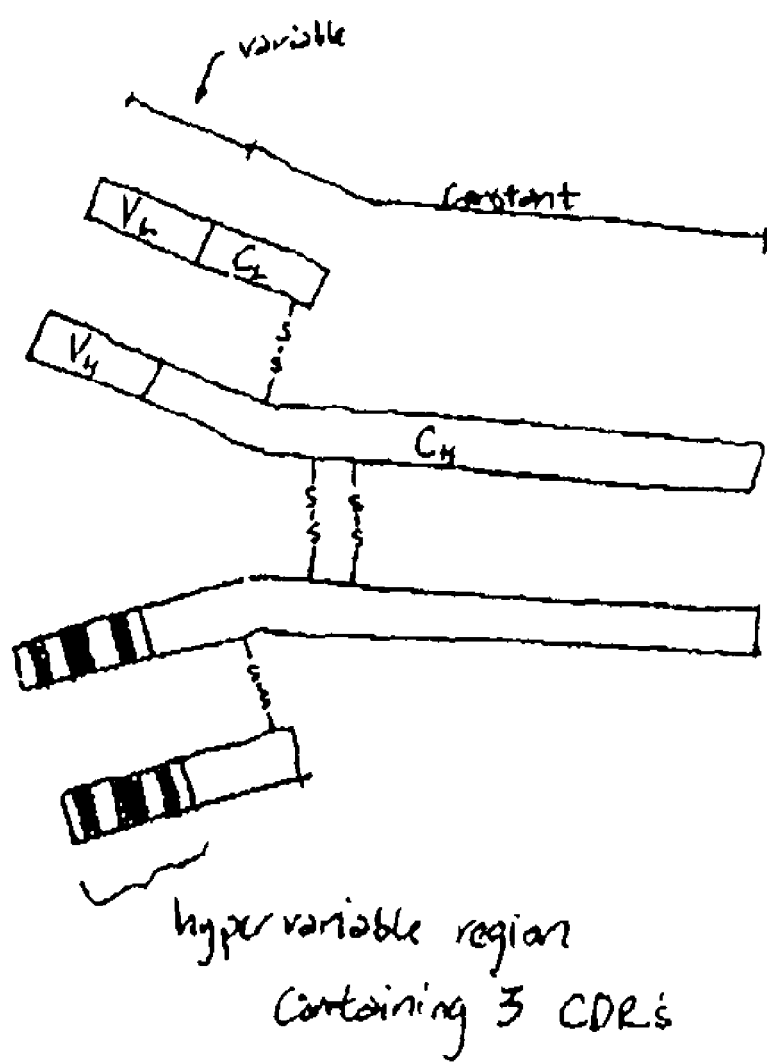
FIG. 2 depicts antibody regions, including the heavy chain constant region ($C_H$), the heavy chain variable region ($V_H$), the light chain constant region ($C_L$), and the light chain variable region ($V_L$). The complementarity determining regions (CDRs) within the variable regions are shown as black bars.

The term "antibody", as used herein, includes full-length antibodies and portions thereof. A full-length antibody has one pair or, more commonly, two pairs of polypeptide chains, each pair comprising a light and a heavy chain. Each heavy or light chain is divided into two regions, the variable region (which confers antigen recognition and binding) and the constant region (associated with localization and cellular interactions). Thus, a full-length antibody commonly contains two heavy chain constant regions ($H_c$ or $C_H$), two heavy chain variable regions ($H_v$ or $V_H$), two light chain constant regions (Lc or C[), and two light chain variable regions ($L_v$ or $V_L$) (FIG. 2). The light chains or chain, may be either a lambda or a kappa chain. Thus, in an embodiment of the invention, the antibodies include at least one heavy chain variable region and one light chain variable region, such that the antibody binds antigen.

Another aspect of the invention involves the variable region that comprises alternating complementarity determining regions, or CDRs, and framework regions, or FRs. The CDRs are the sequences within the variable region that generally confer antigen specificity.

The invention also encompasses portions of antibodies that comprise sufficient variable region sequence to confer antigen binding. Portions of antibodies include, but are not limited to Fab, Fab', F(ab')$_2$, Fv, SFv, scFv (single-chain Fv), whether produced by proteolytic cleavage of intact antibodies, such as papain or pepsin cleavage, or by recombinant methods, in which the cDNAs for the intact heavy and light chains are manipulated to produce fragments of the heavy and light chains, either separately, or as part of the same polypeptide.

MAbs within the scope of the invention include sequences corresponding to human antibodies, animal antibodies, and combinations thereof. The term "chimeric antibody," as used herein, includes antibodies that have variable regions derived from an animal antibody, such as a rat or mouse antibody, fused to another molecule, for example, the constant domains derived from a human antibody. One type of chimeric antibodies, "humanized antibodies", have had the variable regions altered (through mutagenesis or CDR grafting) to match (as much as possible) the known sequence of human variable regions. CDR grafting involves grafting the CDRs from an antibody with desired specificity onto the FRs of a human antibody, thereby replacing much of the non-human sequence with human sequence. Humanized antibodies, therefore, more closely match (in amino acid sequence) the sequence of known human antibodies. By humanizing mouse monoclonal antibodies, the severity of the human anti-mouse antibody, or HAMA, response is diminished. The invention further includes fully human antibodies which would avoid, as much a possible, the HAMA response.

Modified antibodies include, for example, the proteins or peptides encoded by truncated or modified antibody-encoding genes. Such proteins or peptides may function similarly to the antibodies of the invention. Other modifications, such as the addition of other sequences that may enhance the effector function, which includes the ability to block or alleviate nasal colonization by staphylococci, are also within the present invention. Such modifications include, for example, the addition of amino acids to the antibody's amino acid sequence, deletion of amino acids in the antibody's amino acid sequence, substitution of one or more amino acids in the antibody amino acid sequence with alternate amino acids, isotype switching, and class switching.

In certain embodiments, an antibody may be modified in its Fc region to prevent binding to bacterial proteins. The Fc region normally provides binding sites for neutrophils, macrophages, other accessory cells, complement components, and, receptors of the immune system. As the antibodies bind to bacteria and opsonize them, accessory cells recognize the coated bacteria and respond to infection. When a bacterial protein binds to the Fc region near the places where accessory cells bind, the normal function of these cells is inhibited. For example, Protein A, a bacterial protein found in the cell membrane of S. aureus, binds to the Fc region of IgG near accessory cell binding sites. In doing so, Protein A inhibits the function of these accessory cells, thus interfering with clearance of the bacterium. To circumvent this interference with the antibacterial immune response, the Fc portion of the antibody of the invention may be modified to prevent nonspecific binding of Protein A while retaining binding to accessory cells (15).

In light of these various forms, the antibodies of the invention include clones of full length antibodies, antibody portions, chimeric antibodies, humanized antibodies, fully human antibodies, and modified antibodies. Collectively, these will be referred to as "MAbs" or monoclonal antibodies unless otherwise indicated.

The term "epitope", as used herein, refers to a region, or regions, of LTA that is bound by an antibody to LTA. The regions that are bound may or may not represent a contiguous portion of the molecule.

The term "antigen", as used herein, refers to a polypeptide sequence, a non-proteinaceous molecule, or any molecule that can be recognized by the immune system. An antigen may be a full-sized staphylococcal protein or molecule, or a fragment thereof, wherein the fragment is either produced from a recombinant cDNA encoding less than the full-length protein or derived from the full-sized molecule or protein. Such fragments may be produced via enzymatic processing, such as proteolysis. An antigen may also be a polypeptide sequence that encompasses an epitope of a staphylococcal protein, wherein the epitope may not be contiguous with the linear polypeptide sequence of the protein. The DNA sequence encoding an antigen may be identified, isolated, cloned, and transferred to a prokaryotic or eukaryotic cell for expression by procedures well-known in the art (25).

An antigen, or epitope thereof, may be 100% identical to a region of the staphylococcal molecule or protein amino acid sequence, or it may be at least 95% identical, or at least 90% identical, or at least 85% identical. An antigen may also have less than 95%, 90% or 85% identity with the staphylococcal molecule or protein amino acid sequence, provided that it still be able to elicit antibodies the bind to a native staphylococcal molecule or protein. The percent identity of a peptide antigen can be determined, for example, by comparing the sequence of the target antigen or epitope to the analogous portion of staphylococcal sequence using the GAP computer program, version 6.0 described by Devereux et al. (Nucl. Acids Res. 12:387, 1984) and available from the University of Wisconsin Genetics Computer Group (UWGCG). The GAP program utilizes the alignment method of Needleman and Wunsch (J. Mol. Biol. 48:443, 1970), as revised by Smith and Waterman (Adv. Appl. Math 2:482, 1981), and is applicable to determining the percent identity of protein or nucleotide sequences referenced herein. The preferred default parameters for the GAP program include: (1) a unary comparison matrix (containing a value of 1 for identities and 0 for non-identities) for nucleotides, and the weighted comparison matrix of Gribskov and Burgess, Nucl. Acids Res. 14:6745, 1986, as described by Schwartz and Dayhoff, eds., Atlas of Protein Sequence and Structure, National Biomedical Research Foundation, pp. 353-358, 1979; (2) a penalty of 3.0 for each gap and an additional 0.10 penalty for each symbol in each gap; and (3) no penalty for end gaps.

Alternatively, for simple comparisons over short regions up to 10 or 20 units, or regions of relatively high homology, for example between antibody sequences, the percent identity over a defined region of peptide or nucleotide sequence may by determined by dividing the number of matching amino acids or nucleotides by the total length of the aligned sequences, multiplied by 100%. Where an insertion or gap of one, two, or three amino acids occurs in a MAb chain, for example in or abutting a CDR, the insertion or gap is counted as single amino acid mismatch.

Antigens may be surface antigens and/or virulence antigens and/or adherence antigens. Surface antigens are antigens that are accessible to an antibody when the antigen is in the configuration of the whole intact bacterium, i.e., the antigen is not inside the cell cytoplasm. Virulence antigens are antigens that are involved in the pathogenic process, causing disease in a host. Virulence antigens include, for example, LTA, peptidoglycan, toxins, fimbria, flagella, and adherence antigens. Adherence antigens mediate the ability of a staphylococcal bacterium to adhere to an epithelial surface, such as the epithelial surface of the anterior nares. An antigen may be a non-proteinaceous component of staphylococci such as a carbohydrate or lipid. For example, peptidoglycan and lipoteichoic acid are two non-proteinaceous antigens found in the cell wall of staphylococci. Antigens may comprise or include fragments of non-proteinaceous molecules as long as they elicit an immune response.

As used herein, antigens include molecules that can elicit an antibody response to LTA. An antigen may be LTA itself, or a fragment or portion thereof. An antigen may also be an unrelated molecule, which, through some structural similarity, is able to elicit antibodies that bind to LTA. Binding to LTA may thus be assessed by binding to such peptide epitope mimics, as described, for example, in U.S. Patent Application Publication No. 2002/0082395, which is incorporated herein by reference. In certain embodiments of the invention, an antigen elicits antibodies that bind to LTA on the surface of bacteria.

As specifically used herein, an antigen is any molecule that can specifically bind to an antibody, including antibodies specific for LTA. Antigens of the invention thus include antigens that bind to any of monoclonal antibodies MAb-391.4, M110, M120, A110, A120, A120a, and A120b, described herein.

An antibody is said to specifically bind to an antigen, epitope, or protein, if the antibody gives a signal by an assay such as an ELISA assay that is at least two fold, at least three fold, at least five fold, or at least ten fold greater than the background signal, i.e., at least two fold, at least three fold, at least five fold, or at least ten fold greater than the signal ascribed to non-specific binding. An antibody is said to specifically bind to a bacterium if the antibody gives a signal by MeOH-fixed bacteria ELISA or live bacteria ELISA, or other assay, that is at least 1.5 fold, 2 fold, or 3 fold greater than the background signal.

"Enhanced phagocytosis", as used herein, means an increase in phagocytosis over a background level as assayed by the methods in this application, or another comparable assay. The level deemed valuable may well vary depending on the specific circumstances of the infection, including the type of bacteria and the severity of the infection. For example, for enhanced phagocytic activity, in one embodiment, an enhanced response is equal to or greater than 75% over background phagocytosis. In another embodiment, an enhanced response is equal to or greater than 80% or 85% over background phagocytosis. In another embodiment, an enhanced response is equal to or greater than 90% or 95% over background phagocytosis. Enhanced phagocytosis may also be equal to or greater than 50%, 55%, 60%, 65%, or 70% over background phagocytosis. In another embodiment, enhanced phagocytosis comprises a statistically significant increase in phagocytic activity as compared to background phagocytosis or phagocytosis with a non-specific or non-opsonic control antibody.

The specific determination or identification of a "statistically significant" result will depend on the exact statistical test used. One of ordinary skill in the art can readily recognize a statistically significant result in the context of any statistical test employed, as determined by the parameters of the test itself. Examples of these well-known statistical tests include, but are not limited to, $X^2$ Test (Chi-Squared Test), Students t Test, F Test, M test, Fisher Exact Text, Binomial Exact Test, Poisson Exact Test one way or two way repeated measures analysis of variance, and calculation of correlation efficient (Pearson and Spearman).

A MAb has "opsonic activity" if it can bind to an antigen to promote attachment of the antigen to the phagocyte and thereby enhance phagocytosis. As used herein, opsonic activity may also be assessed by assays that measure neutrophil mediated opsonophagocytotic bactericidal activity.

The MAb's of the invention are useful for the treatment of systemic and local staphylococcal infections. As used herein, "treatment" encompasses any reduction, amelioration, or "alleviation" of existing infection as well as "blocking" or prophylaxis against future infection. In this respect, treatment with a MAb of the invention is said to "alleviate" staphylococcal nasal colonization if it is able to decrease the number of colonies in the nares of a mammal when the MAb is administered before, concurrently with, or after exposure to staphylococci, whether that exposure results from the intentional instillation of *staphylococcus* or from general exposure. For instance, in the nasal colonization animal model described below, a MAb or collection of MAbs is considered to alleviate colonization if the extent of colonization, or the number of bacterial colonies that can be grown from a sample of nasal tissue, is decreased after administering the MAb or collection of MAbs. A MAb or collection of MAbs alleviates colonization in the nasal colonization assays described herein when it reduces the number of colonies by at least 50%, at least 60%, at least 75%, at least 80%, or at least 90%. 100% alleviation may also be referred to as eradication.

A MAb is said to "block" staphylococcal colonization if it is able to prevent the nasal colonization of a human or non-human mammal when it is administered prior to, or concurrently with, exposure to staphylococci, whether by intentional instillation or otherwise into the nares. A MAb blocks colonization, as in the nasal colonization assay described herein, if no staphylococcal colonies can be grown from a sample of nasal tissue taken from a mammal treated with the MAb of the invention for an extended period such as 12 hours or longer or 24 hours or longer compared to control mammals. A MAb also blocks colonization in the nasal colonization assay described herein if it causes a reduction in the number of animals that are colonized relative to control animals. For instance, a MAb is considered to block colonization if the number of animals that are colonized after administering the material and the Gram-positive bacteria is reduced by at least 25%, at least 50%, and at least 75%, relative to control animals or if no colonies can be grown from a sample taken from a treated individual for an extended period such as 12 hours or 24 hours or longer.

In a clinical setting, the presence or absence of nasal colonization in a human patient is determined by culturing nasal swabs on an appropriate bacterial medium. These cultures are scored for the presence or absence of staphylococcal colonies. In this type of qualitative assay system, it may be difficult to distinguish between blocking and alleviation of staphylococcal colonization. Thus, for the purposes of qualitative assays, such as nasal swabs, a MAb "blocks" colonization if it prevents future colonization in human patients who show no signs of prior colonization for an extended period of 12 or 24 hours or longer. A MAb "alleviates" colonization if it causes a discernable decrease in the number of positive cultures taken from a human patient who is already positive for staphylococci before the MAbs of the invention are administered.

A vaccine is considered to confer a protective immune response if it stimulates the production of opsonic antibodies to gram-positive bacteria. Production of opsonic antibodies may be measured by the presence of such antibodies in the serum of a test subject that has been administered the vaccine, relative to a control that has not received the vaccine. The presence of opsonic antibodies in the serum may be measured by the activity assays described herein, or by other equivalent assays. If an opsonophagocytic bactericidal assay is used, then killing by the test serum of at least 50% more bacteria, 75% more bacteria, and at least 100% more bacteria, relative to the control serum, is considered to be enhanced immunity.

DETAILED DESCRIPTION OF THE INVENTION

The present invention provides murine antibodies, including monoclonal antibodies, and chimeric, humanized and fully human antibodies, fragments, derivatives, and regions thereof, which bind to lipoteichoic acid (LTA) of Gram positive staphylococci. Gram positive bacteria, unlike Gram negative bacteria, take up the Gram stain as a result of a difference in the structure of the cell wall. The cell walls of Gram negative bacteria are made up of a unique outer membrane of two opposing phospholipid-protein leaflets, with an ordinary phospholipid in the inner leaflet but the extremely toxic lipopolysaccharide in the outer leaflet. The cell walls of Gram positive bacteria seem much simpler in comparison, containing two major components, peptidoglycan and teichoic acids plus additional carbohydrates and proteins depending on the species.

Moreover, because the basis of the binding to Gram positive bacteria is the presence of LTA and because LTA is a major component of the cell walls of Gram positive bacteria and is highly conserved, the antibodies of the claimed invention are broadly reactive against Gram positive bacteria. This broad reactivity permits the antibodies of the invention to block the binding of Gram positive bacteria to epithelial cells, such as human epithelial cells (50-54). Finally, these antibodies exhibit broad opsonic activity and consequently enhance phagocytosis and killing of Gram positive bacteria. Accordingly, the invention provides broadly reactive, opsonic, and protective antibodies for the diagnosis, prevention, and/or treatment of bacterial infections caused by Gram positive bacteria.

Among the Gram positive Staphylococci against which the antibodies of the invention are directed are *S. aureus* (a coagulase positive bacteria) and *S. epidermidis* (a coagulase negative bacteria).

Three of the monoclonal antibodies of the invention (M110, M120, and MAb-391.4) bind strongly to LTA. M110 and M120 also exhibit high opsonic activity for *S. epidermidis*, while MAb-391.4 is also opsonic for *S. epidermidis*, but less so. M120 is also highly opsonic against *S. aureus*. M110 was derived from mice immunized with whole *S. epidermidis* strain Hay as described in detail in U.S. Pat. No. 6,610,293, which is incorporated herein by reference. In screening for hybridomas, the antibodies of one clone (hybridoma line 96-105CE11 IF6, which produces antibody M110) were found to bind very strongly to Gram positive bacteria such as strain Hay, all three serotypes of *S. epidermidis*, *S. hemolyticus*, *S. hominus*, and two serotypes of *S. aureus*, but not to the Gram negative control, *Haemophilus influenza* (see U.S. Pat. No. 6,610,293).

M120 was derived from mice immunized with conjugates of *S. aureus* LTA. The antibodies of one clone (00-107GG12 ID 12, which produces antibody M120) were found to bind strongly to LTA, and were opsonic for *S. aureus* type 5 and *S. epidermidis* strain Hay.

MAb-391.4 is from QED Biosciences, and was derived from mice immunized with whole UV-killed *S. aureus*.

The variable regions of M110, M120, and 391.4 were sequenced and compared, revealing a surprising 88% identity (203/230) at the amino acid level. Further, the level of identity was found to be 96% (220/230) between the antibodies that are highly opsonic for *S. epidermidis*, M110 and M120. We believe that this level of homology between three monoclonal antibodies that were raised in three different mice, using three different antigen preparations from two different types of bacteria, is unprecedented. To understand how unexpected this finding is, one need only consider how vast and diverse is the collection of antibodies in the immune system.

The immune system is made up of a large number of B cells, each bearing antibodies of a different specificity, but only about 1 in 10,000 to 1 in 1,000,000 B cells is specific for a particular antigen. When a foreign antigen, such as is found on the surface of a bacteria, enters the blood stream, the appropriate B cell recognizes that antigen and then enters a lymph node where it undergoes rapid division to produce many progeny bearing the identical specificity. However, the rapidly dividing B cells also undergo somatic hypermutation. Somatic hypermutation results in about half of the B cells acquiring mutations in their rearranged heavy and light chain genes, with mutation occurring preferentially in complementarity determining regions (CDRs) of the variable regions. Mutated B cells that retain their ability to bind antigen continue to secrete antibody, while those that no longer bind antigen undergo apoptosis. As the antigen is cleared from the host, only B cells that have very high antigen affinity survive in a process called affinity maturation. The surviving activated B cells differentiate into plasma cells, which are short-lived and secrete antibody, and memory B cells, which are long-lived lymphocytes bearing membrane-bound antibody that can be rapidly stimulated when the antigen is re-introduced.

The processes of somatic hypermutation and affinity maturation result in progeny B cells that are of higher affinity and have immunoglobulins of different amino acid sequence than the original activated B cell. Therefore, a single B cell that is activated by a foreign antigen can produce many progeny of differing affinity and immunoglobulin amino acid sequence.

Because of these processes, it is generally believed that two animals immunized with the same antigen will produce vastly different antibody repertoires. Nickerson and colleagues demonstrated this concept when they showed that a mouse monoclonal antibody and a human monoclonal antibody that showed nearly identical binding to the same blood group A antigen shared only 15% and 37% identity in their heavy and light chain CDRs (55). X-ray crystallography studies of two antibodies that both bind to hemagglutinin of influenza virus, reveal that, although they share only 56% sequence identity, they both bind with similar affinities and in the same orientation to the same epitope (56).

It has been postulated that the immune system has evolved to provide a maximum range of antigen specificities and redundancy, rather than to bind to specific antigens (55). It follows, therefore, that antibodies derived from the same mouse may be of high specificity, but low homology, because any number of progenitor B cells may be specific for the immunized antigen. Amplification and somatic mutation of those progenitors may, however, result in groups of antibodies that are of higher homology within the group, although they are of very low homology between groups. Antibodies raised against the same immunogen in two or more different mice will necessarily be even less homologous, because they do not share progenitor B cells.

Three specific antibodies of the present invention, M110, M120, and MAb-391.4, were not only raised in different mice, but with different immunogens: M110 was raised to whole *S. epidermidis*, M120 was raised to purified and conjugated *S. aureus* LTA, and MAb-391.4 was raised to whole UV-killed *S. aureus*. Yet, though these antibodies were raised against different immunogen preparations in different mice, they share 88% identity at the amino acid level in both the heavy and light chain variable regions. This high degree of homology suggests that LTA contains a highly antigenic, and highly conserved, epitope which is bound by the three antibodies in a very similar manner. This epitope and mode of binding may be responsible for the high opsonic activity of the monoclonal antibodies.

MAb-391.4 and human/mouse chimeric antibodies of M110 and M120, designated A110 and A120, respectively, were tested for opsonic activity. MAb-391.4, A110, and A120 each demonstrated a high level of opsonic activity against S. epidermidis strain Hay. (see also U.S. Pat. No. 6,610,293).

MAb A110 is currently being manufactured under GMP conditions in preparation for clinical trials. Additional disclosure regarding the MAb A110 is provided in U.S. Provisional Application Ser. No. 60/341,806, now expired, and in related application Methods for Blocking or Alleviating Staphylococcal Nasal Colonizaton by Intranasal Application of Monoclonal Antibodies, filed concurrently herewith, both of which are expressly incorporated by reference.

Thus, one aspect of the invention relates to antibodies that bind to the LTA of Gram positive bacteria, including both coagulase negative (S. epidermidis) and coagulase positive (S. aureus) bacteria, and that enhance the opsonization of such bacteria. These anti-LTA antibodies include monoclonal antibodies, such as M110, M120, and MAb-391.4, chimeric monoclonal antibodies A110, A120, A120a, and A120b, and other monoclonal antibodies including, chimeric, humanized, fully human antibodies, antibody fragments, and modified antibodies.

In a one aspect of the invention, as noted above, the antibody is a chimeric mouse/human antibody made up of regions from the anti-LTA antibodies of the invention together with regions of human antibodies. Chimeric or other monoclonal antibodies are advantageous in that they avoid the development of anti-murine antibodies. In at least one study, patients administered murine anti-TNF (tumor necrosis factor) monoclonal antibodies developed anti-murine antibody responses to the administered antibody (5). This type of immune response to the treatment regimen, commonly referred to as the human anti-mouse antibody response, or the HAMA response, decreases the effectiveness of the treatment and may even render the treatment completely ineffective. Humanized or chimeric human/mouse monoclonal antibodies have been shown to significantly decrease the HAMA response and to increase the therapeutic effectiveness (19).

Thus, in one aspect of the invention, a chimeric heavy chain can comprise the antigen binding region of the heavy chain variable region of the anti-LTA antibody of the invention linked to at least a portion of a human heavy chain IgG, IgA, IgM, or IgD constant region. This humanized or chimeric heavy chain may be combined with a chimeric light chain that comprises the antigen binding region of the light chain variable region of the anti-LTA antibody linked to at least a portion of the human light chain kappa or lambda constant region. Exemplary embodiments include, but are not limited to, an antibody having a mouse heavy chain variable region fused to a human $1gG_1$ constant region, and a mouse light chain variable region fused to a human kappa light chain constant region.

The chimeric antibodies and other MAb's of the invention may be monovalent, divalent, or polyvalent immunoglobulins. For example, a monovalent chimeric antibody is a dimer (HL) formed by a chimeric H chain associated through disulfide bridges with a chimeric L chain, as noted above. A divalent chimeric antibody is a tetramer ($H2 L_2$) formed by two HL dimers associated through at least one disulfide bridge. A polyvalent or multivalent chimeric antibody may be based on an aggregation of chains, with or without a carrier or scaffold.

The MAbs of the invention include antibodies that contain heavy and light chain variable regions derived from two different antibodies. In one embodiment, the heavy and light chain variable regions are derived from two antibodies that bind to the same molecule, e.g. LTA. Exemplary embodiments include A120a, which is a human/mouse chimeric antibody that has a heavy chain variable region from A110 and a light chain variable region from A120; and A120b, which is a human/mouse chimeric antibody that has a heavy chain variable region from A120 and a light chain variable region from A110. Additional exemplary embodiments include antibodies that comprise a heavy chain variable region from MAb-391.4, and a light chain variable region from either of A110 or A120, and antibodies that comprise a light chain variable region from MAb-391.4, and a heavy chain variable region from either of A110 or A120.

In yet another aspect, the invention is a collection of opsonic monoclonal antibodies that bind to LTA and that exhibit a high degree of homology in the variable regions at either the amino acid or nucleic acid level, or both. In one embodiment, this collection comprises one or more of M110, M120, their human/mouse chimeric counterparts, A110, A120, and MAb-391.4. In one aspect, the amino acid sequences of the variable regions are at least 75% identical, at least 80% identical, at least 85% identical, at least 88% identical, at least 90% identical, or at least 95% identical as defined above.

In addition to the antibodies, the present invention also encompasses the DNA sequences of the genes coding for the antibodies (see, e.g., FIGS. 5, 6, and 9; SEQ ID NOs: 11, 13-15, 19, and 20) as well as the polypeptides encoded by the DNA (see, e.g., FIGS. 5, 6, and 10; SEQ ID NOs: 10, 12, 16, 17, 21, and 22). Those figures provide the variable regions of the heavy and light chains of A110, A120, and MAb-391.4, including the complementarity determining regions (CDRs), the hypervariable amino acid sequences within antibody variable regions that usually interact with the antigen. As noted above, the DNA and amino acid sequence homology between A110 and A120 is striking. There is a 94% homology (216/229) at the amino acid level and a 96% homology (662/687) at the DNA level between the antibodies. This suggests that these antibodies share a sequence and structural similarity.

The invention includes peptide sequences for, and DNA sequences encoding, full-length antibodies and portions thereof, as well as CDRs and FRs relating to these MAbs. The invention further includes DNA and peptide sequences that are homologous to these sequences. In one embodiment, these homologous DNAs and peptide sequences are about 70% identical, although other embodiments include sequences that are about 75%, 80%, 85%, 88%, 90%, and 95% or more identical. As indicated above, determining levels of identity for both the DNA and peptide sequence is well within the routine skill of those in the art.

As shown in FIG. 10A, alignment of the A110, A120, and 391.4 light chain variable regions (Seq. ID Nos. 16, 10, and 21, respectively) shows identical amino acids in 95 of 106 amino acids, or more than 89% identity overall. Within the region spanning the CDRs (amino acids 24 to 96 of the light chain variable regions) the percent identity is about 93% (68 out of 73 amino acids). It is predicted that light chain variable regions with a somewhat lower overall identity would still form MAbs that specifically bind LTA, and are therefore within the scope of the invention. The CDRs themselves show at least 88% identity, in particular, CDR1 (amino acids 24-33), CDR2 (amino acids 49-55), and CDR3 (amino acids 88-96), show 9/10, 7/7, and 8/9 identical amino acids. Likewise, the framework regions (FRs) surrounding the CDRs are also highly conserved: amino acids 1-23 of SEQ ID Nos. 16, 10, and 21 show greater than 86% identity (20/23 matching amino acids); amino acids 34-48 show about 93% identity (14/15); amino acids 56-87 show about 93% identity (68/73); and amino acids 97-106 show 70% identity.

Similarly, in FIG. 10B, alignment of the A110, A120, and 391.4 heavy chain variable regions (Seq. ID Nos. 17, 12, and 22, respectively) also shows a high degree of sequence identity. Counting single amino acid gaps and insertions as single-point mismatches, Seq. ID Nos. 17, 12, and 22 show 86% identity overall (108/125 identical amino acids). It is predicted that heavy chain variable regions with a somewhat lower overall identity would still form MAbs that specifically bind LTA, and are therefore within the scope of the invention. The degree of identity is particularly high in the FR region preceding CDR1 through the FR region preceding CDR3, in particular, the 96 base region from amino acid 16 to 101 of Seq. ID Nos. 17, 12, and 22 shows 8 mismatches or approximately 91% identity. CDR1, itself, shows 90% identity over 10 amino acids (amino acids 26-35), and CDR2 (amino acids 50-69) shows about 89% identity over 19 amino acids. The framework regions surrounding the CDRs are also highly conserved. Amino acids 1-25 of SEQ ID Nos. 17, 12, and 22 show 92% identity (23/25 matching amino acids); amino acids 36-49 show 100% identity over 14 amino acids; the FR region between CDR2 and CDR3 (amino acids 70 to about 101) shows about 87% identity (over 31-32 amino acids); and amino acids 115-125 show 90% identity.

Thus, in one aspect, the invention encompasses polypeptides (including regions of larger polypeptides, such as MAbs) that 1) exhibit high sequence homology to Seq. ID Nos. 10, 12, 16, 17, 21, or 22, or defined regions thereof, and 2) are capable of functioning as all or part of the variable region of a MAb that specifically binds LTA. In one embodiment, such polypeptides comprise, or are at least 70%, 75%, 77% 80%, 85%, 86%, 87%, 88%, 89%, 90%, 91%, 93%, 95% identical to, any of Seq. ID Nos. 10, 12, 16, 17, 21, or 22. Conversely, polypeptides within the scope of the invention may be less than 100%, 99%, 95%, 90%, 80% or less identical to Seq. ID Nos. 10, 12, 16, 17, 21, or 22 provided that they are capable of functioning as all or part of the variable region of a MAb that specifically binds to LTA.

In another embodiment, polypeptides within the scope of the invention comprise, or are at least 70%, 75%, 77%, 80%, 85%, 86%, 87%, 88%, 89%, 90%, 91%, 93%, 95% identical to, amino acids 24 to 96 of any of Seq. ID Nos. 10, 16, or 21. In another embodiment, such polypeptides comprise, or are at least 70%, 75%, 77%, 80%, 85%, 86%, 87%, 88%, 89%, 90%, 91%, 93%, 95% identical to, 1) amino acids 24-33, 49-55, and 88-73 of Seq. ID Nos. 10, 16, or 21, or 2) amino acids 26-35 or 50-69 of Seq. ID Nos. 12, 17, or 22; and are capable of functioning as a CDR, or portion thereof, in a MAb that specifically binds to LTA. In another embodiment, such polypeptides comprise, or are at least 70%, 75%, 77%, 80%, 81%, 82%, 85%, 86%, 87%, 88%, 89%, 90%, 91%, 93%, 95% identical to, 1) amino acids 1-23, 34-48, 56-87, and 97-106 of Seq. ID Nos. 10, 12, 16, 17, 21, or 22, or 2) amino acids 1-25, 36-49, 70-101, or 115-125 of Seq. ID Nos. 12, 17, or 22; and are capable of functioning as a framework region, or portion thereof, in a MAb that specifically binds to LTA.

The invention further comprises collections of a multiplicity of any of the above sequences capable of functioning as all or part of the variable region of a MAb that specifically binds to LTA, as part of a larger polypeptide, MAb, collection of MAbs or aggregation of MAbs; and the use thereof in prophylaxis, treatment, and for the production of pharmaceutical compounds or medicaments. The invention further comprises any non-naturally occurring RNA, DNA, or vector thereof, encoding any of the above sequences capable of functioning as all or part of the variable region of a MAb that specifically binds to LTA, as well as plasmids, viruses, bacteria, yeast, microorganisms, cell lines, transgenic plants or animals harboring or expressing such nucleic acids. Thus, the invention contemplates production systems for Mabs, light chains, heavy chains, and portions thereof, comprising 1) a cell (including bacteria, yeast, microorganisms, eukaryotic cell lines, transgenic plant or animal) in connection with 2) at least one recombinant nucleic acid capable of directing the expression of any of the Mabs or related polypeptides of the invention.

The invention thus further comprises a general method of identifying highly antigenic and highly conserved epitopes by raising antibodies against different immunogen preparations in different mice, sequencing the variable regions of the antibodies, comparing the variable regions, and identifying antibodies that share a high degree of homology in the variable regions.

The DNA sequences of the invention can be identified, isolated, cloned, and transferred to a prokaryotic or eukaryotic cell for expression by procedures well-known in the art. Such procedures are generally described in *Molecular Cloning: A Laboratory Manual*, as well as *Current Protocols in Molecular Biology* (44, 45), which are incorporated by reference. Guidance relating more specifically to the manipulation of sequences of the invention may be found in *Antibody Engineering*, and *Antibodies: A Laboratory Manual* (64, 65), both of which are incorporated by reference in their entirety. In certain embodiments, a CDR can be grafted onto any human antibody framework region using techniques standard in the art, in such a manner that the CDR maintains the same binding specificity as in the intact antibody. As noted as above, an antibody that has its CDRs grafted onto a human framework region is said to be "humanized". Humanized, and fully human antibodies generally also include human constant regions, thus maximizing the percentage of the antibody that is human-derived, and potentially minimizing the HAMA response.

In addition, the DNA and peptide sequences of the antibodies of the invention, including both monoclonal and chimeric antibodies, humanized and fully human antibodies, may form the basis of antibody "derivatives," which include, for example, the proteins or peptides encoded by truncated or modified genes. Such proteins or peptides may function similarly to the antibodies of the invention. Other modifications, such as the addition of other sequences that may enhance the effector function, which includes phagocytosis and/or killing of the bacteria, are also within the present invention.

The present invention also discloses a pharmaceutical composition comprising the antibodies, whether monoclonal or chimeric, humanized, or fully human, together with a pharmaceutically acceptable carrier. The pharmaceutical compositions of the invention may alternatively comprise the isolated antigen, epitope, or portions thereof, together with a pharmaceutically acceptable carrier.

Pharmaceutically acceptable carriers can be sterile liquids, such as water, oils, including petroleum oil, animal oil, vegetable oil, peanut oil, soybean oil, mineral oil, sesame oil, and the like. Saline solutions, aqueous dextrose, and glycerol solutions can also be employed as liquid carriers, particularly for injectable solutions. Suitable pharmaceutical carriers are described in *Remington's Pharmaceutical Sciences, 18th Edition* (13), which is herein incorporated by reference.

Additionally, the invention may be practiced with various delivery vehicles and/or carriers. Such vehicles may increase the half-life of the MAbs in storage and upon administration including, but not limited to, application to skin, wounds, eyes, lungs, or mucus membranes of the nasal or gastrointestinal tract, or upon inhalation or instillation into the nares. These carriers comprise natural polymers, semi-synthetic polymers, synthetic polymers, lipososmes, and semi-solid dosage forms (21, 29, 33, 35, 36, 46). Natural polymers include, for example, proteins and polysaccharides. Semi-synthetic polymers are modified natural polymers such as chitosan, which is the deacetylated form of the natural polysaccharide, chitin. Synthetic polymers include, for example, polyphosphoesters, polyethylene glycol, poly (lactic acid), polystyrene sulfonate, and poly (lactide coglycolide). Semi-solid dosage forms include, for example, dendrimers, creams, ointments, gels, and lotions. These carriers can also be used to microencapsulate the MAbs or be covalently linked to the MAbs.

Finally, the present invention provides methods for treating a patient infected with, or suspected of being infected with, a Gram-positive bacteria such as a staphylococcal organism. The method comprises administering a therapeutically effective amount of a pharmaceutical composition comprising the anti-LTA immunoglobulin (whether monoclonal, chimeric, humanized, or fully human, including fragments, regions, and derivatives thereof) and a pharmaceutically acceptable carrier. A patient can be any human or non-human mammal in need of prophylaxis or other treatment. Representative patients include any mammal subject to *S. aureus* or other staphylococcal or Gram-positive infection or carriage, including humans and non-human animals such as mice, rats, rabbits, dogs, cats, pigs, sheep, goats, horses, primates, ruminants including beef and milk cattle, buffalo, camels, as well as fur-bearing animals, herd animals, laboratory, zoo, and farm animals, kenneled and stabled animals, domestic pets, and veterinary animals.

A therapeutically effective amount is an amount reasonably believed to provide some measure of relief, assistance, prophylaxis, or preventative effect in the treatment of the infection. A therapeutically effective amount may be an amount believed to be sufficient to block a bacterial infection. Similarly, a therapeutically effective amount may be an amount believed to be sufficient to alleviate a bacterial infection. Such therapy as above or as described below may be primary or supplemental to additional treatment, such as antibiotic therapy, for a staphylococcal infection, an infection caused by a different agent, or an unrelated disease. Indeed, combination therapy with other antibodies is expressly contemplated within the invention.

A further embodiment of the present invention is a method of preventing such infections, comprising administering a prophylactically effective amount of a pharmaceutical composition comprising the anti-LTA antibody (whether monoclonal, chimeric, humanized, or fully human) and a pharmaceutically acceptable carrier.

A prophylactically effective amount is an amount reasonably believed to provide some measure of prevention of infection by Gram positive bacteria. Such therapy as above or as described below may be primary or supplemental to additional treatment, such as antibiotic therapy, for a staphylococcal infection, an infection caused by a different agent, or an unrelated disease. Indeed, combination therapy with other antibodies is expressly contemplated within the invention.

The antibodies and the pharmaceutical compositions of the invention may be administered by intravenous, intraperitoneal, intracorporeal injection, intra-articular, intraventricular, intrathecal, intramuscular or subcutaneous injection, or intranasally, dermally, intradermally, intravaginally, orally, or by any other effective method of administration. The composition may also be given locally, such as by injection to the particular area infected, either intramuscularly or subcutaneously. Administration can comprise administering the pharmaceutical composition by swabbing, immersing, soaking, or wiping directly to a patient. The treatment can also be applied to objects to be placed within a patient, such as dwelling catheters, cardiac valves, cerebrospinal fluid shunts, joint prostheses, other implants into the body, or any other objects, instruments, or appliances at risk of becoming infected with a Gram positive bacteria, or at risk of introducing such an infection into a patient.

As a particularly valuable corollary of treatment with the compositions of the invention (pharmaceutical compositions comprising anti-LTA antibodies, whether, monoclonal, chimeric, humanized or fully human) may be the reduction in cytokine release that results from the introduction of the LTA of a Gram positive bacteria (49). As is now recognized in the art, LTA induces cytokines, including, for example, tumor necrosis factor alpha, interleukin 6, and interferon gamma (see, e.g., (37)). Accordingly, the compositions of the invention may enhance protection at three levels: (1) by binding to LTA on the bacteria and thereby blocking the initial binding to epithelial cells and preventing subsequent invasion of the bacteria; (2) by binding to LTA on bacteria and thereby enhancing opsonization of the bacteria and clearance of the bacteria from tissues and/or blood; and/or (3) by binding to LTA and partially or fully blocking cytokine release and modulating the inflammatory responses to prevent shock and tissue destruction.

Having generally described the invention, it is clear that the invention overcomes some of the potentially serious problems described in the Background section regarding the development of antibiotic resistant Gram positive bacteria. As set forth above, Staphylococci and Streptococci (such as *S. faecalis*) have become increasingly resistant to antibiotics and, with the recent spread of vancomycin resistant strains, antibiotic therapy may become totally ineffective.

Particular aspects of the invention are now presented in the form of the following Materials and Methods, as well as the specific Examples. Of course, these are included only for purposes of illustration and are not intended to be limiting of the present invention.

Materials and Methods

Bacteria

*S. aureus*, type 5, is deposited at the ATCC under Accession No. 49521.

*S. epidermidis*, strain Hay, was deposited at the ATCC on Dec. 19, 1990 under Accession No. 55133.

Hybridoma

Hybridoma 96-105CE11 IF6 (M110) was deposited at the American Type Culture Collection (ATCC), located at P.O. Box 1549, Manassas, Va. 20108, U.S.A., on Jun. 13, 1997, under ATCC Accession No. HB-12368.

Hybridoma 00-107GG12 ID12 (M120) was deposited at the American Type Culture Collection (ATCC), located at P.O. Box 1549, Manassas, Va. 20108, U.S.A., on Aug. 16, 2001, under ATCC Accession No. PTA-3644.

Hybridoma 391.4 was deposited at the American Type Culture Collection (ATCC), located at P.O. Box 1549, Manassas, Va. 20108, U.S.A., on Dec. 18, 2001, under ATCC Accession No. PTA-3932.

Isotype Determination Assay

Isotype was determined using a mouse immunoglobulin isotype kit obtained from Zymed Laboratories (Cat. No. 90-6550).

Binding Assays

In the binding assays of the invention, immunoglobulin is incubated with a preparation of whole cell staphylococci or with a preparation of bacterial cell wall components such as LTA or PepG. The binding assay may be an agglutination assay, a coagulation assay, a colorimetric assay, a fluorescent binding assay, or any other suitable binding assay that is known in the art. A particularly suitable assay is either an enzyme-linked immunosorbent assay (ELISA) or a radio-immunoassay (RIA). Binding is detected directly and can also be detected indirectly by using competitive or noncompetitive binding procedures known in the art.

The whole cell *staphylococcus* preparation, LTA preparation, PepG preparation, or a combination of those preparations, may be fixed using standard techniques to a suitable solid support, including, but not limited to, a plate, a well, a bead, a micro-bead, a paddle, a propeller, or a stick. Solid supports may be comprised of, for example, glass or plastic. In certain embodiments of the invention, the solid support is a microtiter plate.

Generally, a binding assay requires the following steps. First, the fixed preparation is incubated with an immunoglobulin source. In one embodiment of the assay, the immunoglobulin source is, for example, tissue culture supernatant or a biological sample such as ascites, plasma, serum, whole blood, or body tissue. In another embodiment, the immunoglobulin may be further isolated or purified from its source by means known in the art, and the purified or isolated immunoglobulin is subsequently used in the assay. The amount of binding is determined by comparing the binding in a test sample to the binding in a negative control. A negative control is defined as any sample that does not contain antigen-specific immunoglobulin. In the binding assay, a positive binding reaction results when the amount of binding observed for the test sample is greater than the amount of binding for a negative control. Positive binding may be determined from a single positive/negative binding reaction or from the average of a series of binding reactions. The series of binding reactions may include samples containing a measured amount of immunoglobulin that specifically binds to the fixed antigen, thereby creating a standard curve. This standard curve may be used to quantitate the amount of antigen-specific immunoglobulin in an unknown sample.

In an alternate embodiment of the assay, antibodies are fixed to a solid support and an unknown immunoglobulin sample is characterized by its ability to bind a bacterial preparation. The other aspects of the assays discussed above apply where appropriate.

The specific binding assays used in the Examples are set forth below:

Live Bacteria ELISA (LBE): The LBE assay was performed to measure the ability of antibodies to bind to live bacteria. Various types of bacteria may be used in this assay, including *S. aureus* type 5, type 5-USU, type 8, *S. epidermidis* strain Hay, and *S. hemolyticus*. Bacteria from an overnight plate culture were transferred to 35 mls of Tryptic Soy Broth (TSB) and grown with gentle shaking for 1.5-2.0 hours at 37° C. The bacteria were then pelleted by centrifugation at 1800-2000×g for 15 minutes at room temperature. The supernatant was removed and the bacteria were resuspended in 35-45 mls of phosphate buffered saline containing 0.1% bovine serum albumin (PBS/BSA). The bacteria were again pelleted by centrifugation, the supernatant discarded and the bacteria resuspended in PBS/BSA to a percent transmittance (% T) of 65%-70% at 650 nm. From this suspension the bacteria were further diluted 15-fold in sterile 0.9% sodium chloride (Sigma cat. no. S8776, or equivalent), and 100 µl of this suspension was added to replicate wells of a flat-bottomed, sterile 96-well plate.

Each antibody to be tested was diluted to the desired concentration in PBS/BSA containing 0.05% Tween-20 and horse radish peroxidase-conjugated Protein A (Protein A-HRP, Zymed Laboratories) at a 1:8000 dilution (PBS/BSA/Tween/Prot A-HRP). The Protein A-HRP was allowed to bind to the antibodies for 30-60 minutes at room temperature before use, thereby generating an antibody-Protein A-HRP complex to minimize the potential non-specific binding of the antibodies to the Protein A found on the surface of *S. aureus*. Generally, several dilutions of test antibody were used in each assay. From each antibody dilution, 50 µl of the antibody-Protein A-HRP complex was added to replicate wells and the mixture of bacteria and antibody-Protein A-HRP complex was incubated at 37° C. for 30-60 minutes with gentle rotation (50-75 rpm) on an orbital shaker.

Following the incubation, the bacteria were pelleted in the plate by centrifugation at 1800-2000×g for 10-15 minutes at room temperature. The supernatant was carefully removed from the wells and 200 µl of PBS/BSA containing 0.05% Tween-20 (PBS/BSA/Tween) was added to all wells to dilute unbound reagents. The bacteria were again pelleted by centrifugation and the supernatant was removed. Two hundred µl of PBS/BSA/Tween was again added to all wells and the bacteria were again pelleted by centrifugation as described above. The supernatant was removed and 100 µl of TMB substrate (BioFx, Inc. cat. no. TMBW-0100-01, or equivalent) was added to each well and the hydrolysis of the substrate was allowed to proceed for 15 minutes at room temperature. The reactions were stopped by adding 100 µl of TMB stop reagent (450 nm Stop Reagent; BioFx, Inc. catalog no. STPR-0100-01, or equivalent). The absorbance of each well was determined using a microplate reader fitted with a 450 nm filter.

In this assay, the intensity of the color development was directly proportional to the binding of the antibodies to the bacteria. Control wells contained bacteria and Protein A-HRP without antibody.

Immunoassay on Methanol-Fixed Bacteria: Heat-killed bacteria were suspended in sterile 0.9% sodium chloride (Sigma cat. no. S8776, or equivalent) at a % transmittance (% T) of 70-75% at 650 nm. Ten milliliters the bacterial suspension was diluted 15-fold in sterile 0.9% sodium chloride and then pelleted by centrifugation at 1800×g for 15 minutes at 10-15C. The supernatant was discarded and the pellet was resuspended in 15 milliliters of methanol (MeOH). One hundred microliters of the bacteria-MeOH suspension was distributed into each well of Nunc Maxisorp Stripwells (Nunc catalog no. 469949). The MeOH was allowed to evaporate, fixing the bacteria to the plastic wells. The bacteria-coated stripwells were stored in plastic bags in the dark at room temperature and used within 2 months of preparation.

For evaluation of antibodies, the bacteria-coated plates were washed four times with phosphate buffered saline containing 0.05% Tween-20 (PBS-T) as follows. Approximately 250 microliters of PBS-T was added to each well. The buffer was removed by flicking the plate over the sink and the remaining buffer removed by inverting the plate and tapping it on absorbent paper. The antibody was diluted in PBS-T and then added to the wells. Supernatants, ascites, or purified antibodies were tested at the dilutions indicated in the Examples. Control wells received PBS-T alone. After addition of the antibody, the wells were incubated at room temperature for 30-60 minutes in a draft-free environment. The wells were again washed four times with PBS-T. Ninety-five microliters of detection antibody was then added to each well. The detection antibody was one of the following: rabbit anti-mouse IgG3, rabbit anti-mouse IgM, or goat anti-human IgG (gamma-specific), all conjugated to horse radish peroxidase (HRP) and diluted 1:6000 in PBS-T (Zymed catalog numbers 61-0420, 61-6820 and 62-8420, respectively).

Following another 30-60 minute incubation at room temperature, the wells were washed four times with PBS-T and each well received 100 ul of TMB substrate solution (BioFx #TMBW-0100-01). Plates were incubated in the dark at room temperature for 15 minutes and the binding reactions were stopped by the addition of 100 µl of TMB stop solution (BioFx #STPR-0100-01). The absorbance of each well was measured at 450 nm using a Molecular Devices Vmax plate reader.

Immunoassay with Protein A: In order to evaluate the binding of the MAbs to *S. aureus*, the immunoassay procedure was modified for methanol-fixed bacteria, described above. Because *S. aureus* expresses Protein A on its surface, and Protein A binds strongly to the constant region of the heavy chains of gamma-globulins, it is possible that false positive results may be obtained from non-specific binding of the antibodies to Protein A. To overcome this difficulty, the immunoassay wells were coated with bacteria as described above, but prior to the addition of the antibodies to the bacteria-coated wells, the MAbs were incubated with a solution of recombinant Protein A conjugated to HRP (Zymed Laboratories Cat. No. 10-1123), diluted 1:10,000 in PBS-T. The binding reaction was allowed to proceed for 30 minutes at room temperature. The wells were washed four times with PBS-T and 100 µl of the solution of each Protein A-HRP-MAb combination was added to the wells. The presence of the Protein A-HRP from the pretreatment minimized the binding of the MAbs to the Protein A on the *S. aureus*. Furthermore, the binding of the Protein A-HRP to the constant region of the heavy chain did not interfere with the antibody binding site on the MAbs, thereby allowing evaluation of the MAbs on *S. aureus* and other bacteria.

The Protein A-HRP-MAb solutions were allowed to bind in the coated wells for 30-60 minutes at room temperature. The wells were then washed with PBS-T and TMB substrate solution was added and the assay completed as described above.

Immunoassay on LTA: The binding of the MAbs to LTA was measured by immunoassay on wells coated with *S. aureus* LTA (Sigma Cat. No. 2515). One hundred microliters of a 1 µg/ml LTA solution in PBS was distributed into replicate Nunc Maxisorp Stripwells and incubated overnight at room temperature. The unbound material was removed from the wells by washing four times with PBS-T. Antibody, diluted in PBS-T, was then added to the wells and the assay continued as described above for the Immunoassay on Methanol-Fixed Bacteria.

For immunoassays on PepG, Nunc Maxisorp Stripwell plates were coated with 100 ul of a 5-10 µg/ml solution of PepG (gift of *S. Foster*) in 0.1 M carbonate buffer (pH 9.2-9.6) overnight at room temperature. Unbound antigen was removed from the plate by washing four times with PBS-T. Antibody, diluted in PBS-T, was then added to the wells and the assay continued as described above for the Immunoassay on Methanol-Fixed Bacteria.

Activity Assays

Antibodies that bind to an antigen may not necessarily enhance opsonization or enhance protection from infection. Therefore, an opsonization assay was used to determine the functional activities of the antibodies.

An opsonization assay can be a calorimetric assay, a chemiluminescent assay, a fluorescent or radiolabel uptake assay, a cell-mediated bactericidal assay, or any other appropriate assay known in the art which measures the opsonic potential of a substance and thereby identifies reactive immunoglobulin. In an opsonization assay, an infectious agent, a eukaryotic cell, and the opsonizing substance to be tested, or an opsonizing substance plus a purported opsonizing enhancing substance, are incubated together.

In certain embodiments, the opsonization assay is a cell-mediated bactericidal assay. In this in vitro assay, an infectious agent such as a bacterium, a phagocytic cell, and an opsonizing substance such as immunoglobulin, are incubated together. Any eukaryotic cell with phagocytic or binding ability may be used in a cell-mediated bactericidal assay. In certain embodiments, phagocytic cells are macrophages, monocytes, neutrophils, or any combination of these cells. Complement proteins may be included to promote opsonization by both the classical and alternate pathways.

The opsonic ability of an antibody is determined by the amount or number of infectious agents remaining after incubation. The fewer the number of infectious agents that remain after incubation, the greater the opsonic activity of the antibody tested. In a cell-mediated bactericidal assay, opsonic activity is measured by comparing the number of surviving bacteria between two similar assays, only one of which contains the antibody being tested. Alternatively, opsonic activity is determined by measuring the number of viable organisms before and after incubation with a sample antibody. A reduced number of bacteria after incubation in the presence of antibody indicates a positive opsonizing activity. In the cell-mediated bactericidal assay, positive opsonization is determined by culturing the incubation mixture under appropriate bacterial growth conditions. Any reduction in the number of viable bacteria comparing pre-incubation and post-incubation samples, or between samples which contain immunoglobulin and those that do not, is a positive reaction.

Neutrophil-Mediated Opsonophagocytic Bactericidal Assay: The assay was performed using neutrophils isolated from adult venous blood by sedimentation using PMN Separation Medium (Robbins Scientific catalog no. 1068-00-0). Forty microliters of antibody, serum, or other immunoglobulin source, was added at various dilutions to replicate wells of a round-bottom microtiter plate. Forty microliters of neutrophils (approximately $2 \times 10^6$ cells per well) was then added to each well, followed immediately by approximately $3 \times 10^4$ mid-log phase bacteria (*S. epidermidis* strain Hay, ATCC 55133 or *S. aureus* type 5, gift from S. Wilson, Uniformed Services University of the Health Sciences) in 10 ul Tryptic Soy Broth (Difco cat. no. 9063-74, or equivalent). Finally, 10 µl of immunoglobulin-depleted human serum was added as a source of active complement. (Immunoglobulins were removed from human serum complement by preincubating the serum with Protein G-agarose and Protein L-agarose before use in the assay, this depletion of immunoglobulins minimized the concentrations of anti-staphylococcal antibodies in the complement, thereby reducing bacterial killing caused by inherent antibodies in the complement solution.)

The plates were incubated at 37° C. with constant, vigorous shaking. Aliquots of 10 µl were taken from each well at zero time, when the sample antibody was first added, and after 2 hours of incubation. To determine the number of viable bacteria in each aliquot harvested from each sample well, each aliquot was diluted 20-fold in a solution of 0.1% BSA in water (to lyse the PMNs), mixed vigorously by rapid pipetting, and cultured on blood agar plates (Remel, cat. no. 01-202, or equivalent) overnight at 37° C. The opsonic activity was measured by comparing the number of bacterial colonies observed from the sample taken at two hours with the number of bacterial colonies observed from the sample taken at time zero. Colonies were enumerated using an IPI Minicount Colony Counter.

Nasal Colonization Assay: The mouse nasal colonization model for S. aureus was based on the work of Kiser et al. (47). Briefly, streptomycin resistant S. aureus type 5 is grown on high salt Columbia agar (Difco) to promote capsule formation. The bacteria are washed with sterile saline (0.9% NaCI in water) to remove media components and resuspended at ~10$^8$ bacteria/animal dose in saline (0.9% NaCI in water) containing various concentrations and combinations of anti-staphylococcal or irrelevant control MAbs. Following one hour preincubation, the bacteria are pelleted and resuspended in a final volume of 10 µl per animal dose in either saline or saline containing antibody. Mice that have been maintained on streptomycin-containing water for 24 hours are sedated with anesthesia. Staphylococci are injected into the nares of the mice by pipetting without contacting the nose.

After four to seven days, during which the animals are maintained on streptomycin-containing water, the animals are sacrificed and the noses removed surgically and dissected. Nasal tissue is vortexed vigorously in saline (0.9% NaCI in water) plus 0.5% Tween-20 to release adherent bacteria and the saline is plated on Columbia blood agar (Remel) and tryptic soy agar (Difco) containing streptomycin to determine colonization.

The invention, having been described above, may be better understood by reference to examples. The following examples are intended for illustration purposes only, and should not be construed as limiting the scope of the invention in any way.

EXAMPLE 1

The Production of Hybridomas and Monoclonal Antibodies

Antibodies were raised against lipoteichoic acid (LTA) from S. aureus by immunizing mice with an LTA conjugate. LTA conjugates LTA/PspA, LTA/SIA/TT, and LTA/GMBS/TT, prepared as set forth below, were used.

To prepare each conjugate, LTA was first derivatized with thiol groups as follows. S. aureus LTA (Sigmna Chemical Co.) was purified essentially as described in Fischer et al. (9). The purified LTA was diluted to 4 mg/ml with water. One hundred microliters of 0.75 M HEPES, 10 mM EDTA, pH 7.5 and 100 µl of 0.1 M SPDP (Pierce) were added to 1 ml of S. aureus LTA. The reaction was incubated for 4 hours at room temperature, and then 55 pi of 0.5 M DTT was added and the solution was dialyzed overnight at 4° C. against 2 mM EDTA, pH 5 (2×1 L). The reaction resulted in 0.27 mM thiol (LTA-SH) in a 1.2 mL volume, or 0.32 µmol thiol, as determined by DTNB assay (2).

LTA/PspA conjugate was prepared as follows. Three milligrams of pneumococcal surface protein A (PspA; 188 µl of a 16 mg/ml solution in PBS; prepared essentially as described in Wortham et al. (43) was combined with 25 µl of 0.75 M HEPES, 10 mM EDTA, pH 7.3 and 17 ul 0.1 M N-hydroxysuccinimidyl iodoacetate (SIA; Bioaffinity Systems) and incubated for 2 hours at room temperature. The volume of the solution was then made up to 2 ml with 10 mM sodium acetate, 0.15 M NaCI, 2 mM EDTA, and then concentrated to a final volume of about 150 µl using an Ultrafree 4 device (30 kDa cutoff; Amicon). The resulting iodoacetyl PspA was then combined with 400 µl of LTA-SH. The pH was raised to 8 with 1 M HEPES pH 8, and the reaction proceeded overnight at 4° C.

The solution was then fractionated on a 1×60 cm S-200HR column, which had been equilibrated with 0.1 % deoxycholate (DOC) in PBS. The void volume fractions were pooled, dialyzed into saline (0.15 M NaCI) to remove DOC and PBS, and had an optical density of 0.14 at 280 nm. The concentration of protein in the conjugate solution was 0.66 mg/ml by BCA assay (Pierce Chemical Company), and the concentration of phosphate in the conjugate solution was 0.88 mM by phosphate assay (1).

LTA/SIA/TT conjugate was prepared as follows. Four milligrams of tetanus toxoid (TT; 280 µl of 14.5 mg/ml; SmithKline Beecham), diluted to 4 ml with 2 M NaCI was concentrated to 50 µl using an Ultrafree 4 centrifugal filter with a 30 kD cutoff (Millipore). The resulting solution was diluted to 250 µl with 2 M NaCI (TT/2 M NaCI). Seventy-five microliters of 0.25 M HEPES, 2 mM EDTA, pH 7.5 and 8 µl N-hydroxysuccinimide iodoacetate (SIA; Bioaffinity Systems, Roscoe, Ill.) were added to 125 µl of TT/2 M NaCI. The reaction was incubated for 2 hours at room temperature and then diluted to about 2 ml with 2 M NaCI. The solution was then concentrated to 150 µl using an Ultrafree 4 centrifugal filter.

One hundred and fifty microliters of the resulting product, iodoacetylated TT, was combined with 400 µl of LTA-SH. The reaction is incubated overnight at 4° C. The reaction was fractionated on a 1×60 cm Sephacryl S-200HR column (Pharmacia), equilibrated with 0.1% deoxycholate in PBS. The void volume fractions, containing the LTA/SIA/TT conjugate, were pooled, dialyzed into saline to remove DOC and PBS, and had an optical density of 0.77 at 280 nm. The yield of TT in the conjugate was 0.77 mg/ml by BCA assay (Pierce Chemical Co.). The concentration of phosphate in the conjugate solution was 0.77 mM by phosphate assay (1).

LTA/GMBS/TT conjugate was prepared as follows. Four milligrams of TT (280 pi of 14.5 mg/ml; SmithKline Beecham), diluted to 4 ml with 2 M NaCI was concentrated to 50 µl using an Ultrafree 4 centrifugal filter with a 30 kD cutoff (Millipore). The resulting solution was diluted to 250 ul with 2 M NaCI (TT/2 M NaCI). Seventy-five microliters of 0.15 M HEPES, 2 mM EDTA, pH 7.5 and 8 µl N-hydroxysuccinimide gamma butyric maleimide (GMBS; Bioaffinity Systems, Roscoe, Ill.) were added to 125 µl of TT/2 M NaCI. The reaction was incubated for 2 hours at room temperature and then diluted to 2 ml with 2 M NaCI. The solution was then concentrated to 150 µl using an Ultrafree 4 centrifugal filter.

Four hundred microliters of LTA-SH was added to the concentrated solution, and the pH was raised to 8 with 1 M HEPES pH 8. The reaction was incubated overnight at 4° C. The reaction was fractionated on a 1×60 cm Sephacryl S-200HR column (Pharmacia), equilibrated with 0.1% deoxycholate in PBS. The void volume fractions, containing the LTA/GMBS/TT conjugate, were pooled and dialyzed into saline to remove DOC and PBS. The yield of TT was 0.83 mg/ml by BCA assay (Pierce Chemical Co.), and the concentration of phosphate in the conjugate solution was 1.45 mM by phosphate assay (1).

The presence of LTA in each of the conjugates was confirmed by Western blot following 12% SDS-PAGE electrophoresis of the product.

Twenty-four approximately 4 month old female BALB/c mice were separated into six groups and immunized with 10 μg (groups A, C, and E) or 1 μg (groups B, D, and F) of LTA/PspA (groups A and B), LTA/SIA/TT (groups C and D), or LTA/GMBS/TT (groups E and F; Table 1).

TABLE 1

LTA Immunization Groups

| Immun. Group | Antigen | ug/mouse | Mouse Ids |
|---|---|---|---|
| A | LTA/PspA | 10 | 1375-1378 |
| B | LTA/PspA | 1 | 1379-1382 |
| C | LTA/SIA/TT | 10 | 1383-1386 |
| D | LTA/SIA/TT | 1 | 1387-1390 |
| E | LTA/GMBS/TT | 10 | 1391-1394 |
| F | LTA/GMBS/TT | 1 | 1395-1398 |

All immunizations were administered subcutaneously in 50% RIBI adjuvant. The mice received a boost 21 days after the primary immunization, and a second boost 79 days after the primary immunization. Boosts were performed as described for the primary immunizations. Eyebleeds were taken at 0 days, 21 days, 35 days, 79 days, 94 days, and 119 days after the primary immunization. Serum collected at 21 days and 35 days was tested by ELISA for antibodies to LTA (Table 2).

TABLE 2

Anti-LTA Titers of Serum Pools

| Group | Antigen | μg/mouse | prebleed titer* | 21 day titer* | 35 day titer* |
|---|---|---|---|---|---|
| A | LTA/PSPA | 10 | 77 | 2885 | 4748 |
| B | LTA/PSPA | 1 | 57 | 2668 | 4667 |
| C | LTA/SIA/TT | 10 | 199 | 51353 | 54085 |
| D | LTA/SIA/TT | 1 | 2520 | 11525 | 26229 |
| E | LTA/GMBS/TT | 10 | 783 | 11631 | 140392 |
| F | LTA/GMBS/TT | 1 | 10 | 3635 | 85832 |

*titer is the serum dilution required to obtain an absorbance of 0.5 in an anti-LTA ELISA Serum collected at 35 days and 79 days was also tested for antibodies to LTA by ELISA, and serum collected at 94 days was tested by ELISA, and in an LBE assay against *S. epidermidis* strain Hay and *S. aureus* (Table 3).

TABLE 3

Comparison of Anti-LTA Titers and LBE Titers

| Group | Antigen | μg/mouse | ELISA* 35 day | ELISA* 79 day | ELISA* 94 day | LBE** S. epi 94 | LBE*** S. aur 94 |
|---|---|---|---|---|---|---|---|
| A | LTA/PSPA | 10 | 16053 | 4110 | 65241 | 531 | 26 |
| B | LTA/PSPA | 1 | 23505 | 8806 | 156343 | 150 | 13 |
| C | LTA/SIA/TT | 10 | 153227 | 39034 | 279505 | 520 | 29 |
| D | LTA/SIAAT | 1 | 98798 | 20135 | 313256 | 980 | 50 |
| E | LTA/GMBS/TT | 10 | 230410 | 46859 | 299995 | 1903 | 409 |
| F | LTA/GMBS/TT | 1 | 88756 | 24338 | 447440 | 2475 | 541 |

*The ELISA titer is the serum dilution required to obtain an absorbance of 1.0
**The LBE titer for *S. epidermidis* strain Hay is the serum dilution required to obtain an absorbance of 1.0.
***The LBE titer for *S. aureus* is the serum dilution required to obtain an absorbance of 0.5.

Based on the results of the ELISA assays and LBE assays, day 94 and day 119 sera from individual mice in groups E and F were tested by ELISA, and in an opsonic assay against *S. aureus* (Table 4).

Mouse 1396, which had been immunized with LTA/GMBS/TT, was selected because serum from the mouse showed a strong signal by anti-LTA ELISA, and was opsonic against *S. aureus*. Mouse 1396 was boosted one more time at day 134, and then sacrificed on day 141, and spleen removed and used to make hybridomas.

TABLE 4

Anti-LTA ELISA and Opsonic Assay of Individual Mouse Sera

| | | | | S. aureus opsonic assay** | | | | | |
|---|---|---|---|---|---|---|---|---|---|
| ID | Antigen Dose | ELISA* prebleed | ELISA* day 119 | Prebleed neat | Prebleed 1:5 | day 94 | day 94 | day 119 | day 119 | day 119 |
| 1391 | 10 | | 16364 | 53 | | 20 | 68 | 0 | 40 | 14 |
| 1392 | 10 | 18142 | 47915 | | | 19 | 53 | 0 | 1 | 21 |
| 1393 | 10 | | 18870 | | | 65 | | 2 | 12 | 37 |
| 1394 | 10 | 22 | 32126 | 77 | 25 | 78 | 33 | 29 | 50 | 67 |
| 1395 | 1 | | 29091 | 7 | 6 | 44 | 16 | 23 | 17 | 39 |
| 1396 | 1 | 0 | 90249 | | | 53 | 20 | | 74 | 64 |

TABLE 4-continued

Anti-LTA ELISA and Opsonic Assay of Individual Mouse Sera

| | | | | | | S. aureus opsonic assay** | | | | |
|---|---|---|---|---|---|---|---|---|---|---|
| ID | Antigen Dose | ELISA* prebleed | ELISA* day 119 | Prebleed neat | Prebleed 1:5 | day 94 | day 94 | day 119 | day 119 | day 119 |
| 1397 | 1 | 0 | 40833 | | | 53 | | 0 | 33 | 0 |
| 1398 | 1 | 0 | 16601 | | | 60 | 27 | 40 | 31 | 37 |

*serum dilution required to obtain an absorbance of 1.0.
**numbers are percent killing.

Hybridomas were prepared by the general methods of Shulman, Wilde and Kohler; and Bartal and Hirshaut (34, 48). A total of $2.08 \times 10^8$ spleenocytes from mouse 1396 were mixed with $2.00 \times 10^7$ SP2/0 mouse myeloma cells (ATCC Catalog number CRL1581) and pelleted by centrifugation (400×g, 10 minutes at room temperature) and washed in serum free medium. The supernatant was removed to near-dryness and fusion of the cell mixture was accomplished in a sterile 50 ml centrifuge conical by the addition of 1 ml of warm (37° C.) polyethylene glycol (PEG; mw 1400; Boehringer Mannheim) over a period of 60-90 seconds. The PEG was diluted by slow addition of serum-free medium in successive volumes of 1, 2, 4, 8, 16 and 19 mls. The hybridoma cell suspension was gently resuspended into the medium and the cells pelleted by centrifugation (500×g, 10 minutes at room temperature). The supernatant was removed and the cells resuspended in medium RPMI1640, supplemented with 10% heat-inactivated fetal bovine serum, 0.05 mM hypoxanthine and 16 µM thymidine (HT medium). One hundred µl of the hybridoma cells were planted into 952 wells of 96-well tissue culture plates. Eight wells (column 1 of plate A) received approximately $2.5 \times 10^4$ SP2/0 cells in 100 µl. The SP2/0 cells served as a control for killing by the selection medium added 24 hours later.

Twenty four hours after preparation of the hybridomas, 100 µl of RPMI 1640, supplemented with 10% heat-inactivated fetal bovine serums, 0.1 mM hypoxanthine, 0.8 µM aminopterin and 32 µM thymidine (HAT medium) was added to each well.

Forty-eight hours after the preparation of the hybridomas, the SP2/0 cells in plate A, column 1 appeared to be dead, indicating that the HAT selection medium had successfully killed the unfused SP2/0 cells.

Ten days after the preparation of the hybridomas, supernatants from all wells were tested by ELISA for the presence of antibodies reactive with methanol-fixed S. aureus LTA. Based on the results of this preliminary assay, cells from 12 wells were transferred to a 24-well culture dish. Three days later, supernatant from these cultures were retested by ELISA for the presence of antibodies that bind to LTA.

The absorbance values for eleven of the culture supernatants were less than 0.100. However, the absorbance value obtained with the supernatant from hybridoma culture 00-107GG12 was 4.000. This culture was expanded for further evaluation and cloned into two 96-well culture dishes. Cloning was accomplished by diluting the cell suspension into 4.5 viable cells per ml in RPM11640, supplemented with 15% fetal bovine serum, 5% Hybridoma SFM (Life Technologies) and 100 µg/ml of kanamycin.

Ten days later, the supernatants from the hybridoma clones were tested by ELISA for binding to S. aureus LTA. Only one clone, ID12, bound strongly to LTA, with an absorbance of 3.500). In contrast, the absorbance values for the remaining supernatants were less than 0.220. Hybridoma clone 00-107GG12 ID12 was expanded and cryopreserved. Isotype determination revealed that both the original hybridoma (00-107GG12) and its clone (00-107GG12 ID12) were mouse IgG2a heavy chains with kappa light chains. The monoclonal antibody produced by hybridoma 00-107GG12 ID12 was designated M120.

EXAMPLE 2

Opsonic Activity of M120

Opsonic assays were carried out substantially as described above under the heading "Neutrophil-mediated Opsonophagocytic Bactericidal Assay". M120 was purified from ascites essentially as described by the manufacturer of MEP Hypercel gel (BiSepra). Thirty-three ml of buffer A (50 mM Tris, 5 mM EDTA, pH 8) was added to 17 ml of mouse ascites, and then centrifuged for 15 minutes at 4000 rpm in an Eppendorf model 5810R centrifuge using rotor A462. The solution was filtered using Whatman GD/XP PES 0.45µ membrane (cat. no. 6994-2504) and the volume of diluted ascites was 47 ml after filtering. The solution was loaded onto a 1 cm×7 cm MEP hypercel column that had been equilibrated with buffer A, at a rate of 1.8 ml/min. The column was washed with buffer A, and then with buffer A+25 mM sodium caprylate until the OD280 was <0.05. The column was then washed with water until the $OD_{280}$<0.05. The column was eluted with buffer B (50 mM sodium acetate, 5 mM EDTA, pH 4) and the eluent collected at a rate of 70 drops/min. The main peak (pool A) and its trailing end (pool B) were pooled separately and dialyzed against PBS (2×2L) at 4° C. The dialyzed solution was sterile filtered using a Millex GV device (Millipore). By $OD_{280}$, pool A contained 3.2 mg/ml antibody, and pool B contained 0.25 mg/ml antibody.

First, the opsonic activity of M120 was determined against S. aureus Type 5 (Table 5).

TABLE 5

Opsonic Activity of M120 (200 µg/ml) against S. aureus Type 5

| Description | Assay 1 | Assay 2 | Assay 3 | Assay 4 |
|---|---|---|---|---|
| PMNs alone | 0 | 0 | 0 | 0 |
| C alone | 0 | 9 | 0 | 0 |
| PMNs + C | 0 | 16 | 25 | 11 |
| M120 alone | 20 | 0 | 0 | 0 |
| M120 + PMNs + C' | 73 | 84 | 85 | 85 |

Next, the opsonic activity of M120 was determined against S. epidermidis strain Hay (Table 6). This assay was also performed as described above under the heading "Neutrophil-Mediated Opsonophagocytic Bactericidal Assay".

TABLE 6

Opsonic activity of M120 against *S. epidermidis* strain Hay

| Description | MAb (μg/ml) | % killed |
|---|---|---|
| PMNs alone | | 0 |
| C' alone | | 0 |
| PMNs + C' | | 0 |
| M120 alone | 200 | 17 |
| M120 + PMNs + C' | 200 | 95 |
| " | 100 | 97 |
| " | 30 | 75 |
| " | 10 | 87 |
| " | 3.3 | 55 |

A similar assay was used to determine the opsonic activity of MAb-391.4 against *S. epidermidis* strain Hay (Table 7). Thus, MAb-391.4, which was raised against UV-killed *S. aureus*, has strong opsonic activity against *S. epidermidis* strain Hay.

TABLE 7

Opsonic activity of MAb-391.4 against *S. epidermidis* strain Hay

| Description | MAb (pg/ml) | % killed |
|---|---|---|
| PMNs alone | | 10.9 |
| C' alone | | 0 |
| PMNs + C' | | 0 |
| M120 alone | 120 | 24.7 |
| M120 + PMNS + C' | 120 | 81.9 |
| " | 50 | 57.9 |

EXAMPLE 3

Cloning of the M120 Variable Regions

Total RNA was isolated from $4 \times 10^6$ frozen 00-107 GG12 ID12 hybridoma cells using the Midi RNA Isolation kit (Qiagen) following the manufacturer's procedure. The RNA was dissolved in 10 mM Tris, 0.1 mM EDTA (pH 8.4) containing 0.03U/(μg Prime RNase Inhibitor (Sigma) to a final concentration of 025 μg/μl.

FIG. 3 shows the strategy for cloning the variable region genes. The total RNA (2 μg) was converted to cDNA by using Superscript II-MMLV Reverse Transcriptase (Life Technologies) and mouse Kappa chain-specific primer (JSBX-18; SEQ ID NO: 5) and a mouse heavy chain-specific primer (JSBX-25A; SEQ ID NO: 6) according to the manufacturer's procedures (see FIG. 4 for primer sequences). The first strand cDNA synthesis products were then purified using a Centricon-30 concentrator device (Amicon). Of the 40 μl of cDNA recovered, 5 μl was used as template DNA for PCR. Typical PCR amplification reactions (50 μl) contained template DNA, 30 pmoles of the appropriate primers (JSBX-9A, 11A, and 18 for light chains, SEQ ID NOs: 3-5; JSBX-1, 4 and JSBX-25A for heavy chains, SEQ ID NOs: 1, 2, and 6), 2.5 units of ExTaq polymerase (PanVera), 1× ExTaq reaction buffer, 200 μM dNTP, 2 mM MgCl2. The template was denatured by an initial incubation at 96° C. for 3 min. The products were amplified by 30 thermal cycles of 96° C. for 1 min., 60° C. for 30 sec, 72° C. for 30 seconds. The PCR products from the successful reactions were purified using the Nucleospin PCR Purification system (Clontech) as per manufacturer's procedure.

The PCR products (approximately 400 base pairs each) were then cloned into a bacterial vector, pGEM T (Promega) for DNA sequence determination. PCR fragments were ligated into pGEM T, a T/A style cloning vector, following the manufacturer's procedures using a 3:1 insert to vector molar ratio. One half (5 μl) of the ligation reactions were used to transform Ultracompetent XL1 Blue cells (Stratagene) as per the manufacturer's procedure. Bacterial clones containing plasmids with DNA inserts were identified using diagnostic restriction enzyme digestions with DraIII and BsiWI (for heavy chain clones) or DraIII and EcoRV (for light chain clones) (New England Biolabs). The DNA sequences of plasmids containing inserts of the appropriate size (~400 bp) were then determined. The plasmid containing the A120 heavy chain sequence was designated pJSB16-6 and the plasmid containing the A120 light chain variable region was designated pJSB17-23. The final consensus DNA sequences of the light chain and heavy chain variable regions are shown in FIG. 5 and FIG. 6, respectively.

Having sequenced the variable regions of both M110 and M120, we compared them. The homology was striking at both the DNA and amino acid levels. As set forth in FIG. 9 there is a 96% homology at the DNA level, with 662 out of 687 bases the same Further, at the amino acid level, there is a 94% homology, with 216 amino acids out of 225 the same, as set forth in FIG. 10. As noted above, M120 was raised agains *S. aureus* LTA, while M110 was raised against *S. epidermis* strain Hay. Both antibodies exhibit opsonic activity against both *S. epidermis* and *S. aureus*. The high level of homology between the M110 and M120 variable regions may suggest a common structural motif that contributes to the opsonic capability of the antibodies.

EXAMPLE 4

Production of Recombinant Chimeric Mouse/Human Antibody Molecules

The heavy and light chain variable regions were then subcloned into a mammalian expression plasmid vector for production of recombinant chimeric mouse/human antibody molecules. The human/mouse chimera of the M120 antibody is designated A120, and the human/mouse chimera of the M110 antibody is designated A110 (see U.S. Pat. No. 6,610, 293, filed Jun. 15, 1998).

As set forth below, vectors were designed that express recombinant antibody molecules under the control of CMV transcriptional promoters. The chimeric heavy chains are expressed as a fusion of a heavy chain variable region and a human 1gG1 constant domain. The chimeric light chains are expressed as a fusion of a light chain variable region and a human kappa chain constant region. The chimeric light chain cDNA contains a mouse kappa intron between the variable region and the human kappa constant region. After splicing, the variable region becomes fused to a human Kappa constant region exon. The selectable marker for the vector in mammalian cells is Neomycin resistance (resistance to G418).

The variable region gene fragments of M120 were re-amplified by PCR using primers that adapted the fragments for cloning into the expression vector {see FIG. 4, JSBX-46 through JSBX-49, SEQ ID NOs: 7-9 and 18). The heavy chain front primer (JSBX-46; SEQ ID NO: 7) includes a 5'tail that encodes the C-terminus of the heavy chain leader and a Ss/WI restriction site for cloning, while the heavy chain reverse primer (JSBX-47; SEQ ID NO: 8) adds a 3' EcoRI restriction site for cloning. This results in the addition of two amino acids, glutamine (E) and phenylalanine (F) between the heavy chain variable region and the human 1gG1 constant region. The light chain front primer (JSBX-48; SEQ ID NO: 9) introduces a 5' tail that encodes the two C-terminal amino acids of the light chain leader and an AgeI/restriction site for cloning purposes. The light chain reverse primer (JSBX-49; SEQ ID NO: 18) adds a 3' DNA sequence for the joining region-Kappa exon splice junction followed by a BstBI restriction site for cloning. The variable regions were re-amplified from the plasmid DNA using vector pJSB16-6 for the heavy chain variable region and vector pJSB17-23 for the light chain variable region. PCR reactions were performed as described above. Following a 3 minute incubation at 96° C., the PCR parameters were 30 thermal cycles of 58° C. for 30 seconds, 70° C. for 30 seconds, and 96° C. for 1 minute.

Figure 7:
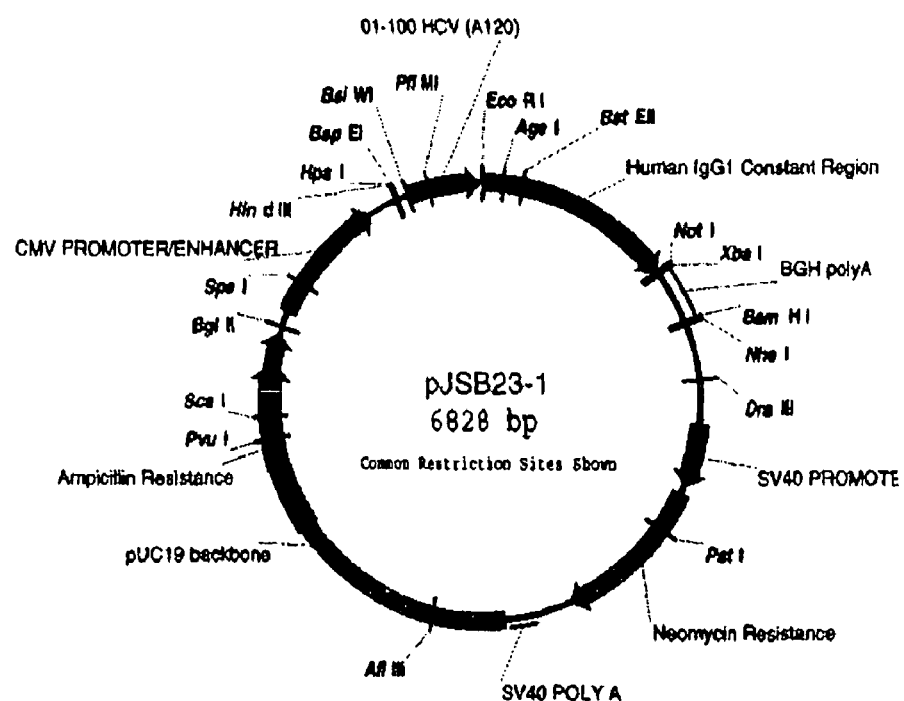
FIG. 7 depicts the pJSB23-1 plasmid that expresses the A120 heavy chain.
Figure 8:
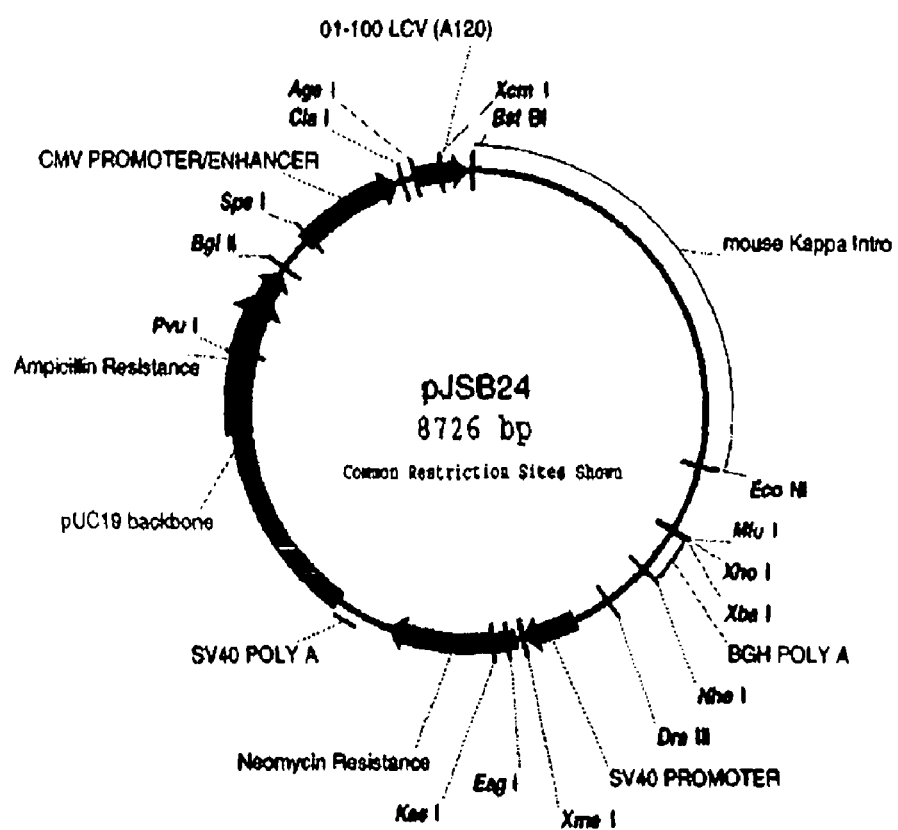
FIG. 8 depicts the pJSB24 plasmid that expresses the A120 light chain.

The heavy chain variable region PCR product was digested with BsiWI and EcoRI (New England Biolabs), purified using a Nucleospin PCR Purification column (Clontech), as described by the manufacturer, and ligated into BsiWI/EcoRI/PflMI-digested and gel-purified pJRS383 vector using the Takara Ligation Kit (Panvera) following the manufacturer's procedure. The ligation mix was then transformed into XL1Blue cells (Stratagene), resulting in plasmid mammalian expression vector pJSB23-1 (FIG. 7). The light chain variable region PCR product (approximately 350 bp) was digested with AgeI and BstBI (New England Biolabs), and purified using a Nucleospin PCR Purification column (Clontech) as described by the manufacturer. The light chain variable region fragment was ligated into pJRS384 that had been AgeI/BstBI/Xcm1-digested and gel-purified using the Takara Ligation Kit (Panvera) following the manufacturer's procedure. The ligation mix was transformed into XL1Blue cells (Stratagene), resulting in mammalian expression plasmid pJSB24 (FIG. 8).

Figure 11:
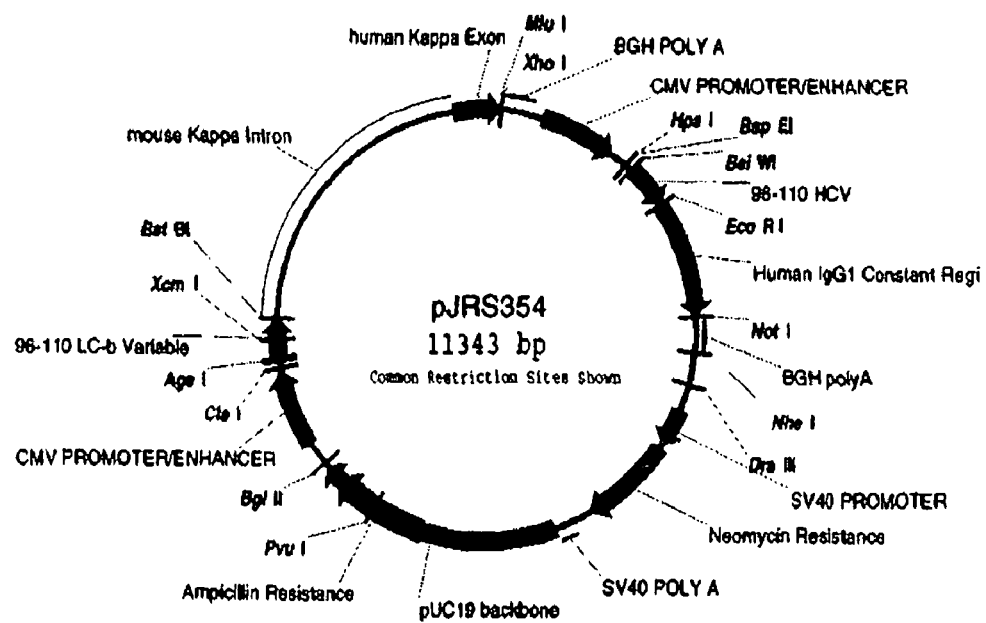
FIG. 11 depicts the pJRS354 bi-cistronic plasmid that expresses the A110 heavy chain and light chain variable regions.
Figure 12:
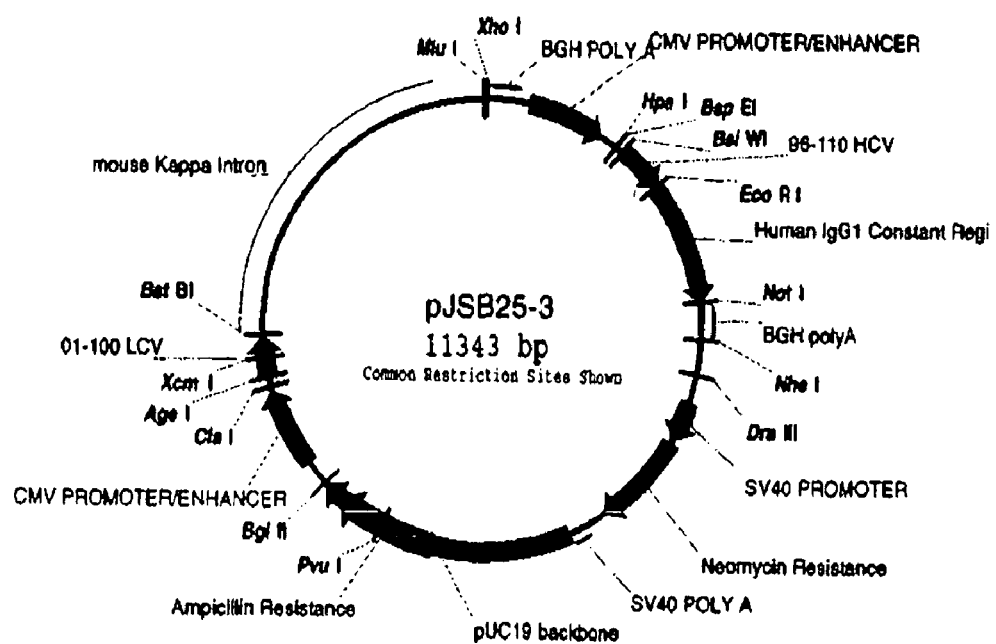
FIG. 12 depicts the pJSB25-3 bi-cistronic plasmid that expresses the A110 heavy chain variable region and the A120 light chain variable region.

Because of the similarity between the A110 and the A120 antibody sequences, we decided to construct mammalian cell expression plasmids that contained the A120 heavy and light chain variable regions in a bi-cistronic plasmid, as well as plasmids that combined the A110 heavy chain variable region with the A120 light chain variable region, and the A110 light chain variable region with the A120 heavy chain variable region, in order to investigate the binding and opsonic properties of the different antibodies. Construction of the bi-cistronic vectors was done in a step-wise fashion, in which the heavy and light chain variable regions of A120 were cloned into a bi-cistronic expression plasmid already containing the A110 light and heavy chain variable regions (pJRS354, FIG. 11), replacing the A110 light chain variable region, heavy chain variable region, or both. The plasmid pJRS354 was digested with ClaI and XhoI (New England Biolabs), the digestion products were separated on an agarose gel and the backbone fragment was cut out and gel purified using a Nucleospin Gel Fragment DNA Purification column (Clontech), as described by the manufacturer. The plasmid pJSB24 was digested with ClaI and XhoI (New England Biolabs), the digestion products were separated on an agarose gel and the light chain variable region fragment was cut out and gel purified using a Nucleospin Gel Fragment DNA Purification column (Clontech), as described by the manufacturer. These fragments were then ligated together using the Takara Ligation Kit (Panvera) following the manufacturer's procedure. The resulting bi-cistronic expression vector, pJSB25-3 (FIG. 12), which contained the A120 antibody light chain variable region and the A110 antibody heavy chain variable region, was then used for antibody production in transfected mammalian cells after sequence confirmation of the variable regions.

Figure 13:
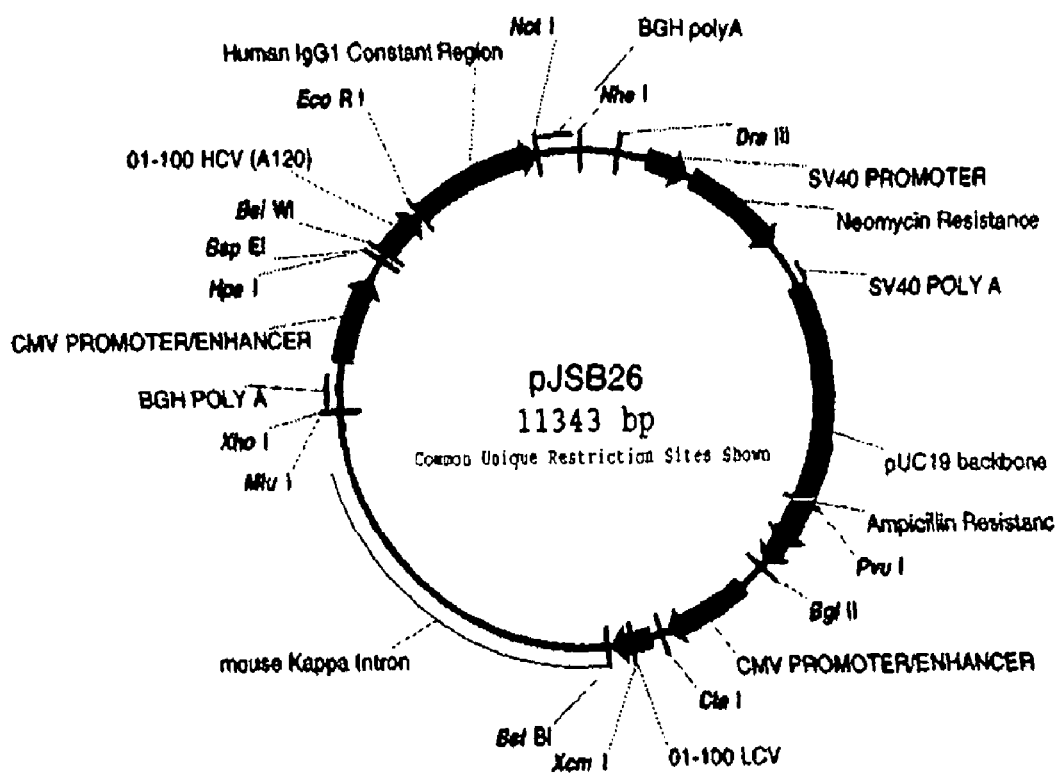
FIG. 13 depicts the pJSB26 bi-cistronic plasmid that expresses the A120 heavy chain and light chain variable regions.

The two other bi-cistronic plasmids were constructed in a similar manner. The plasmid pJSB25-3 was digested with BspEI and NotI (New England Biolabs), the digestion products were separated on an agarose gel and the backbone fragment was cut out and gel purified using a Nucleospin Gel Fragment DNA Purification column (Clontech), as described by the manufacturer. The plasmid pJSB23-1 was digested with BspEI and NotI (New England Biolabs), the digestion products were separated on an agarose gel and the heavy chain variable region fragment was cut out and gel purified using a Nucleospin Gel Fragment DNA Purification column (Clontech), as described by the manufacturer. These fragments were ligated together using the Takara Ligation Kit (Panvera) following the manufacturer's procedure. The resulting bi-cistronic expression vector, pJSB26 (FIG. 13), which contained the light and heavy chain variable regions of the A120 antibody, was then used for antibody production in transfected mammalian cells.

Figure 14:
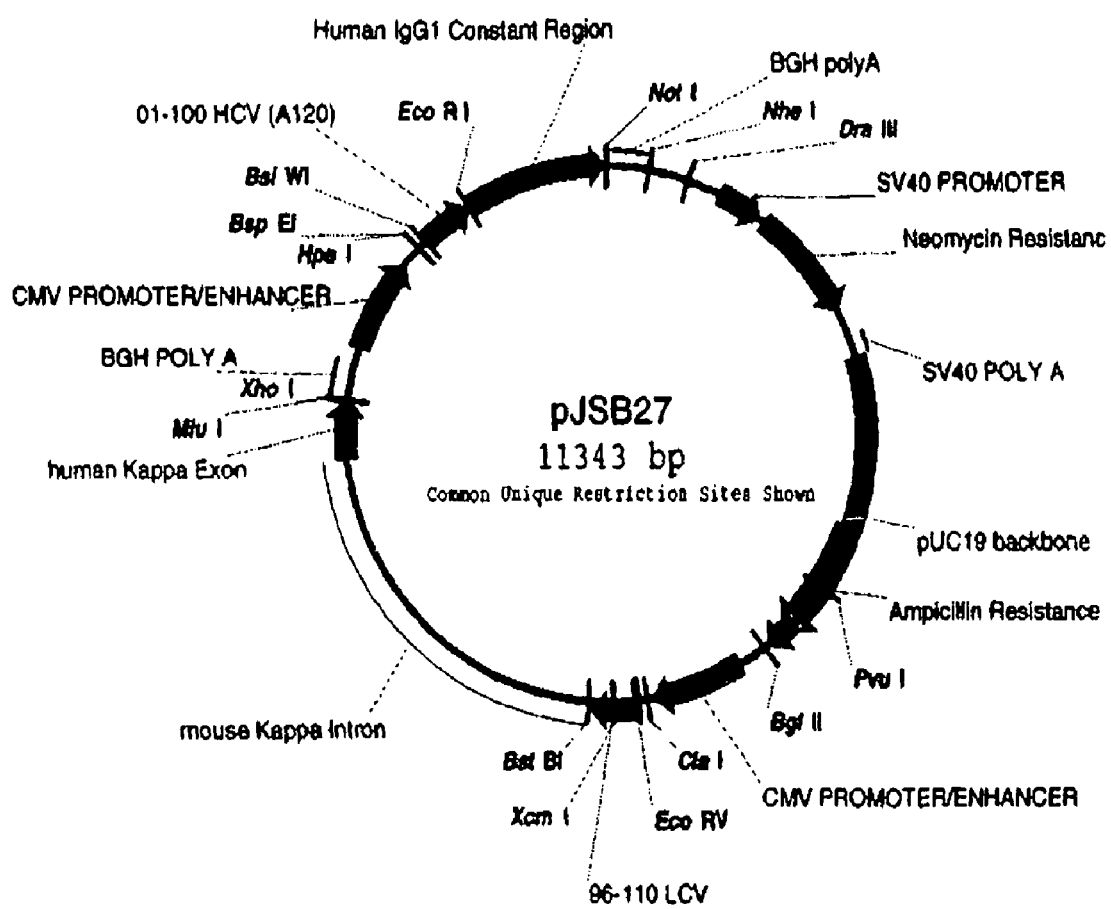
FIG. 14 depicts the pJSB27 bi-cistronic plasmid that expresses the A120 heavy chain variable region and the A110 light chain variable region.

The plasmid pJRS354 was digested with BspEI and NotI (New England Biolabs), the digestion products were separated on an agarose gel and the backbone fragment was cut out and gel purified using a Nucleospin Gel Fragment DNA Purification column (Clontech), as described by the manufacturer. The plasmid pJSB23-1 was digested with BspEI and NotI (New England Biolabs), the digestion products were separated on an agarose gel and the heavy chain variable region fragment was cut out and gel purified using a Nucleospin Gel Fragment DNA Purification column (Clontech), as described by the manufacturer. These fragments were ligated together using the Takara Ligation Kit (Panvera) following the manufacturer's procedure and transformed into XUBlue cells (Stratagene). The resulting bi-cistronic expression vector, pJSB27 (FIG. 14), which contained the heavy chain variable region of the A120 antibody and the light chain variable region of the A110 antibody, was then used for antibody production in transfected mammalian cells.

EXAMPLE 5

Comparison of the A120 and A110 Anti-LTA Human/Mouse Chimeric Antibodies

Anti-LTA human/mouse chimeric antibody A110 was previously described in U.S. patent application Ser. No. 09/097,055, now U.S. Pat. No. 6,610,293, which is herein incorporated by reference. The binding activities of anti-LTA human/mouse chimeric antibodies A110 and A120 were compared in ELISA assays against LTA.

Dilutions of A120 supernatant were compared to dilutions of purified A110 antibody in an immunoassay as described above under the heading "Binding Assays", subheading "Immunoassay on LTA". Briefly, the wells of a 96-well plate were coated with 1 μg/ml of S. aureus LTA for three hours at room temperature. After washing, dilutions of purified A110 antibody or A120 supernatant in PBS-T were added to quadruplicate wells and incubated for 30 to 60 minutes at room temperature. After washing, HRP-conjugated gamma-specific goat anti-human IgG, diluted 1:5000, was added to each well and incubated for 30 to 60 minutes at room temperature. After removing the secondary antibody and washing, 100 μl TMB substrate was added to each well and incubated for 15 minutes at room temperature. One hundred microliters of TMB stop reagent was then added to each well to stop the reaction, and the absorbance of each well at 450 nm was determined. The results of the anti-LTA ELISA assay are shown in Table 8.

TABLE 8

Binding of A110 and A120 to LTA-coated plates

| A110 (ng/ml) | A450 | A120 supernatant dilution | A450 |
|---|---|---|---|
| 40 | 2.691 | 10 | 4.000 |
| 20 | 1.741 | 20 | 3.967 |
| 10 | 0.952 | 40 | 3.927 |
| 5 | 0.555 | 80 | 3.327 |
| 2.5 | 0.322 | 160 | 2.824 |
| 1.25 | 0.180 | 320 | 1.907 |
| 0.625 | 0.115 | 640 | 1.148 |
| PBS-T | 0.050 | PBS-T | 0.052 |

This assay shows that monoclonal antibody A120, like A110, binds to LTA of S. aureus. In order to compare the binding affinity of the two antibodies, A120 was purified using Protein G Ultralink (Pierce) per the manufacturer's procedure, and the two antibodies were tested for binding to LTA in a second ELISA assay.

Dilutions of purified A110 and A120 antibodies were compared for binding to LTA in an ELISA assay, using substantially the same protocol as above. The data for the anti-LTA ELISA using dilutions of purified antibodies are shown in Table 9.

TABLE 9

Binding of purified A110 and A120 to LTA-coated plates

| antibody concentration (ng/ml) | $A_{450}$ A110 | $A_{450}$ A120 |
|---|---|---|
| 8000 | 3.921 | 3.566 |
| 2000 | 3.922 | 3.078 |
| 500 | 3.960 | 1.445 |
| 125 | 3.838 | 0.422 |
| 31.25 | 2.398 | 0.131 |
| 7.8125 | 0.903 | 0.068 |
| 1.953 | 0.276 | 0.054 |
| PBS-T | 0.047 | 0.048 |

These data demonstrate that A110 has a greater affinity for S. aureus LTA than does A120. This difference is particularly striking at an antibody concentration of 125 ng/ml, where A120 gives an ELISA signal of 0.422, and A110 gives a signal that is nearly ten times stronger.

EXAMPLE 6

Comparison of the Opsonic Activity of Anti-LTA Antibodies A110 and A120

Purified human/mouse chimeric A110 and A120, and mouse M120 MAbs were assayed for their opsonic activity as described above, under the heading "Neutrophil-Mediated Opsonophagocytic Bactericidal Assay." Briefly, dilutions of purified A110, A120, or M120 antibodies were combined with neutrophils (PMNs) in the wells of a microtiter plate. Mid-log phase bacteria were added to each well, followed by immunoglobulin-depleted human serum, which serves as a source of complement (C). Samples were incubated for 2 hours at 37° C., and were then plated on blood agar and incubated overnight to determine the number of live bacteria remaining. The opsonic activity is expressed as "% killed", which is determined according to the following formula: % killed=100%−$N_{2hr}$/$N_{0hr}$, where $N_{2hr}$ is the number of colonies formed after a 2 hour incubation with antibody, PMNs, and C\ and $N_{0hr}$ is the number of colonies formed after a 0 hour incubation. Control reactions lacked one of the above components. Table 10 shows the results of the opsonic activity assay for antibodies A110, A120, and M120.

TABLE 10

Opsonic activity of A110, A120, and M120 against S. epidermidis strain Hay

| Antibody | Description | MAb conc, (µg/ml) | % killed |
|---|---|---|---|
| A110 | purified human/mouse chimeric | 100 | 99 |
| " | anti-LTA MAb | 50 | 96 |
| " | " | 10 | 96 |
| A120 | purified human/mouse chimeric | 100 | 100 |
| " | anti-LTA MAb | 50 | 99 |
| " | " | 10 | 94 |
| M120 | purified mouse anti-LTA MAb | 100 | 99 |
| " | | 50 | 97 |
| " | purified mouse anti-LTA MAb | 10 | 94 |
| PMNs alone | purified mouse anti-LTA MAb | N/A | 0 |
| C' alone | purified mouse anti-LTA MAb | N/A | 0 |
| PMNs + C' (no MAb) | purified mouse anti-LTA MAb | N/A | 14 |
| A110 alone | purified mouse anti-LTA MAb | 100 | 0 |
| A120 alone | purified mouse anti-LTA MAb | 100 | 0 |
| M120 alone | purified mouse anti-LTA MAb | 100 | 8 |

These data demonstrate that MAbs A110, A120, and M120 are equally active in the opsonic activity assay described herein. Thus, the chimerization of M120 to make A120 has little or no effect on the opsonic activity of the antibody, and the two different anti-LTA chimeric antibodies, A110 and A120, are of comparable activity.

EXAMPLE 7

Transient Production of Recombinant Chimeric Mouse/Human A120 Antibodies

The plasmids pJSB25, pJSB26 and pJSB27 were transected into COS cells grown in IMDM plus 10% fetal bovine serum, using Superfect (Qiagen) in 6 well tissue culture wells as described by the manufacturer. After two days the supernatant was assayed for the production of chimeric antibody and for the capability for the expressed antibody to bind to S. aureus LTA antigen.

Antibody production assays were preformed in 8-well strips from 96-well microtiter plates (Maxisorp F8; Nunc, Inc.) coated at a 1:500 dilution with a goat antihuman Fc (Pierce). The plates are covered with pressure sensitive film and incubated overnight at 4° C. Plates were then washed once with Wash solution (Imidazole/NaCl/0.4%Tween-20). One hundred microliters of culture supernatant dilutions were then applied to duplicate wells and allowed to incubate for 60 minutes on a plate rotator at room temperature. The plates were washed seven times with Wash solution. A Goat anti-Human IgG H+L−HRP (Zymed) conjugate was diluted 1:4000 in the sample/conjugate diluent. One hundred microliters was added to the samples, and then incubated on a plate rotator for 60 minutes at room temperature. The samples were washed as above and then incubated with 100 (xL/well of TMB developing substrate (BioFx) for 1 minute at room temperature. The binding reaction was stopped with 100 µUwell of Quench buffer (BioFx) and the absorbance value at 450 nm was determined using an automated microtiter plate ELISA reader. This assay (see FIG. 15) demonstrates that the transfection of cells with this plasmid construct results in the cells producing a molecule containing both human IgG and Kappa domains.

The supernatants were then assayed for the ability of the expressed antibodies to bind to lipoteichoic acid. The activity assays were preformed in 8-well strips from 96-well microtiter plates (Maxisorp F8; Nunc, Inc.) coated at 1 µg/mL with *S. aureus* LTA (Sigma) using PBS. The plates were covered and incubated overnight at 4° C. Plates were then washed once with PBS. One hundred microliters of culture supernatant dilutions were then applied to duplicate wells and allowed to incubate for 60 minutes on a plate rotator at room temperature. The plates were washed seven times with Wash solution. Goat anti-Human IgG H+L–HRP (Zymed) was diluted 1:4000 in the sample/conjugate diluent, and 100 ul were added to the samples, and then incubated on a plate rotator for 60 minutes at room temperature. The samples were washed as above and then incubated with 100 µL/well of TMB developing substrate (BioFx) for 10-15 minutes on a plate rotator at room temperature. The binding reaction was stopped with 100 µL/well of Quench buffer (BioFx) and the absorbance value at 450 nm was determined using an automated microtiter plate ELISA reader. As a positive control, the original human/mouse chimeric antibody A110 (produced by plasmid pJRS354) was used. This assay (FIG. 16) demonstrates that the transfection of cells with these plasmid constructs results in the cells producing a molecule that binds to the *S. aureus* LTA antigen.

These data demonstrate that the chimeric human antibody directed against LTA is opsonic and enhances survival against staphylococci. In addition, the antibody promotes clearance of the staphylococci from the blood. Thus antibody to LTA provides prophylactic and therapeutic capabilities against staphylococcal infections and vaccines using LTA or peptide mimeotopes of LTA that induce anti-LTA antibodies would also have prophylactic capabilities.

EXAMPLE 8

Human Antibodies that Bind LTA

Rather than humanizing a mouse antibody to minimize the HAMA response during treatment as described above, a skilled artisan can isolate a protective anti-LTA antibody that is fully human. There are a number of well-known alternative strategies one of ordinary skill in the art may use to produce completely human recombinant antibodies. One is the generation of antibodies using phage display technologies (59, 63). Specifically, human RNA is used to produce a cDNA library of antibody heavy and light chain fragments expressed on the surface of bacteriophage. These libraries can be used to probe against the antigen of interest (i.e., LTA) and the phage that bind, because of the antibody expressed on the surface, are then isolated. The DNA encoding the variable regions is sequenced and cloned for antibody expression.

Another method of producing human antibodies employs "humanized" mice. These transgenic mice have had their own antibody genes replaced with a portion of the human antibody gene complex so that upon inoculation with antigen, they produce human antibodies (57, 59, 60, 61, 63). The antibody producing cells that result can then be incorporated into the standard hybridoma technology for the establishment of specific monoclonal antibody producing cell lines.

Recombinant human antibodies are also produced by isolating antibody-producing B cells from human volunteers that have a robust anti-LTA response. Using fluorescence activated cell sorting (FACS) and fluorescently labeled LTA, cells producing the anti-LTA antibodies can be separated from the other cells. The RNA can then be extracted and the sequence of the reactive antibody variable regions determined (58, 62). The DNA sequence of the functional variable regions can be synthesized or cloned into mammalian expression vectors for large-scale human recombinant antibody production.

CONCLUSION

Monoclonal antibodies were raised in mice against *S. aureus* LTA. One hybridoma that produced antibodies that bound strongly to LTA in an ELISA assay was subcloned further. Hybridoma subclone 00-107GG12 ID12 produced an $IgG_{2a}$ monoclonal antibody with a kappa light chain that bound strongly to LTA. The antibody produced by this hybridoma was designated M120 (Example 1).

M120 was tested in an opsonophagocytic bacteriocidal assay for opsonic activity against *S. aureus* type 5 and *S. epidermidis* strain Hay. The antibody was mixed with PMNs and complement, which was derived from human serum that had been depleted of anti-*S. aureus* and anti-*S. epidermidis* antibodies, and then tested for activity against the bacteria. M120 showed opsonic activity against both *S. aureus* and *S. epidermidis*, killing 95% of *S. epidermidis* and an average of 82% of *S. aureus* at 200 µg/ml (Example 2, Tables 5 and 6). MAb-391.4, which was raised to UV-killed *S. aureus*, was tested for opsonic activity against *S. epidermidis* strain Hay in a similar assay, and showed 81.9% killing (Table 7).

The M120 variable regions were then cloned and sequenced, and the sequence compared to another anti-LTA antibody, M110. Surprisingly, M110 and M120 were found to share about 94% sequence identity at the amino acid level, and about 96% sequence identity at the nucleotide level. A third anti-LTA antibody, MAb-391.4, was also sequenced compared to the other two. The three antibodies share 88% sequence identity at the amino acid level. This high level of sequence identity may suggest that the antibodies bind to a common epitope on LTA (Example 3, FIGS. 9 and 10). Human/mouse chimeric antibodies were then made, fusing the heavy chain variable region of either M120 or M110 to a human IgG1 constant region, and the light chain variable region of either M120 or M110 to a human kappa light chain constant region. The human/mouse chimera of M120 is referred to as A120 and the human/mouse chimera of M110 is referred to as A110. Because of the similarity between the two antibodies, an antibody that contained the heavy chain of A110 and the light chain of A120, designated A120a, was made. Similarly, an antibody that contained the light chain of A110 and the heavy chain of A120, designated A120b, was also made (Example 4).

The human/mouse chimeric antibodies A120 and A110 were tested for their ability to bind to LTA in an ELISA assay. Both chimeric antibodies bound strongly to LTA, indicating that replacing the mouse constant regions with human constant regions had little effect on the binding properties of the antibodies (Example 5, Tables 8 and 9). Next, the opsonic activity of chimeric antibodies A110 and A120, and of M120, were compared in an opsonic assay against *S. epidermidis* strain Hay. All three antibodies showed at least 94% killing of S. epidermidis. These results show that the chimeric antibodies are strongly opsonic against S. epidermidis, and because they have a reduced HAMA response in humans, they should be suitable therapeutic molecules for fighting Gram-positive bacterial infections (Example 6, Table 10).

Finally, three of the chimeric antibodies, A120, A120a, and A120b were produced in COS cells and tested for the ability to bind to S. aureus LTA. All three chimeric antibodies bound to LTA in the ELISA assay, with A120 and A120a showing the strongest binding. These results suggest that M110 and M120 do bind to a similar or overlapping epitope on LTA, because antibodies that have variable regions from both retain the ability to bind to the antigen. These results may indicate that a particular epitope on LTA is able to elicit antibodies that are opsonic against S. aureus and S. epidermidis. This epitope may be more accessible than others, or may be positioned such that antibodies that are bound are ideally situated to attract the factors required for opsonization of the bacterium.

Previously, it was unclear whether a monoclonal antibody could enhance phagocytosis, because the polyclonal sera that were used contained many different antibodies that bound to many different epitopes on the surface of the bacteria, and the sum of this collective binding and activities may have accounted for the overall activity of the serum. Here, we demonstrate that monoclonal antibodies, which bind to a single epitope on the surface of bacteria, can be opsonic against that bacteria. We have also demonstrated that monoclonal antibodies raised against LTA can have that activity, and that those antibodies may be opsonic for a number of different types of Gram-positive bacteria.

Furthermore, we have shown that three different monoclonal antibodies, one of which was raised to whole S. epidermidis, one to purified and conjugated LTA from S. aureus, and one to whole UV-killed S. aureus, share a striking degree of homology. This level of homology between monoclonal antibodies that were raised to similar antigens in different mice has previously not been shown. In fact, it has long been believed that antibodies have evolved the ability to bind identical antigens using very dissimilar determinants to provide the body with a very broad antibody repertoire. The level of homology between the M110, M120, and MAb-391.4 variable regions may indicate that opsonic antibodies to LTA recognize a nearly identical epitope using nearly identical modes of binding, and that this mode of binding is important to their functional activity. Furthermore, the epitope to which the antibodies bind appears to be highly conserved between S. epidermidis and S. aureus, and may be common to most, if not all, Gram-positive bacteria. Monoclonal antibodies to this epitope may, therefore, be broadly opsonic against a wide range of bacteria, allowing researchers to develop a few antibodies that will have broad opsonic and protective activity against many Gram-positive bacteria.

The following literature references are herein specifically incorporated by reference:

1. Ames, B. N. 1966. Assay of inorganic phosphate, total phosphate and phosphatase, Methods in Enzymology 8: 115-118.
2. Ellman, G. L. 1959. Tissue Sulfhydryl Groups, Arch. Biochem. & Biophys. 82: 70
3. Endl, J.; Seidl, H P.; Fiedler, F.; and Schleifer, K. H. 1983. Chemical composition and structure of cell wall teichoic acid of staphylococci, Arch Microbiol, 135: 215-223.
4. Espersen, F.; Hertz, J. B.; and Hoiby, N. 1981. Cross-reactions between Staphylococcus epidermis and 23 other bacterial species, Ada Path. Microbial. Scand, Sect. B. 89: 253-260.
5. Exley A. R.; Cohen J.; Buurman W.; Owen R.; Hanson G.; Lumley J.; Aulakh J. M.; Bodmer M.; Riddell A.; Stephens S.; et al. 1990. Monoclonal antibody to TNF in severe septic shock, Lancet 335: 1275-1277.
6. Fattom A.; Shepherd S.; Karakawa W. 1992. Capsular polysaccharide serotyping scheme for Staphylococcus epidermidis, J. Clin. Micro. 30: 3270-3273.
7. Fischer, Gerald W. Broadly reactive opsonic antibodies that react with common staphylococcal antigens, U.S. Pat. No. 5,571,511, issued Nov. 5, 1996.
8. Fischer, Gerald W. Directed human immune globulin for the prevention and treatment of staphylococcal infections, U.S. Pat. No. 5,955,074, issued Sep. 21, 1999.
9. Fischer W.; Koch H. U.; Haas R. 1983. Improved preparation of lipoteichoic acids, Eur. J. Biochem. 133: 523-530.
10. Fleer, A.; Senders R. C.; Visser M. R.; Bijlmer R. P.; Gerards L. J.; Kraaijeveld C. A.; Verhoef J. 1983. Septicemia due to coagulase-negative staphylococci in a neonatal intensive care unit: clinical and bacteriological features and contaminated parenteral fluids as a source of sepsis, Pediatr. Infect Dis. 2:426-431.
11. Fournier, Jean-Michel. 1991. Staphylococcus Aureus, Vaccines and Immunotherapy, Ch. 13, pp. 166 -171.
12. Garrett, Laurie. 1994. The Revenge of the Germs or Just Keep Inventing New Drugs, The Coming Plague, Ch. 13, Farrar, Straus and Giroux, N.Y., (ed.), pp. 411-456.
13. Genarro, A. (ed.) 1990. Remington's Pharmaceutical Sciences, 1$8^{th}$ Edition, Mack Publishing, Easton, Pa.
14. Hancock, I. C. 1997. Bacterial cell surface carbohydrates: Structure and assembly, Biochem. Soc. Trans. 25: 183-187.
15. Jendeberg, Lena; Nilsson, Peter; Larsson, Antonella; Denker, Per; Uhlen, Mathias; Nilsson, Bjorn; Nygren, Per-Ake. 1997. Engineering of Fc1 and Fc3 from human immunoglobulin G to analyse subclass specificity for Staphylococcal Protein A, J. Immunol. Methods 201: 25-34.
16. Kojima Y.; Tojo M.; Goldmann D. A.; Tosteson T. D.; Pier G. B. 1990. Antibody to the capsular polysaccharide/adhesion protects rabbits against catheter-related bacteremia due to coagulase-negative staphylococci, J. Infect Dis. 162: 435-441.
17. Krieger, Monty; Joiner, Keith A. Method for treating Gram-positive septicemia, U.S. Pat. No. 5,624,904, issued Apr. 29, 1997.
18. Lee, J. C. 1996. The prospects for developing a vaccine against Staphylococcus aureus, Trends in Micro. 4: 162-66.
19. LoBuglio A. F.; Wheeler R. H.; Trang J.; Haynes A.; Rogers K.; Harvey E. B.; Sun L; Ghrayeb J.; Khazaeli M. B. 1989. Mouse/human chimeric monoclonal antibody in man: kinetics and immune response, P.N.A.S. 86: 4220-4224.
20. Nakamura, K. et al. 1999. Uptake and release of budesonide from mucoadhesive, pH-sensitive copolymers and their application to nasal delivery. J. Control. Release 61:329-335.
21. Natsume, H., S. Iwata, K. Ohtak, M. Miyamoto, M. Yamaguchi, K. Hosoya, and D. Kobayashi. 1999. Screening of cationic compounds as an absorption enhancer for nasal drug delivery. Int. J. Pharma. 185:1-12.
22. Naumova, I. B.; Kuznetsov, V. D.; Kudrina, K. S.; and Bezzubenkova, A. P. 1980. The Occurrence of Teichoic Acids in Streptomycetes, Arch. Microbiol. 126:71-75.
23. Navarre, William Wiley and Schneewind, Olaf. 1999. Surface proteins of Gram-positive bacteria and mechanisms of their targeting to the cell wall envelope, Microbiology and Molecular Biology Reviews 63:174-229.

24. Osland, Arve; Grov, Arne; and Oeding, Per. 1980. Immunochemical analysis of the teichoic acid from *Staphylococcus simulans*, *Acta Path. Microbiol. Scand*, Sect. B., 88:121-123.
25. Patrick, C. C. 1990. Coagulase-negative staphylococci: Pathogens with increasing clinical Significance, *J. Pediatr.* 116:497-507.
26. Peterson, Phillip K.; Verhoef, Jan; Sabath, L. D.; and Quie, Paul G. 1977. Effect of Protein A on staphylococcal opsonization, *Infection and Immunity* 15: 760-764.
27. Peterson, Phillip K.; Wilkinson, Brian J.; Kim, Youngki; Schmeling, David; and Quie, Paul G. 1978. Influence of Encapsulation on Staphylococcal Opsonization and Phagocytosis by Human Polymorphonuclear Leukocytes, *Infection and Immunity* 19: 943-949.
28. Quie, Paul G.; Hill, Harry R.; and Davis, Todd A. 1974. Defective phagocytosis of Staphylococci, *Annals New York Academy of Sciences*, pp. 233-243.
29. Ramkissoon-Ganorkar, C. et al. 1999. Modulating insulin-release profile from pH/thermosensivite polymeric beads through polymer molecular weight. *J. Contr. Release* 59:287-298.
30. Raynor, Robert H.; Scott, David F.; and Best, Gary K. 1981. Lipoteichoic acid inhibition of phagocytosis of *Staphylococcus aureus* by Human Polymorphonuclear Leukocytes, *Clinical Immunology and Immunopathology* 19:181-189.
31. Romero-Vivas J.; Rubio M.; Fernandez C; Picazo J. J. 1995. Mortality associated with nosocomial bacteremia due to methicillin-resistant *Staphylococcus aureus, Clin. Infect. Dis.* 21: 1417-23.
32. Salton, M. R. J. 1994. The Bacterial Cell Envelope—A Historical Perspective, in J.-M. Ghuyson and R. Hakenbeck (ed.), *Bacterial Cell Wall*, Elsevier Science BV, Amsterdam, pp. 1-22.
33. Schwab, U. E., A. E. Wold, J. L. Carson, M. W. Leigh, P.-W. Cheng, P. H. Gilligan and T. F. Boat. 1993. Increased adherence of *Staphylococcus aureus* from cystic fibrosis lungs to airway epithelial cells. *Am. Rev. Respir. Dis.* 148: 365-369.
34. Shulman, M.; Wilde, C D.; Kohler, G. 1978. A Better Cell Line for Making Hybridomas Secreting Specific Antibodies, *Nature* 276: 269-270.
35. Soto, N., A. Vaghjimal, A. Stahl-Avicolli, J. Protic, L. Lutwick and E. Chapnick. 1999. Bacitracin versus mupirocin for *Staphylococcus aureus* nasal colonization. *Infect. Cont. Hosp. Epidem.* 20:351-353.
36. Suzuki, Y. and Y. Makino. 1999. Mucosal drug delivery using cellulose derivative as a functional polymer. *J. Control. Release.* 62:101-107.
37. Takada H.; Kawabata Y.; Arakaki R.; Kusumoto S.; Fukase K.; Suda Y.;
Yoshimura T.; Kokeguchi S.; Kato K.; Komuro T.; et al. 1995. Molecular and structural requirements of a lipoteichoic acid from Enterococcus hirae ATCC 9790 for cytokine-inducing, antitumor, and antigenic activities, *Infection and Immunity* 63: 57-65.
38. Takeda S.; Pier G.B.; Kojima Y.; Tojo M.; Muller E.; Tosteson T.; Goldmann D.A. 1991. Protection against endocarditis due to *Staphylococcus epidermidis* by immunization with capsular polysaccharide/adhesin, *Circulation* 86: 2539-2546.
39. Timmerman C. P.; Besnier J. M.; De Graaf L.; Torensma R.; Verkley A. J.; Fleer A.; VerhoefJ. 1991. Characterisation and functional aspects of monoclonal antibodies specific for surface proteins of coagulase-negative staphylococci, *J. Med. Micro.* 35: 65-71.
40. Tomasz, Alexander. 2000. The Staphylococcal Cell Wall, in V. A. Fischetti et al. (ed.) *Gram-Positive Pathogens*, Ch. 36, pp. 351-355.
41. Waldvogel, Francis A. 1990. *Staphylococcus Aureus* (Including Toxic Shock Syndrome), in Mandell, G. L. et al. (ed.) *Principles and Practices of Infectious Diseases, Third Edition*, Churchill Livingstone, N.Y., Ch. 173, pp. 1489-1510.
42. West, Timothy E.; Cantey, J. R.; Apicella, Michael A.; and Burdash, N. M. 1983. Detection of anti-teichoic acid immunoglobulin G antibodies in experimental *Staphylococcus epidermidis* endocarditis, *Infection and Immunity* 42: 1020-1026.
43. Wortham, Charles; Grinberg, Luba; Kaslow, David C; Briles, David E.; McDaniel, Larry S.; Lees, Andrew; Flora, Michael; Snapper, Clifford M.; and Mond, James J. 1998. Enhanced protective antibody response to PspA after intranasal or subcutaneous injections of PspA genetically fused to Granulocyte-Macrophage Colony-Stimulating Factor or lnterleukin-2, *Infection and Immunity* 66:1513-1520.
44. Sambrook, Joseph; Russell, David W. 1989. *Molecular Cloning: A Laboratory Manual*, $2^{nd}$ Ed., Cold Spring Harbor Press, Cold Spring Harbor, N.Y.
45. Ausubel et al. (ed.) 1989. *Current Protocols in Molecular Biology*, John Wiley & Sons.
46. Merkus, F. W., J. C. Verhoef, N. G. Schipper, and E. Marttin. 1999. Cyclodextrins in nasal drug delivery. *Advan. Drug Deliv. Rev.* 36:41-57.
47. Kiser, Kevin B.; Cantey-Kiser, Jean M.; Lee, Jean C. 1999. Development and characterization of a *Staphylococcus aureus* nasal colonization model in mice. *Infection and Immunity* 67: 5001-5006.
48. Bartal, Arie H.; Hirshaut, Yashar. 1987. Current Methods in Hybridoma Formation Bartal, A. H. et al. (ed.) *Methods of Hybridoma Formation*, Humana Press, Clifton, N.J.
49. De Kimpe, S. J., M. Kengatharan, C. Thiemermann, J. R. Vane. 1995. The cell wall components peptidoglycan and lipoteichoic acid from *S. aureus* act in synergy to cause shock and multiple organ failure. *Proc. Nat. Acad. Sci. (USA)* 92:10359-10363.
50. Carruthers, M. M., W. J. Kabat. 1983. Mediation of staphylococcal adherence to mucosal cells by lipoteichoic acid. *Infect Immun.* 40: 444-6.
51. Chugh T D, Burns G J, Shuhaiber H J, Bahr G M. 1990. Adherence of *Staphylococcus epidermidis* to fibrin-platelet clots in vitro mediated by lipoteichoic acid. *Infect Immun.* 58: 315-9.
52. Granato D, Perotti F, Masserey I, Rouvet M, Golliard M, Servin A, Brassart D. 1999. Cell surface-associated lipoteichoic acid acts as an adhesion factor for attachment of Lactobacillus johnsonii La1 to human enterocyte-like Caco-2 cells. *Appl Environ Microbiol.* 65:1071-7.
53. Nealon T J, Mattingly S J. 1984. Role of cellular lipoteichoic acids in mediating adherence of serotype III strains of group B streptococci to human embryonic, fetal, and adult epithelial cells. *Infect Immun.* 43: 523-30.
54. Teti G, Tomasello F, Chiofalo M S, Orefici G, Mastroeni P. 1987. Adherence of group B streptococci to adult and neonatal epithelial cells mediated by lipoteichoic acid. *Infect Immun.* 55: 3057-64.
55. Nickerson, K. G.; Tao, M.-H.; Chen, H.-T.; Larrick, J.; Kabat, E. A. 1995. Human and mouse monoclonal antibodies to blood group A substance, which are nearly identical immunochemically, use radically different primary sequences. *J. Biol. Chem.* 270: 12457-12465.

56. Fleury, D.; Daniels, R. S.; Skehel, J. J.; Knossow, M.; Bizebard, T. 2000. Structural evidence for recognition of a single epitope by two distinct antibodies. *Proteins* 40: 572-578.
57. Green, L. L, M. C. Hardy, et al. (1994). "Antigen-specific human monoclonal antibodies from mice engineered with human Ig heavy and light chain YACs." *Nat Genet* 7(1): 13-21.
58. Kantor, A. B., C. E. Merrill, et al. (1995). "Development of the antibody repertoire as revealed by single-cell PCR of FACS-sorted B-cell subsets." *Ann NY Acad Sci* 764: 224-7.
59. Low, N. M., P. H. Holliger, et al. (1996). "Mimicking somatic hypermutation: affinity maturation of antibodies displayed on bacteriophage using a bacterial mutator strain." *J Mol Biol* 260(3): 359-68.
60. Wagner, S. D., A. V. Popov, et al. (1994). "The diversity of antigen-specific monoclonal antibodies from transgenic mice bearing human immunoglobulin gene miniloci." *Eur J Immunol* 24(11): 2672-81.
61. Wagner, S. D., G. T. Williams, et al. (1994). "Antibodies generated from human immunoglobulin miniloci in transgenic mice." *Nucleic Acids Res* 22(8): 1389-93.
62. Wang, X. and B. D. Stollar (2000). "Human immunoglobulin variable region gene analysis by single cell RT-PCR." *J Immunol Methods* 244(1-2): 217-25.
63. Winter, G., A. D. Griffiths, et al. (1994). "Making antibodies by phage display technology." *Annu Rev Immunol* 12: 433-55.
64. Borrebaeck, Carl A. K. 1995. Antibody Engineering, 2.sup.nd Ed., Oxford University Press, NY.
65. Harlow, Ed; Lane, David. 1988. Antibodies: A Laboratory Manual, Cold Spring Harbor Press, Cold Spring Harbor, N.Y.

Having now fully described the invention, it will be appreciated by those skilled in the art that the invention can be performed within a range of equivalents and conditions without departing from the spirit and scope of the invention and without undue experimentation. In addition, while the invention has been described in light of certain embodiments and examples, the inventors believe that it is capable of further modifications. This application is intended to cover any variations, uses, or adaptations of the invention which follow the general principles set forth above.

Other embodiments of the invention will be apparent to those skilled in the art from consideration of the specification and practice of the invention disclosed herein. It is intended that the specification and examples be considered as exemplary only, with a true scope and spirit of the invention being indicated by the following claims.

What is claimed is:

1. An isolated nucleic acid molecule comprising a nucleotide sequence encoding a monoclonal antibody light chain, or variable region thereof, the light chain or variable region comprising the sequence as set forth in residues 1-106 of SEQ ID NO:10.

2. An isolated nucleic acid molecule comprising a nucleotide sequence encoding a monoclonal antibody heavy chain, or variable region thereof, the heavy chain or variable region comprising the sequence as set forth in residues 1-123 of SEQ ID NO:12.

3. An isolated nucleic acid molecule comprising a nucleotide sequence encoding a monoclonal antibody light chain, or variable region thereof, the light chain or variable region comprising the complementarity determining regions (CDRs) from the antibody light chain variable region sequence set forth as SEQ ID NO:10.

4. An isolated nucleic acid molecule comprising a nucleotide sequence encoding a monoclonal antibody heavy chain, or variable region thereof, the heavy chain or variable region comprising the complementarity determining regions (CDRs) from the antibody heavy chain variable region sequence set forth as SEQ ID NO:12.

5. An isolated nucleic acid molecule comprising a nucleotide sequence encoding a monoclonal antibody light chain variable region amino acid sequence and a monoclonal antibody heavy chain variable region amino acid sequence selected from the group consisting of SEQ ID NOs. 10 and 12, SEQ ID NOs. 10 and 17, and SEQ ID NOs. 16 and 12.

6. An isolated nucleic acid molecule comprising a nucleotide sequence encoding a monoclonal antibody light chain, or variable region thereof, the light chain or variable region thereof comprising the complementary determining regions (CDRs) from the light chain of the monoclonal antibody produced by the hybridoma deposited at the ATCC under Accession number PTA-3644.

7. An isolated nucleic acid molecule comprising a nucleotide sequence encoding a monoclonal antibody light chain variable region comprising CDRs from SEQ ID NO: 10 and a monoclonal antibody heavy chain variable region comprising CDRs from SEQ ID NO: 12.

8. An isolated nucleic acid molecule comprising a nucleotide sequence encoding a monoclonal antibody light chain variable region comprising CDRs from SEQ ID NO: 10 and a monoclonal antibody heavy chain variable region comprising CDRs from SEQ ID NO: 17.

9. An isolated nucleic acid molecule comprising a nucleotide sequence encoding a monoclonal antibody light chain variable region comprising CDRs from SEQ ID NO: 16 and a monoclonal antibody heavy chain variable region comprising CDRs from SEQ ID NO: 12.

10. An isolated nucleic acid molecule comprising a nucleotide sequence encoding a monoclonal antibody light chain variable region amino acid sequence set forth in SEQ ID No: 10 and a monoclonal antibody heavy chain variable region amino acid sequence set forth in SEQ ID No:12 or 17.

11. An isolated nucleic acid molecule comprising a nucleotide sequence encoding a monoclonal antibody heavy chain variable region amino acid sequence set forth in SEQ ID NO:12 and a monoclonal antibody light chain variable region amino acid sequence set forth in SEQ ID No:10 or 16.

12. An isolated nucleic acid molecule comprising a nucleotide sequence encoding the M120 monoclonal antibody heavy chain, or variable region thereof, produced by the hybridoma deposited at the ATCC under Accession number PTA-3644.

13. An isolated nucleic acid molecule comprising a nucleotide sequence encoding the M120 antibody light chain, or variable region thereof, produced by the hybridoma deposited at the ATCC under Accession number PTA-3644.

14. An isolated vector comprising a nucleotide sequence encoding a monoclonal antibody light chain, or variable region thereof, the light chain or variable region comprising the sequence as set forth in residues 1-106 of SEQ ID NO:10.

15. An isolated vector comprising a nucleotide sequence encoding a monoclonal antibody heavy chain, or variable region thereof, the heavy chain or variable region comprising the sequence as set forth in residues 1-123 of SEQ ID NO:12.

16. An isolated vector comprising the nucleic acid molecule of claim 3.

17. The isolated vector of claim 16, further comprising a nucleic acid molecule comprising a nucleotide sequence encoding a monoclonal antibody heavy chain, or variable region thereof, comprising the complementarity determining regions (CDRs) from the antibody heavy chain variable region sequence set forth as SEQ ID NO: 12.

18. An isolated vector comprising the isolated nucleic acid molecule of claim 5.

19. An isolated cell line comprising a first vector, said first vector comprising the vector of claim 16.

20. The isolated cell line of claim 19, further comprising a second vector, said second vector comprising an isolated nucleotide sequence encoding comprising the complementarity determining regions (CDRs) from the antibody heavy chain variable region sequence set forth as SEQ ID NO:12.

21. An isolated cell line comprising the vector of claim 18.

22. An isolated nucleic acid molecule comprising the nucleotide sequence set forth as SEQ ID NO:11.

23. An isolated nucleic acid molecule comprising the nucleotide sequence set forth as SEQ ID NO:13.

24. A method of producing a monoclonal antibody, or an antigen-binding fragment thereof, comprising culturing the cell line of claim 20 under conditions such that the antibody or antigen-binding fragment is produced, and isolating said antibody or antigen-binding fragment from the cell line or culture.

25. A method of producing a monoclonal antibody, or an antigen-binding fragment thereof, comprising culturing the cell line of claim 21 under conditions such that the antibody or antigen-binding fragment is produced and isolating said antibody or antigen-binding fragment from the cell line or culture.

26. An isolated nucleic acid molecule comprising a nucleotide sequence encoding a monoclonal antibody heavy chain, or variable region thereof, the heavy chain or variable region thereof comprising the complementary determining regions (CDRs) from the heavy chain of the monoclonal antibody produced by the hybridoma deposited at the ATCC under Accession number PTA-3644.

27. An isolated vector comprising a nucleotide sequence encoding a monoclonal antibody light chain, or variable region thereof, the light chain or variable region thereof comprising the sequence set forth in residues 1-106 of SEQ ID NO:10 and a heavy chain, or variable region thereof, the heavy chain or variable region thereof comprising the sequence set forth in residues 1-123 of SEQ ID NO:12.

28. An isolated vector comprising the isolated nucleic acid molecule of claim 10.

29. An isolated vector comprising the isolated nucleic acid molecule of claim 11.

30. An isolated cell line comprising the vector of claim 28.

31. An isolated cell line comprising the vector of claim 29.

* * * * *

SEQUENCE LISTING

```
<160> NUMBER OF SEQ ID NOS: 22

<210> SEQ ID NO 1
<211> LENGTH: 40
<212> TYPE: DNA
<213> ORGANISM: Artificial Sequence
<220> FEATURE:
<223> OTHER INFORMATION: Description of Artificial Sequence: Primer

<400> SEQUENCE: 1
tgttttcgta cgtcttgtcc gargtrmagc tksakgagwc                          40

<210> SEQ ID NO 2
<211> LENGTH: 40
<212> TYPE: DNA
<213> ORGANISM: Artificial Sequence
<220> FEATURE:
<223> OTHER INFORMATION: Description of Artificial Sequence: Primer

<400> SEQUENCE: 2
tgttttcgta cgtcttgtcc gavgtgmwgc tkgtggagwc                          40

<210> SEQ ID NO 3
<211> LENGTH: 32
<212> TYPE: DNA
<213> ORGANISM: Artificial Sequence
<220> FEATURE:
<223> OTHER INFORMATION: Description of Artificial Sequence: Primer

<400> SEQUENCE: 3
taccgtaccg gtgacattgt gmtgwcmcar tc                                  32

<210> SEQ ID NO 4
<211> LENGTH: 32
<212> TYPE: DNA
<213> ORGANISM: Artificial Sequence
<220> FEATURE:
<223> OTHER INFORMATION: Description of Artificial Sequence: Primer
```

-continued

```
<400> SEQUENCE: 4
taccgtaccg gtgayatyma gatgacmcag wc                                      32

<210> SEQ ID NO 5
<211> LENGTH: 23
<212> TYPE: DNA
<213> ORGANISM: Artificial Sequence
<220> FEATURE:
<223> OTHER INFORMATION: Description of Artificial Sequence: Primer

<400> SEQUENCE: 5
gcacctccag atgttaactg ctc                                                23

<210> SEQ ID NO 6
<211> LENGTH: 22
<212> TYPE: DNA
<213> ORGANISM: Artificial Sequence
<220> FEATURE:
<223> OTHER INFORMATION: Description of Artificial Sequence: Primer

<400> SEQUENCE: 6
ctggacaggg mtccakagtt cc                                                 22

<210> SEQ ID NO 7
<211> LENGTH: 27
<212> TYPE: DNA
<213> ORGANISM: Artificial Sequence
<220> FEATURE:
<223> OTHER INFORMATION: Description of Artificial Sequence: Primer

<400> SEQUENCE: 7
aaaaccccgt acgtcttgtc cgaagtg                                            27

<210> SEQ ID NO 8
<211> LENGTH: 32
<212> TYPE: DNA
<213> ORGANISM: Artificial Sequence
<220> FEATURE:
<223> OTHER INFORMATION: Description of Artificial Sequence: Primer

<400> SEQUENCE: 8
atctgggaat tctgaggaga cggtgactga gg                                      32

<210> SEQ ID NO 9
<211> LENGTH: 27
<212> TYPE: DNA
<213> ORGANISM: Artificial Sequence
<220> FEATURE:
<223> OTHER INFORMATION: Description of Artificial Sequence: Primer

<400> SEQUENCE: 9
atatttaccg gtgacattgt gctgtcc                                            27

<210> SEQ ID NO 10
<211> LENGTH: 106
<212> TYPE: PRT
<213> ORGANISM: Artificial Sequence
<220> FEATURE:
<223> OTHER INFORMATION: Description of Artificial Sequence: Synthetic
      A120 light chain antibody

<400> SEQUENCE: 10

Asp Ile Val Leu Ser Gln Ser Pro Ala Ile Leu Ser Ala Ser Pro Gly
1               5                   10                  15
```

```
Glu Lys Val Thr Met Thr Cys Arg Ala Ser Ser Val Ser Tyr Met
            20                  25                  30

His Trp Tyr Gln Gln Lys Pro Gly Ser Ser Pro Lys Pro Trp Ile Tyr
        35                  40                  45

Ala Thr Ser Asn Leu Ala Ser Gly Val Pro Ala Arg Phe Ser Gly Ser
    50                  55                  60

Gly Ser Gly Thr Ser Tyr Ser Leu Thr Ile Ser Arg Val Glu Ala Glu
65                  70                  75                  80

Asp Ala Ala Thr Tyr Tyr Cys Gln Gln Trp Ser Ser Asn Pro Pro Thr
                85                  90                  95

Phe Gly Gly Gly Thr Lys Leu Glu Ile Lys
            100                 105

<210> SEQ ID NO 11
<211> LENGTH: 318
<212> TYPE: DNA
<213> ORGANISM: Artificial Sequence
<220> FEATURE:
<223> OTHER INFORMATION: Description of Artificial Sequence: Synthetic
      DNA encoding A120 light chain antibody
<220> FEATURE:
<221> NAME/KEY: CDS
<222> LOCATION: (1)..(318)

<400> SEQUENCE: 11 gac att gtg ctg tcc cag tct cca gca atc ctg tct gca tct cca ggg      48
Asp Ile Val Leu Ser Gln Ser Pro Ala Ile Leu Ser Ala Ser Pro Gly
1               5                   10                  15 gag aag gtc aca atg act tgc agg gcc agc tca agt gta agt tac atg      96
Glu Lys Val Thr Met Thr Cys Arg Ala Ser Ser Val Ser Tyr Met
            20                  25                  30 cac tgg tac cag cag aag cca gga tcc tcc ccc aaa ccc tgg att tat     144
His Trp Tyr Gln Gln Lys Pro Gly Ser Ser Pro Lys Pro Trp Ile Tyr
        35                  40                  45 gcc aca tcc aac ctg gct tct gga gtc cct gct cgc ttc agt ggc agt     192
Ala Thr Ser Asn Leu Ala Ser Gly Val Pro Ala Arg Phe Ser Gly Ser
    50                  55                  60 ggg tct ggg acc tct tac tct ctc aca atc agc aga gtg gag gct gaa     240
Gly Ser Gly Thr Ser Tyr Ser Leu Thr Ile Ser Arg Val Glu Ala Glu
65                  70                  75                  80 gat gct gcc act tat tac tgc cag cag tgg agt agt aac cca ccg acg     288
Asp Ala Ala Thr Tyr Tyr Cys Gln Gln Trp Ser Ser Asn Pro Pro Thr
                85                  90                  95 ttc ggt gga ggc acc aag ctg gaa atc aaa                             318
Phe Gly Gly Gly Thr Lys Leu Glu Ile Lys
            100                 105

<210> SEQ ID NO 12
<211> LENGTH: 123
<212> TYPE: PRT
<213> ORGANISM: Artificial Sequence
<220> FEATURE:
<223> OTHER INFORMATION: Description of Artificial Sequence: Synthetic
      A120 heavy chain antibody

<400> SEQUENCE: 12

Glu Val Met Leu Val Glu Ser Gly Glu Gly Leu Val Gln Pro Lys Gly
1               5                   10                  15

Ser Leu Lys Leu Ser Cys Ala Ala Ser Gly Phe Thr Phe Asn Thr Tyr
            20                  25                  30

Ala Met Asn Trp Val Arg Gln Ala Pro Gly Lys Gly Leu Glu Trp Val
        35                  40                  45
```

```
Ala Arg Ile Arg Ser Lys Ser Asn Asn Tyr Ala Thr Tyr Tyr Ala Asp
    50                  55                  60

Ser Val Lys Asp Arg Phe Thr Ile Ser Arg Asp Asp Ser Gln Ser Met
65                  70                  75                  80

Leu Tyr Leu Gln Met Asn Asn Leu Lys Thr Glu Asp Thr Ala Met Tyr
                85                  90                  95

Tyr Cys Val Arg Arg Gly Gly Lys Glu Thr Asp Tyr Ala Met Asp Tyr
            100                 105                 110

Trp Gly Gln Gly Thr Ser Val Thr Val Ser Ser
        115                 120
```

<210> SEQ ID NO 13
<211> LENGTH: 369
<212> TYPE: DNA
<213> ORGANISM: Artificial Sequence
<220> FEATURE:
<223> OTHER INFORMATION: Description of Artificial Sequence: Synthetic
      DNA encoding A120 heavy chain antibody
<220> FEATURE:
<221> NAME/KEY: CDS
<222> LOCATION: (1)..(369)

<400> SEQUENCE: 13

```
gaa gtg atg ctt gtg gag tct ggt gaa gga ttg gtg cag cct aaa ggg     48
Glu Val Met Leu Val Glu Ser Gly Glu Gly Leu Val Gln Pro Lys Gly
1               5                   10                  15 tca ttg aaa ctc tca tgt gca gcc tct gga ttc acc ttc aat acc tac     96
Ser Leu Lys Leu Ser Cys Ala Ala Ser Gly Phe Thr Phe Asn Thr Tyr
            20                  25                  30 gcc atg aac tgg gtc cgc cag gct cca gga aag ggt ttg gaa tgg gtt    144
Ala Met Asn Trp Val Arg Gln Ala Pro Gly Lys Gly Leu Glu Trp Val
        35                  40                  45 gct cgc ata aga agt aaa agt aat aat tat gca aca tat tat gcc gat    192
Ala Arg Ile Arg Ser Lys Ser Asn Asn Tyr Ala Thr Tyr Tyr Ala Asp
    50                  55                  60 tca gtg aaa gac agg ttc acc atc tcc aga gat gat tca caa agc atg    240
Ser Val Lys Asp Arg Phe Thr Ile Ser Arg Asp Asp Ser Gln Ser Met
65                  70                  75                  80 ctc tat ctg caa atg aac aac ttg aag act gag gac aca gcc atg tat    288
Leu Tyr Leu Gln Met Asn Asn Leu Lys Thr Glu Asp Thr Ala Met Tyr
                85                  90                  95 tac tgt gtg aga cgg ggt ggt aaa gag act gac tat gct atg gac tac    336
Tyr Cys Val Arg Arg Gly Gly Lys Glu Thr Asp Tyr Ala Met Asp Tyr
            100                 105                 110 tgg ggt caa gga acc tca gtc acc gtc tcc tca                        369
Trp Gly Gln Gly Thr Ser Val Thr Val Ser Ser
        115                 120
```

<210> SEQ ID NO 14
<211> LENGTH: 318
<212> TYPE: DNA
<213> ORGANISM: Artificial Sequence
<220> FEATURE:
<223> OTHER INFORMATION: Description of Artificial Sequence: Synthetic
      DNA A110 light chain antibody

<400> SEQUENCE: 14

```
gatatcgttc tctcccagtc tccagcaatc ctgtctgcat ctccagggga aaaggtcaca     60
atgacttgca gggccagctc aagtgtaaat tacatgcact ggtaccagca gaagccagga    120
tcctccccca aaccctggat ttctgccaca tccaacctgg cttctggagt ccctgctcgc    180
```

-continued

```
ttcagtggca gtgggtctgg gacctcttac tctctcacaa tcagcagagt ggaggctgaa      240
gatgctgcca cttattactg ccagcagtgg agtagtaacc cacccacgtt cggaggggggg     300 accatgctgg aaataaaa                                                    318
```

<210> SEQ ID NO 15
<211> LENGTH: 369
<212> TYPE: DNA
<213> ORGANISM: Artificial Sequence
<220> FEATURE:
<223> OTHER INFORMATION: Description of Artificial Sequence: Synthetic
      DNA A110 heavy chain antibody

<400> SEQUENCE: 15

```
gaagtgatgc tggtggagtc tggtggagga ttggtgcagc ctaaagggtc attgaaactc       60
tcatgtgcag cctctggatt caccttcaat aactacgcca tgaattgggt ccgccaggct      120
ccaggaaagg gtttggaatg ggttgctcgc ataagaagta aagtaataa ttatgcaaca       180 tttatgccg attcagtgaa agacaggttc accatctcca gagatgattc acaaagcatg      240
ctctatctgc aaatgaacaa cttgaaaact gaggacacag ccatgtatta ctgtgtgaga      300
cggggggctt cagggattga ctatgctatg gactactggg gtcaaggaac ctcactcacc      360
gtctcctca                                                              369
```

<210> SEQ ID NO 16
<211> LENGTH: 106
<212> TYPE: PRT
<213> ORGANISM: Artificial Sequence
<220> FEATURE:
<223> OTHER INFORMATION: Description of Artificial Sequence: Synthetic
      DNA A110 light chain antibody

<400> SEQUENCE: 16

Asp Ile Val Leu Ser Gln Ser Pro Ala Ile Leu Ser Ala Ser Pro Gly
1               5                   10                  15

Glu Lys Val Thr Met Thr Cys Arg Ala Ser Ser Ser Val Asn Tyr Met
            20                  25                  30

His Trp Tyr Gln Gln Lys Pro Gly Ser Ser Pro Lys Pro Trp Ile Ser
        35                  40                  45

Ala Thr Ser Asn Leu Ala Ser Gly Val Pro Ala Arg Phe Ser Gly Ser
    50                  55                  60

Gly Ser Gly Thr Ser Tyr Ser Leu Thr Ile Ser Arg Val Glu Ala Glu
65                  70                  75                  80

Asp Ala Ala Thr Tyr Tyr Cys Gln Gln Trp Ser Ser Asn Pro Pro Thr
            85                  90                  95

Phe Gly Gly Gly Thr Met Leu Glu Ile Lys
            100                 105

<210> SEQ ID NO 17
<211> LENGTH: 123
<212> TYPE: PRT
<213> ORGANISM: Artificial Sequence
<220> FEATURE:
<223> OTHER INFORMATION: Description of Artificial Sequence: Synthetic
      DNA A110 heavy chain antibody

<400> SEQUENCE: 17

Glu Val Met Leu Val Glu Ser Gly Gly Gly Leu Val Gln Pro Lys Gly
1               5                   10                  15

Ser Leu Lys Leu Ser Cys Ala Ala Ser Gly Phe Thr Phe Asn Asn Tyr
            20                  25                  30

```
Ala Met Asn Trp Val Arg Gln Ala Pro Gly Lys Gly Leu Glu Trp Val
        35                  40                  45

Ala Arg Ile Arg Ser Lys Ser Asn Asn Tyr Ala Thr Phe Tyr Ala Asp
    50                  55                  60

Ser Val Lys Asp Arg Phe Thr Ile Ser Arg Asp Asp Ser Gln Ser Met
65                  70                  75                  80

Leu Tyr Leu Gln Met Asn Asn Leu Lys Thr Glu Asp Thr Ala Met Tyr
                85                  90                  95

Tyr Cys Val Arg Arg Gly Ala Ser Gly Ile Asp Tyr Ala Met Asp Tyr
            100                 105                 110

Trp Gly Gln Gly Thr Ser Leu Thr Val Ser Ser
        115                 120
```

<210> SEQ ID NO 18
<211> LENGTH: 45
<212> TYPE: DNA
<213> ORGANISM: Artificial Sequence
<220> FEATURE:
<223> OTHER INFORMATION: Description of Artificial Sequence: Primer

<400> SEQUENCE: 18

```
ataggattcg aaaagtgtac ttacgtttga tttccagctt ggtgc              45
```

<210> SEQ ID NO 19
<211> LENGTH: 318
<212> TYPE: DNA
<213> ORGANISM: Artificial Sequence
<220> FEATURE:
<223> OTHER INFORMATION: Description of Artificial Sequence: Synthetic
      DNA 391.4 light chain antibody

<400> SEQUENCE: 19

```
caaattgtgc tgactcagtc tccagcaatc ctgtctgcat ttccagggga gaaggtcaca    60
atgacttgca gggccagctc aagtgtaagt tacatgcact ggtaccagca gaagccagga   120
tcctccccca aaccctggat ttatgccaca tccaacctgg cttctggagt ccctactcgc   180
ttcagtggca gtgggtctgg gacctcttac tctctcacaa tcagcagagt ggaggctgaa   240
gatgttgcca cttattactg cctacagtgg actagtaacc cacccacgtt cggtgctggg   300
accaagctgg agctgaaa                                                 318
```

<210> SEQ ID NO 20
<211> LENGTH: 372
<212> TYPE: DNA
<213> ORGANISM: Artificial Sequence
<220> FEATURE:
<223> OTHER INFORMATION: Description of Artificial Sequence: Synthetic
      DNA 391.4 heavy chain antibody

<400> SEQUENCE: 20

```
gaagtgaagc ttcatgagtc tggtggagga tttgtgcagc ctaaagggtc attgaaactc    60
tcatgtgcag cctctggatt caccttcaat gcctacgcca tgaactgggt ccgccaggct   120
ccaggaaagg gtttggaatg ggttgctcgc ataagaagta aaagtaataa ttatgaaaca   180
tattatgccg attcagtgaa agacaggttc accatctcca gagatgattc acaatacatg   240
gtctatctgc aaatgaacaa cctgaaaagt gaggacacag ccatgtatta ttgtgtgagg   300
agagggtcga tgcggtccgc ttattatgca atggactact ggggtcaagg aacctcagtc   360
accgtctcct ca                                                      372
```

-continued

```
<210> SEQ ID NO 21
<211> LENGTH: 106
<212> TYPE: PRT
<213> ORGANISM: Artificial Sequence
<220> FEATURE:
<223> OTHER INFORMATION: Description of Artificial Sequence: Synthetic
      DNA 391.4 light chain antibody

<400> SEQUENCE: 21

Gln Ile Val Leu Thr Gln Ser Pro Ala Ile Leu Ser Ala Phe Pro Gly
1               5                   10                  15

Glu Lys Val Thr Met Thr Cys Arg Ala Ser Ser Val Ser Tyr Met
            20                  25                  30

His Trp Tyr Gln Gln Lys Pro Gly Ser Ser Pro Lys Pro Trp Ile Tyr
        35                  40                  45

Ala Thr Ser Asn Leu Ala Ser Gly Val Pro Thr Arg Phe Ser Gly Ser
    50                  55                  60

Gly Ser Gly Thr Ser Tyr Ser Leu Thr Ile Ser Arg Val Glu Ala Glu
65                  70                  75                  80

Asp Val Ala Thr Tyr Tyr Cys Leu Gln Trp Ser Ser Asn Pro Pro Thr
                85                  90                  95

Phe Gly Ala Gly Thr Lys Leu Glu Leu Lys
            100                 105

<210> SEQ ID NO 22
<211> LENGTH: 123
<212> TYPE: PRT
<213> ORGANISM: Artificial Sequence
<220> FEATURE:
<223> OTHER INFORMATION: Description of Artificial Sequence: Synthetic
      DNA 391.4 heavy chain antibody

<400> SEQUENCE: 22

Glu Val Lys Leu His Glu Ser Gly Gly Gly Phe Val Gln Pro Lys Gly
1               5                   10                  15

Ser Leu Lys Leu Ser Cys Ala Ala Ser Gly Phe Thr Phe Asn Ala Tyr
            20                  25                  30

Ala Met Asn Trp Val Arg Gln Ala Pro Gly Lys Gly Leu Glu Trp Val
        35                  40                  45

Ala Arg Ile Arg Ser Lys Ser Asn Asn Tyr Glu Thr Tyr Tyr Ala Asp
    50                  55                  60

Ser Val Lys Asp Phe Thr Ile Ser Arg Asp Asp Ser Gln Tyr Met Val
65                  70                  75                  80

Tyr Leu Gln Met Asn Asn Leu Lys Ser Glu Asp Thr Ala Met Tyr Tyr
                85                  90                  95

Cys Val Arg Arg Gly Ser Met Arg Ser Tyr Tyr Tyr Ala Met Asp Tyr
            100                 105                 110

Trp Gly Gln Gly Thr Ser Val Thr Val Ser Ser
            115                 120
```